US012759989B2

(12) United States Patent
Choi et al.

(10) Patent No.: US 12,759,989 B2
(45) Date of Patent: Oct. 13, 2026

(54) ORGANIC COMPOUND AND ORGANIC LIGHT-EMITTING DIODE COMPRISING SAME

(71) Applicant: SFC CO., LTD., Cheongju-si (KR)

(72) Inventors: Yeong-Tae Choi, Yongin-si (KR); Se-Jin Lee, Daejeon (KR); Seok-Bae Park, Geumsan-gun (KR); Taejung Yu, Yongin-si (KR); Byung-Sun Yang, Namwon-si (KR); Dajung Lee, Bucheon-si (KR)

(73) Assignee: SFC CO., LTD., Cheongju-si (KR)

( * ) Notice: Subject to any disclaimer, the term of this patent is extended or adjusted under 35 U.S.C. 154(b) by 60 days.

(21) Appl. No.: 18/623,474

(22) Filed: Apr. 1, 2024

(65) Prior Publication Data

US 2024/0279196 A1 Aug. 22, 2024

Related U.S. Application Data

(63) Continuation of application No. 15/706,954, filed on Sep. 18, 2017, now abandoned.

(30) Foreign Application Priority Data

Oct. 5, 2016 (KR) ........................ 10-2016-0128394
Sep. 18, 2017 (KR) ........................ 10-2017-0119719

(51) Int. Cl.

| | |
|---|---|
| ***H01L 51/00*** | (2006.01) |
| ***C07D 307/91*** | (2006.01) |
| ***C07D 405/12*** | (2006.01) |
| ***C07D 409/12*** | (2006.01) |
| ***C07D 487/04*** | (2006.01) |
| ***C09K 11/06*** | (2006.01) |
| ***H10K 50/15*** | (2023.01) |
| ***H10K 85/60*** | (2023.01) |

(52) U.S. Cl.
CPC ......... *C07D 307/91* (2013.01); *C07D 405/12* (2013.01); *C07D 409/12* (2013.01); *C07D 487/04* (2013.01); *C09K 11/06* (2013.01); *H10K 50/15* (2023.02); *H10K 85/615* (2023.02); *H10K 85/633* (2023.02); *H10K 85/636* (2023.02); *H10K 85/657* (2023.02); *H10K 85/6574* (2023.02)

(58) Field of Classification Search
CPC ... H10K 85/657; H10K 85/6574; H10K 50/15
See application file for complete search history.

(56) References Cited

U.S. PATENT DOCUMENTS

| | | | | |
|---|---|---|---|---|
| 2012/0112174 | A1* | 5/2012 | Lee ...................... | C07D 333/50 548/440 |
| 2017/0222144 | A1* | 8/2017 | Haketa ................. | C07D 307/77 |
| 2018/0351111 | A1* | 12/2018 | Cha ...................... | H10K 85/633 |

FOREIGN PATENT DOCUMENTS

| | | | |
|---|---|---|---|
| KR | 20120047706 | A | 5/2012 |
| KR | 102656066 | B1 | 4/2024 |
| WO | WO2013007348 | A1 | 1/2013 |
| WO | WO2013182263 | A1 | 12/2013 |

OTHER PUBLICATIONS

The partial European search report of EP24 19 6363, Feb. 5, 2025.

* cited by examiner

*Primary Examiner* — Alexander C Kollias
(74) *Attorney, Agent, or Firm* — STIP Law Group, LLC

(57) ABSTRACT

Disclosed is an organic compound represented by any one of Chemical Formulas A to E and an organic light-emitting diode including the same. Chemical Formulas A to E are as described in the specification.

9 Claims, 1 Drawing Sheet

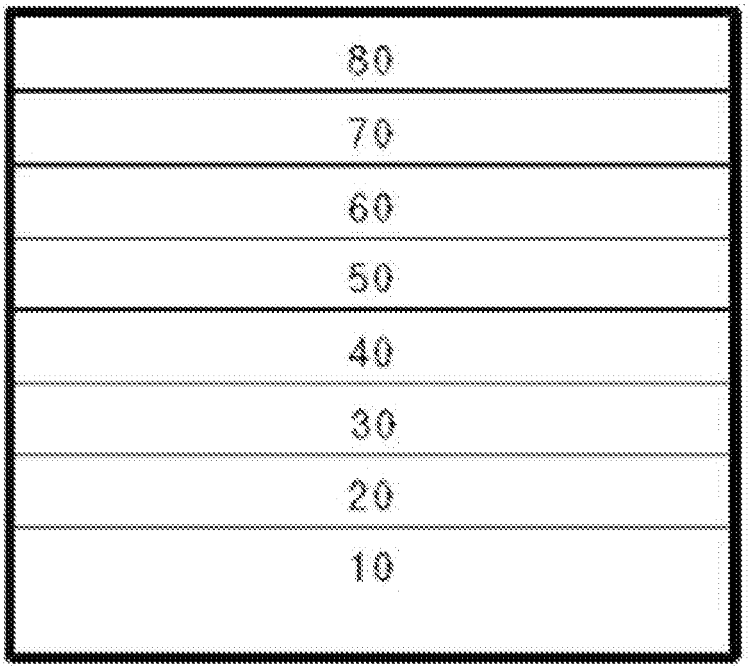
80
70
60
50
40
30
20
10

ORGANIC COMPOUND AND ORGANIC LIGHT-EMITTING DIODE COMPRISING SAME

CROSS-REFERENCE TO RELATED APPLICATIONS

This application is a Continuation of U.S. application Ser. No. 15/706,954, which claims the priority of Korean Patent Applications NO 10-2016-0128394 filed on Oct. 5, 2016, and NO 10-2017-0119719 filed on Sep. 18, 2017, in the Korean Intellectual Property Office, the disclosure of which is incorporated herein by reference.

1. FIELD OF THE INVENTION

The present disclosure relates to a novel organic compound and an organic light-emitting diode including the same. More particularly, the present disclosure relates to a novel organic compound that can guarantee the device properties of high efficiency, long lifespan, and low-voltage driving when used in an organic light-emitting diode, and an organic light-emitting diode including the same.

2. DESCRIPTION OF THE PRIOR ART

Organic light-emitting diodes (OLEDs), based on self-luminescence, enjoy the advantage of having a wide viewing angle and being able to be made thinner and lighter than liquid crystal displays (LCDs). In addition, an OLED display exhibits a very fast response time. Accordingly, OLEDs find applications in the illumination field as well as the full-color display field.

In general, the term "organic light-emitting phenomenon" refers to a phenomenon in which electrical energy is converted to light energy by means of an organic material. An OLED using the organic light-emitting phenomenon has a structure usually comprising an anode, a cathode, and an organic material layer interposed therebetween.

In this regard, the organic material layer may be, for the most part, of a multilayer structure consisting of different materials, for example, a hole injection layer, a hole transport layer, a light-emitting layer, an electron transport layer, and an electron injection layer. In the organic light-emitting diode having such a structure, when a voltage is applied between the two electrodes, a hole injected from the anode migrates to the organic layer while an electron is released from the cathode and moves toward the organic layer. In the luminescent zone, the hole and the electron recombine to produce an exciton. When the exciton returns to the ground state from the excited state, the molecule of the organic layer emits light. Such an organic light-emitting diode is known to have characteristics such as self-luminescence, high luminance, high efficiency, low driving voltage, a wide viewing angle, high contrast, and high-speed response.

Materials used as organic layers in OLEDs may be divided into luminescent materials and charge transport materials, for example, a hole injection material, a hole transport material, an electron injection material, and an electron transport material and, as needed, further into an electron-blocking material or a hole-blocking material.

With regard to related arts pertaining to hole transport layers, reference may be made to Korean Patent No. 10-1074193 (issued Oct. 14, 2011), which describes an organic light-emitting diode using a carbazole structure fused with at least one benzene ring in a hole transport layer, and Korean Patent No. 10-1455156 (issued Oct. 27, 2014), which describes an organic light-emitting diode in which the HOMO energy level of an auxiliary light-emitting layer is set between those of a hole transport layer and a light-emitting layer.

In spite of enormous effort for fabricating organic light-emitting diodes having more effective luminous properties, there is still continued need to develop novel organic light-emitting materials suitable for use in hole injection layers and hole transport layers of organic light-emitting diodes that can operate at lower voltage with higher light emission efficiency and longer lifespan, compared to those developed based on conventional technology.

RELATED ART DOCUMENT

Korean Patent No. 10-1074193 (issued Oct. 14, 2011)

Korean Patent No. 10-1455156 (issued Oct. 27, 2014)

SUMMARY OF THE INVENTION

Accordingly, a purpose of the present disclosure is to provide an organic compound having a specific structure, which is available for use in a hole transport layer of an OLED to guarantee a high efficiency, a low voltage, and a long lifespan for the OLED.

Another purpose of the present disclosure is to provide a novel OLED in which a hole transport layer contains the organic compound.

In order to accomplish the purposes thereof, the present disclosure provides an organic compound represented by any one of the following Chemical Formulas A to E:

[Chemical Formula A]

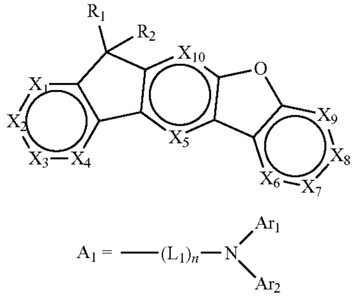

[Chemical Formula B]

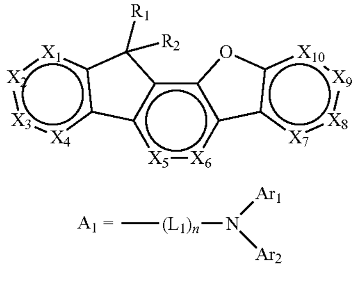

-continued

[Chemical Formula C]

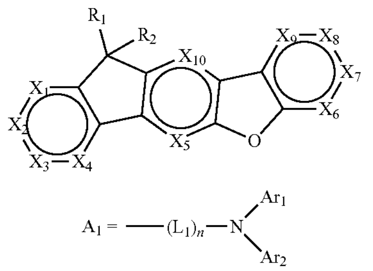

[Chemical Formula D]

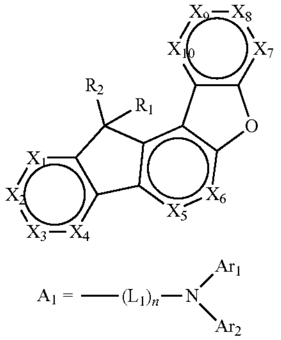

[Chemical Formula E]

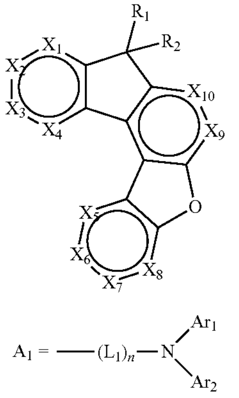

wherein,

X1 is CR11 or N,

X2 is CR12 or N,

X3 is CR13 or N,

X4 is CR14 or N,

X5 is CR15 or N,

X6 is CR16 or N,

X7 is CR17 or N,

X8 is CR18 or N,

X9 is CR19 or N, and

X10 is CR20 or N, wherein at least two of X1 to X4 are selected from among CR11 to CR14 and at least three of X5 to X10 are selected from among CR15 to CR20, with a proviso that one of X1 to X10 is a carbon atom connected to A1

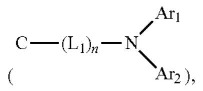

the substituents R1, R2, and R11 to R20, which may be the same or different, are each independently selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted heterocycloalkyl of 2 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, an alkylsilyl of 1 to 24 carbon atoms, an arylsilyl of 6 to 24 carbon atoms, a substituted or unsubstituted germanium, a substituted or unsubstituted boron, a substituted or unsubstituted aluminum, a carbonyl, a phosphoryl, an amino, a thiol, a cyano, a hydroxy, a nitro, a halogen, a selenium, a tellurium, an amide, an ether, and an ester, L1 denotes a linker and is any one selected from among a single bond, a substituted or unsubstituted alkylene of 1 to 60 carbon atoms, a substituted or unsubstituted cycloalkylene of 3 to 60 carbon atoms, a substituted or unsubstitutedarylene of 6 to 60 carbon atoms, and a substituted or unsubstituted heteroarylene of 2 to 60 carbon atoms, n is an integer of 0 to 3, with a proviso that when n is 2 or greater, the corresponding linkers L1's may be the same or different, and Ar1 and Ar2, which may be the same or different, are each independently any one selected from among a substituted or unsubstituted aryl of 6 to 40 carbon atoms and a substituted or unsubstituted heteroaryl of 2 to 30 carbon atoms, with a proviso that Ar1 may be connected to L1 to form a fused ring and Ar2 may be connected to L1 to form a fused ring in A1.

In accordance with another aspect thereof, the present disclosure provides an organic light-emitting diode, including a first electrode; a second electrode facing the first electrode; and an organic layer interposed between the first electrode and the second electrode, wherein the organic layer includes at least one of the organic compounds of the present disclosure.

BRIEF DESCRIPTION OF THE DRAWINGS

The above and other aspects, features and advantages of the present invention will be more apparent from the following detailed description taken in conjunction with the accompanying drawing, in which:

FIG. 1 is a schematic diagram of an OLED according to one embodiment of the present disclosure.

DETAILED DESCRIPTION OF THE EXEMPLARY EMBODIMENTS

Below, a detailed description is given of the present disclosure.

An organic compound according to the present disclosure has the structure represented by any one of the following Chemical Formulas A to E:

[Chemical Formula A]

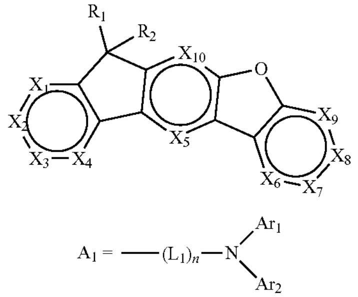

[Chemical Formula B]

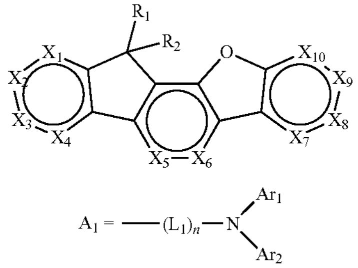

[Chemical Formula C]

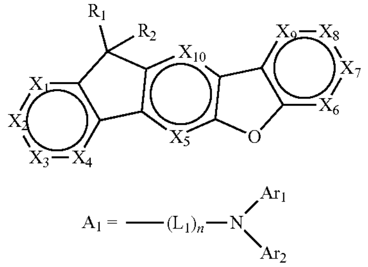

[Chemical Formula D]

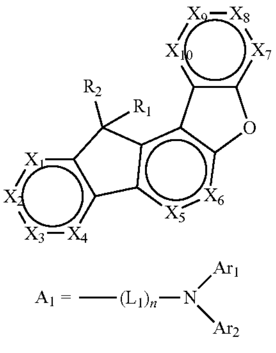

-continued

[Chemical Formula E]

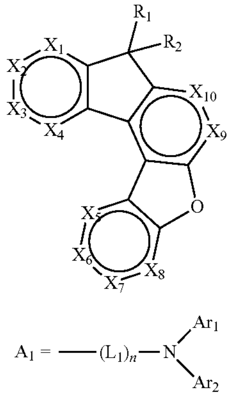

wherein,

X1 is CR11 or N,

X2 is CR12 or N,

X3 is CR13 or N,

X4 is CR14 or N,

X5 is CR15 or N,

X6 is CR16 or N,

X7 is CR17 or N,

X8 is CR18 or N,

X9 is CR19 or N, and

X10 is CR20 or N, wherein at least two of X1 to X4 are selected from among CR11 to CR14 and at least three of X5 to X10 are selected from among CR15 to CR20, with a proviso that one of X1 to X10 is a carbon atom connected to A1

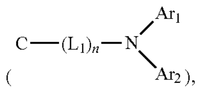

the substituents R1, R2, and R11 to R20, which may be the same or different, are each independently selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted heterocycloalkyl of 2 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, an alkylsilyl of 1 to 24 carbon atoms, an arylsilyl of 6 to 24 carbon atoms, a substituted or unsubstituted germanium, a substituted or unsubstituted boron, a substituted or unsubstituted aluminum, a carbonyl, a phosphoryl, an amino, a thiol, a cyano, a hydroxy, a nitro, a halogen, a selenium, a tellurium, an amide, an ether, and an ester, L1 denotes a linker and is any one selected from among a single bond, a substituted or unsubstituted alkylene of 1 to 60 carbon atoms, a substituted or unsubstituted cycloalkylene of 3 to 60 carbon atoms, a substituted or unsubstitutedarylene of 6 to 60 carbon atoms, and a substituted or unsubstituted heteroarylene of 2 to 60 carbon atoms, n is an integer of 0 to 3, with a proviso that when n is 2 or greater, the corresponding L1 linkers may be the same or different, and Ar1 and Ar2, which may be the same or different, are each independently any one selected from among a substituted or unsubstituted aryl of 6 to 40 carbon atoms and a substituted or unsubstituted heteroaryl of 2 to 30 carbon atoms, with a proviso that Ar1 may be connected to L1 to form a fused ring and Ar2 may be connected to L1 to form a fused ring in A1, wherein the term ‘substituted’ in the expression ‘substituted or unsubstituted’ means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 1 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 1 to 24 carbon atoms, a hetero arylamino of 1 to 24 carbon atoms, an alkylsilyl of 1 to 24 carbon atoms, an arylsilyl of 1 to 24 carbon atoms, and an aryloxy of 1 to 24 carbon atoms.

The expression indicating the number of carbon atoms such as in “a substituted or unsubstituted alkyl of 1 to 30 carbon atoms”, “a substituted or unsubstituted aryl of 6 to 50 carbon atoms”, etc. means the total number of carbon atoms of, for example, the alkyl or aryl radical or moiety alone, exclusive of the number of carbon atoms of the substituent. For instance, a phenyl group with a butyl at the para position falls within the scope of an aryl of 6 carbon atoms although it is substituted with a butyl radical of 4 carbon atoms.

As used herein, the term “aryl” means an organic radical derived from an aromatic hydrocarbon by removing one hydrogen atom and encompasses a 5- to 7-membered and preferably a 5- or 7-membered monocyclic ring or fused ring system. Further, the aromatic system may include a fused ring that is formed by adjacent substituents, if present, on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino ($—NH_2$, —NH(R), —N(R') (R") wherein R' and R" are each independently an alkyl of 1 to 10 carbon atoms, in this case called “alkylamino”), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms bearing one to three heteroatoms selected from among N, O, P, Si, S, Ge, Se, and Te. In the aromatic system, two or more rings may be fused. One or more hydrogen atoms on the heteroaryl may be substituted by the same substituents as on the aryl.

As used herein, the term “heteroaromatic ring” refers to an aromatic hydrocarbon ring bearing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy used in the compounds of the present disclosure include methoxy, ethoxy, propoxy, sec-butyloxy, iso-amyloxy, hexyloxy. At least one hydrogen atom of the alkoxy may be substituted by the same substituent as in the aryl.

Representative among the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atom in the silyl may be substituted by the same substituent as in the aryl.

The compound represented by any one of Chemical Formulas A to E will be elucidated in greater detail. The compound has an indenodibenzofuran structure in a fused form of a '6-membered aromatic ring bearing X1 to X4-5-membered ring with R1 and R2 attached to one carbon atom thereof—6-membered aromatic carbon ring bearing X5 and X10, X5 and X6, or X9 and X10-5-membered ring bearing an oxygen atom—6-membered aromatic carbon ring bearing X6 to X9, X7 to X10, or X5 to X8' wherein a nitrogen atom may be contained in the ring structure thereof and one of X1 to X10 is a carbo atom connected to A1

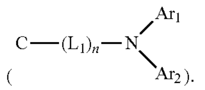

According to one embodiment of the present disclosure, the substituents Ar1 and Ar2 in Chemical Formulas A to E may be the same or different and may each be independently selected from among a substituted or unsubstituted aryl of 6 to 30 carbon atoms and a substituted or unsubstituted heteroaryl of 2 to carbon atoms, and more particularly may be the same or different and may each be independently a substituted or unsubstituted aryl of 6 to 30 carbon atoms.

According to another embodiment of the present disclosure, the substituents R11 to R20 on the carbon atoms which are not directly connected to A1 in Chemical Formulas A to E may each be a hydrogen atom or a deuterium atom.

According to another embodiment of the present disclosure, the linker L1 in Chemical Formulas A to E may be a single bond or any one selected from among the following Structural Formulas 1 to 9.

[Structural Formula 1]

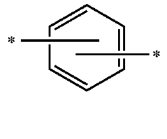

-continued

[Structural Formula 2]

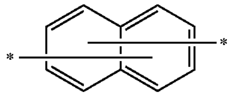

[Structural Formula 3]

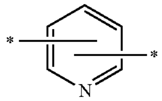

[Structural Formula 4]

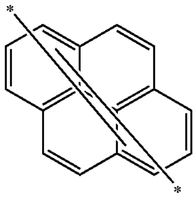

[Structural Formula 5]

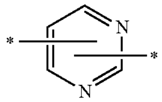

[Structural Formula 6]

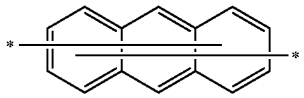

[Structural Formula 7]

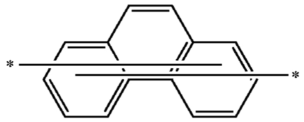

[Structural Formula 8]

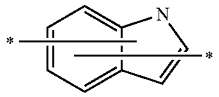

[Structural Formula 9]

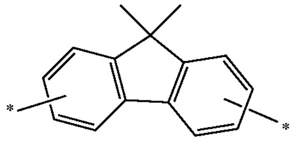

wherein carbon atoms in the aromatic ring moieties are bonded to a hydrogen atom or a deuterium atom.

According to another embodiment of the present disclosure, n in Chemical Formulas A to E is an integer of 1 or 2, with a proviso that when n is 2, the corresponding L1 linker may be the same or different.

According to the present disclosure, only one or none of X1 to X10 in the compounds represented by Chemical Formulas A to E may be a nitrogen atom.

Meanwhile, an organic compound represented by any one of Chemical Formulas A to E can exhibit more improved longevity properties when the compound has A1 bonded to position 1 of the dibenzofuran moiety than other positons.

In this regard, elements of dibenzofuran are numbered as shown in Diagram A, below.

<Diagram A>

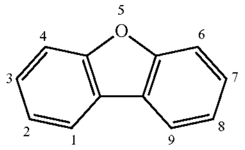

Atoms of the dibenzofuran moiety in each of Chemical Formulas A to E may be numbered in such a manner that the 6-membered ring outside the furan ring in the 6-5-6-5-6 fused ring structure corresponds to the left portion of the dibenzofuran in Diagram A. In the present disclosure, therefore, position 1 of the dibenzofuran moiety is given to X6 for Chemical Formula A, X7 for Chemical Formula B, X9 for Chemical Formula C, X10 for Chemical Formula D, and X5 for Chemical Formula E. Greater improved longevity properties can be elicited when A1 is bonded to the carbon atom of X6 in Chemical Formula A, X7 in Chemical Formula B, X9 in Chemical Formula C, X10 in Chemical Formula D, and X5 in Chemical Formula E.

Examples of the organic compound represented by any one of Chemical Formulas A to E include, but are not limited to, the compounds represented by the following Compounds 1 to 328.

<Compound 1>

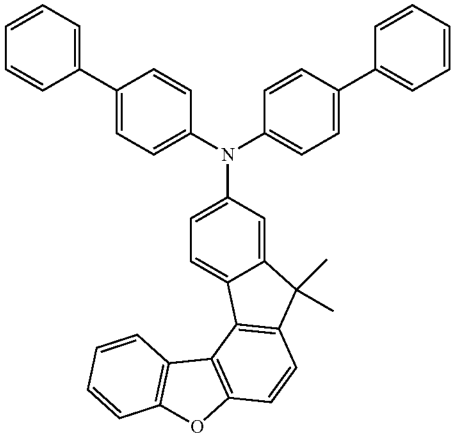

<Compound 2>

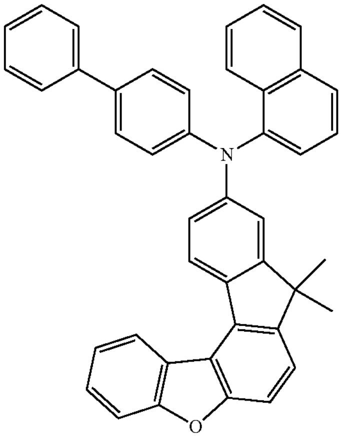

-continued
<Compound 3>
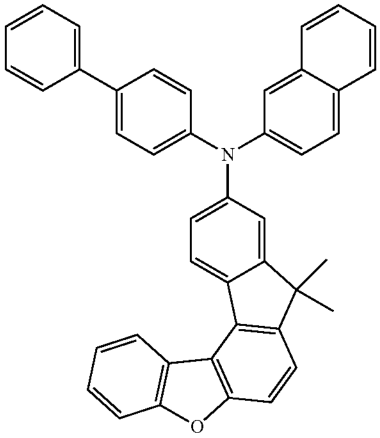
<Compound 4>
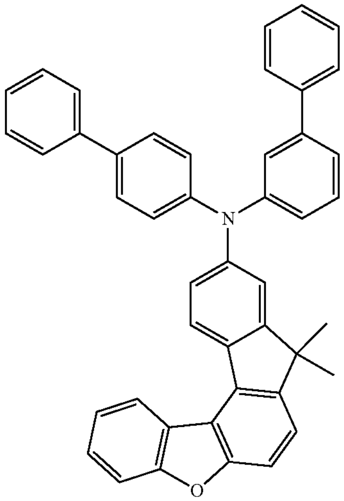
<Compound 5>
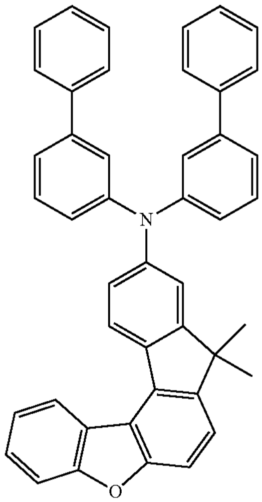
<Compound 6>
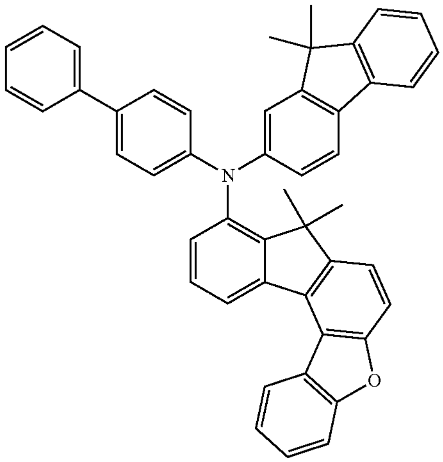
<Compound 7>
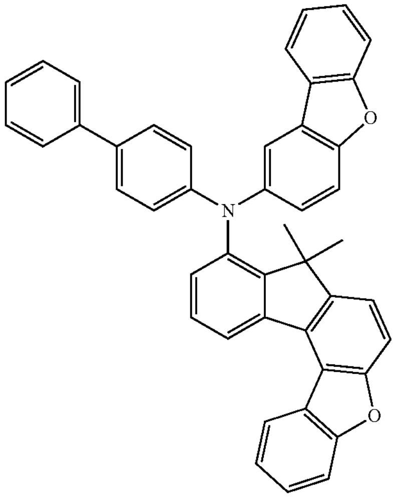
<Compound 8>
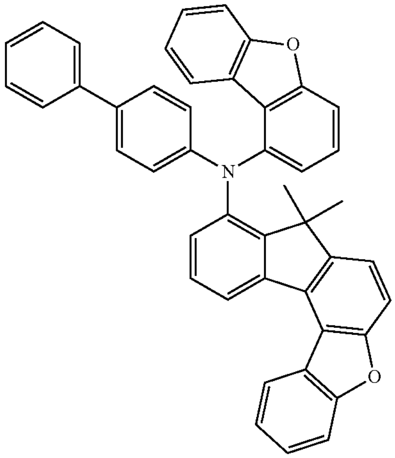

-continued
<Compound 9>
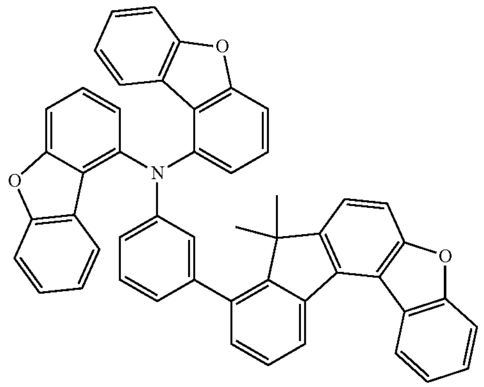
<Compound 10>
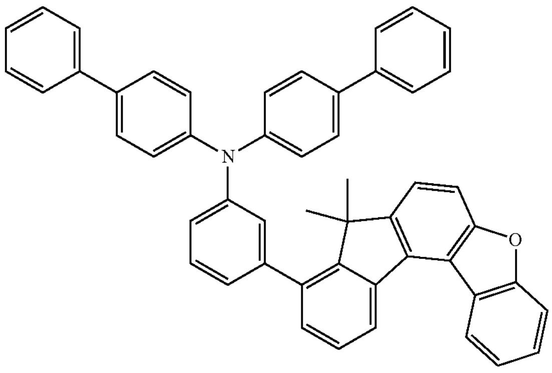
<Compound 11>
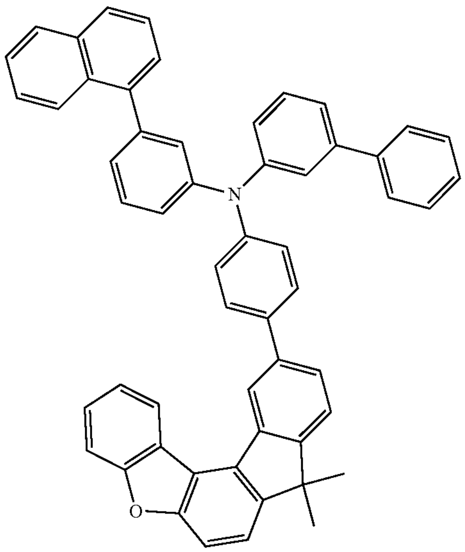
<Compound 12>
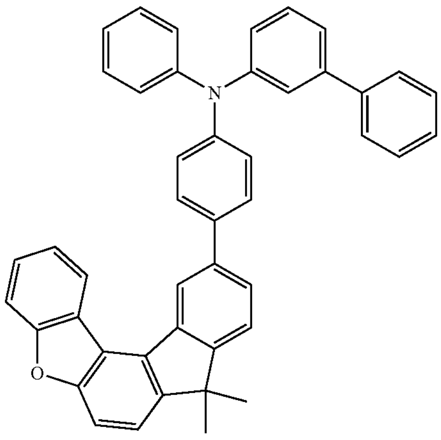
<Compound 13>
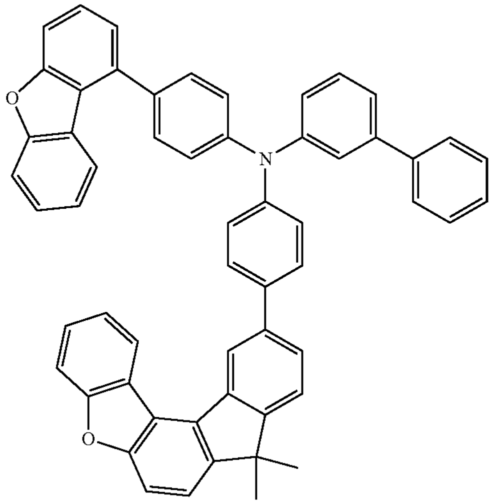
<Compound 14>
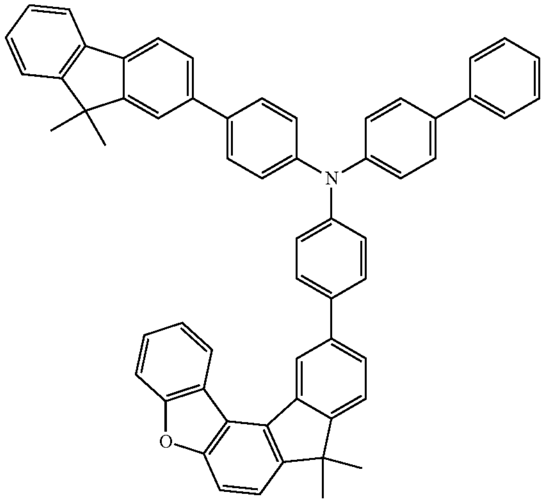

-continued
<Compound 15>
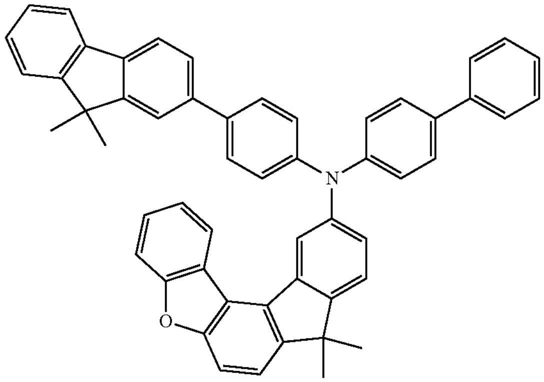
<Compound 16>
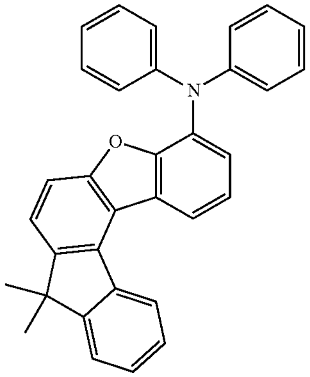
<Compound 17>
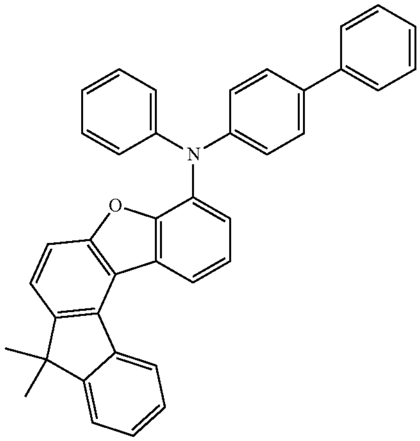
<Compound 18>
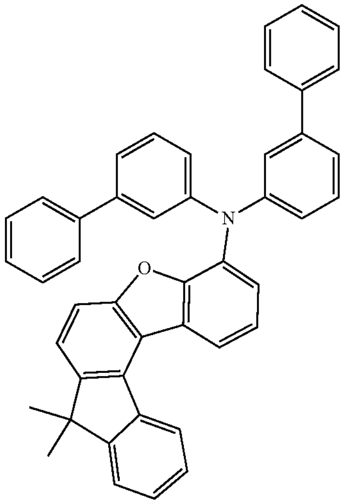
<Compound 19>
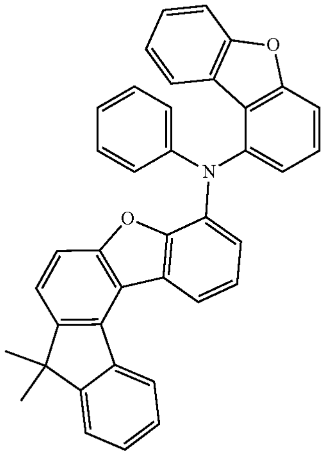
<Compound 20>
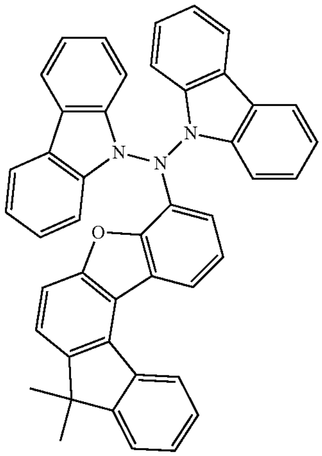

-continued
<Compound 21>
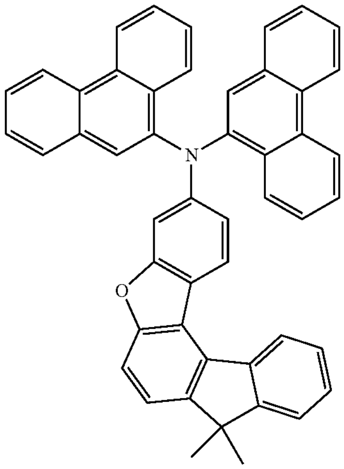
<Compound 22>
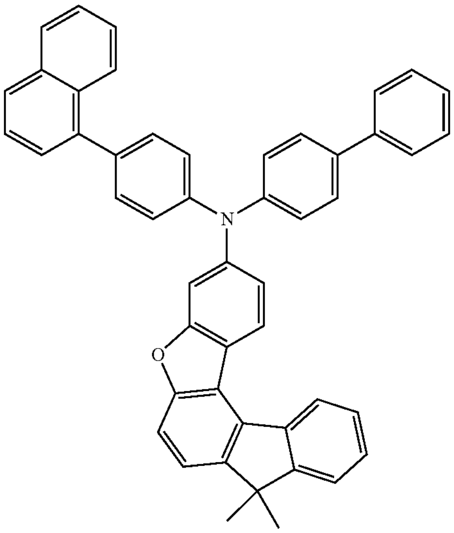
<Compound 23>
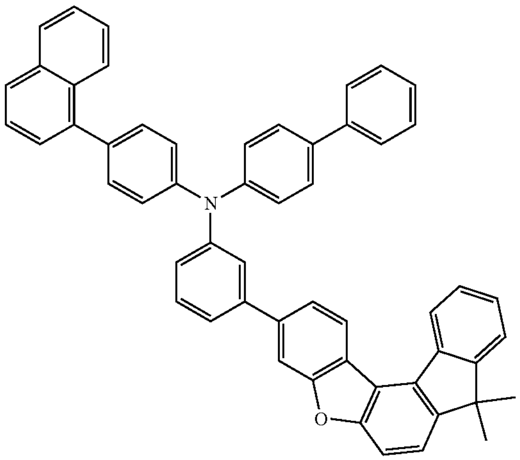
<Compound 24>
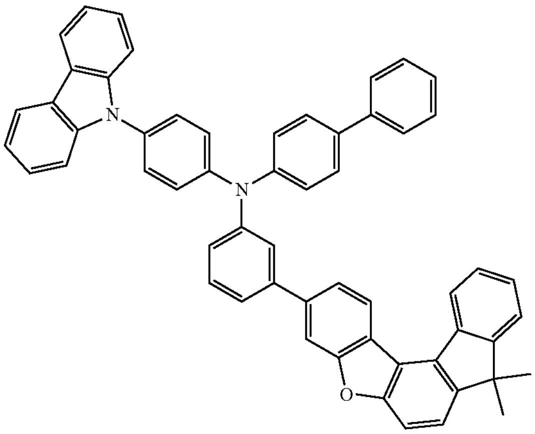
<Compound 25>
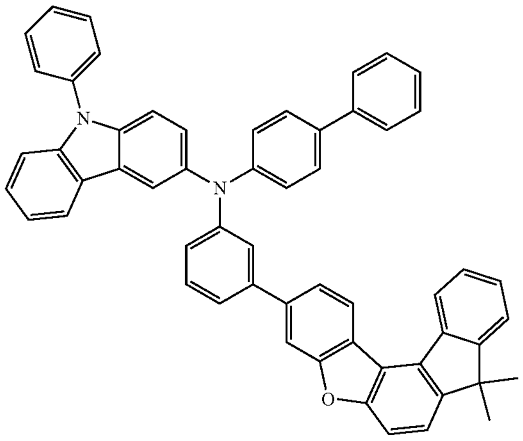
<Compound 26>
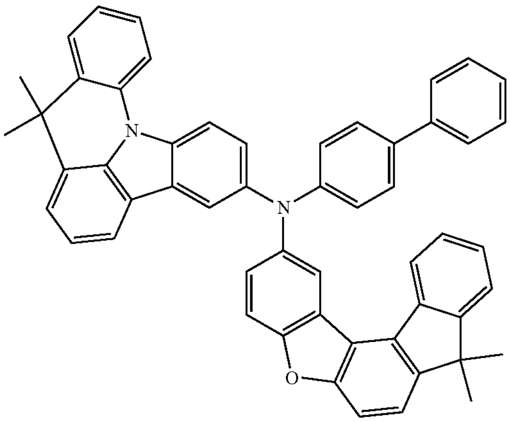

-continued
<Compound 27>
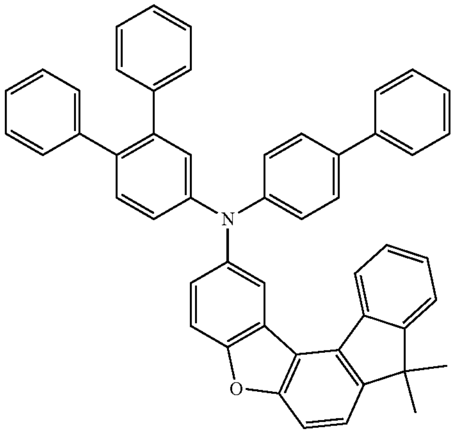
<Compound 28>
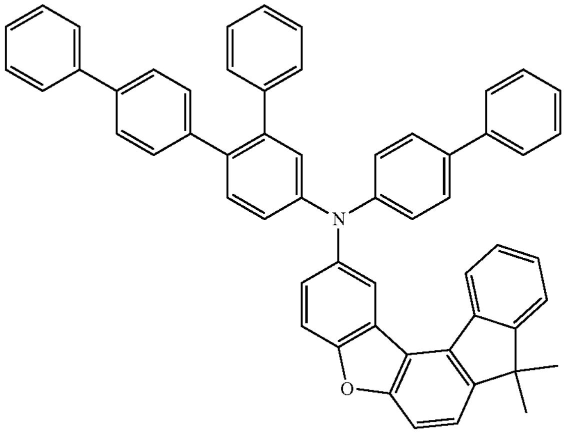
<Compound 29>
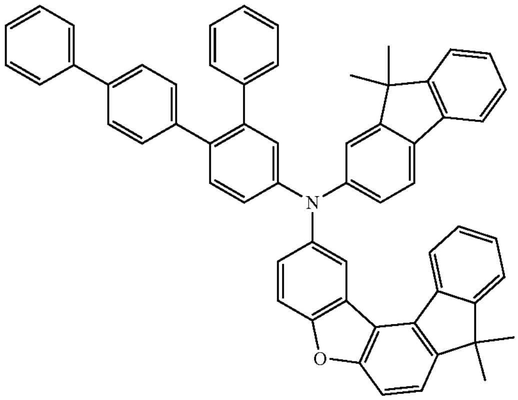
<Compound 30>
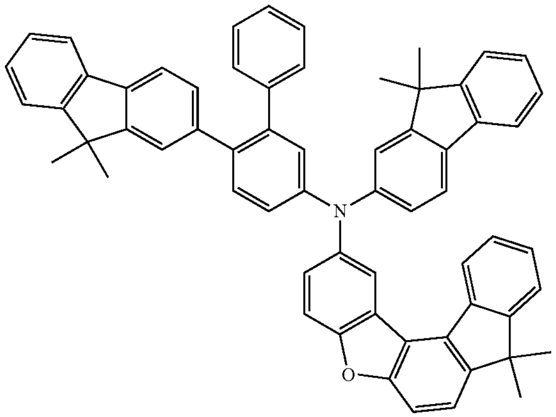
<Compound 31>
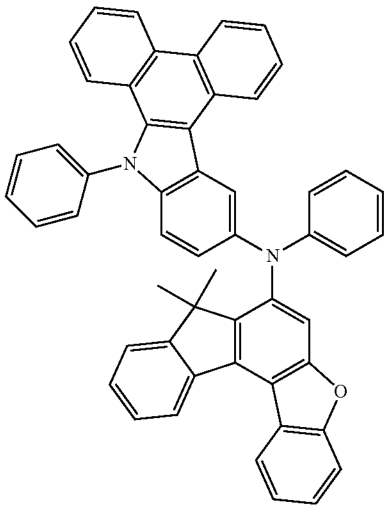
<Compound 32>
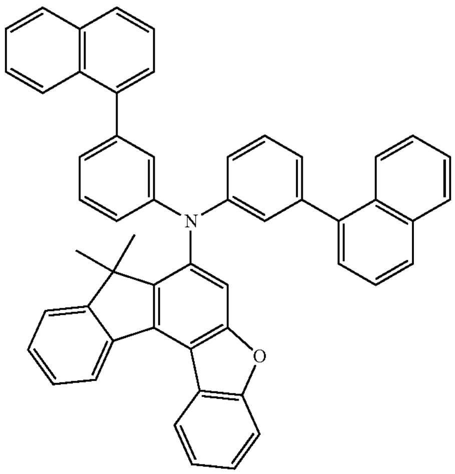

-continued
<Compound 33>
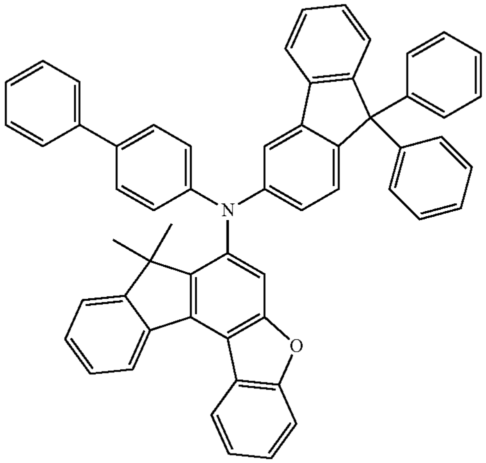
<Compound 34>
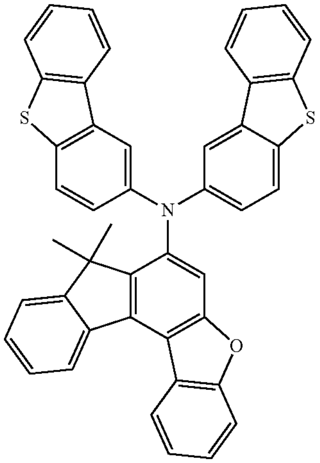
<Compound 35>
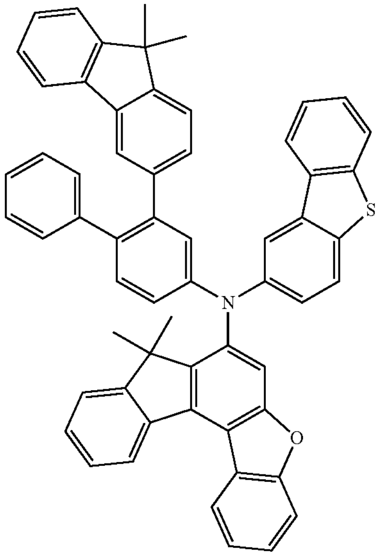
<Compound 36>
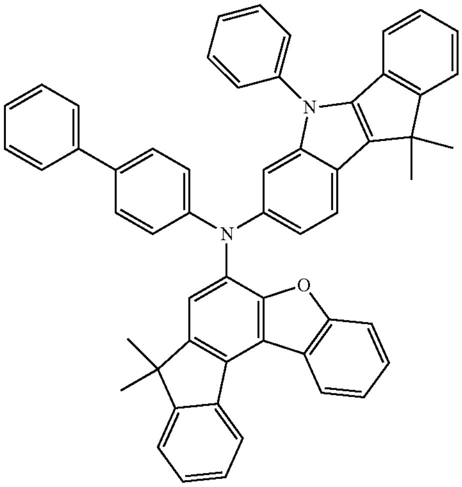
<Compound 37>
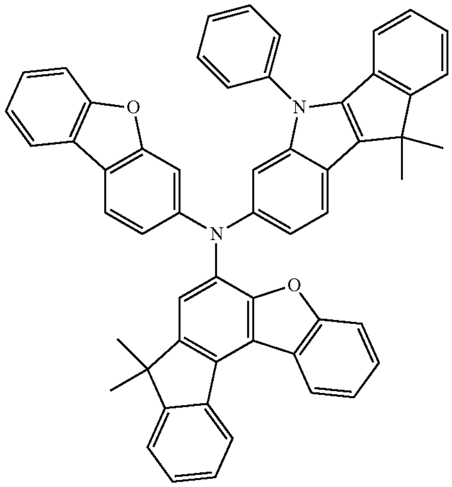
<Compound 38>
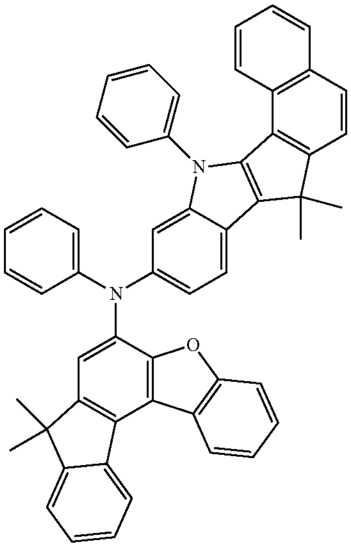

-continued
<Compound 39>
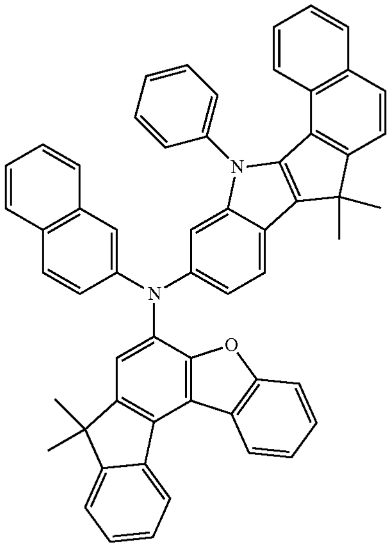
<Compound 40>
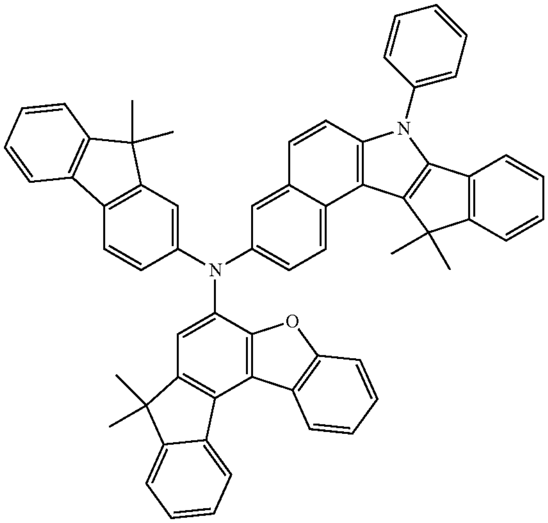
<Compound 41>
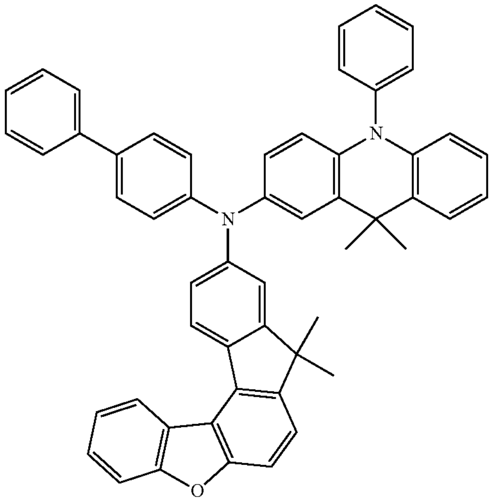
<Compound 42>
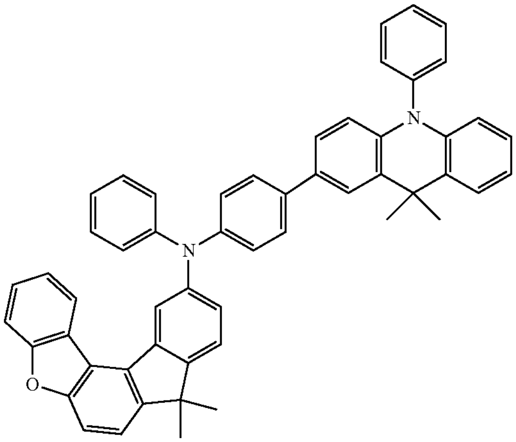
<Compound 43>
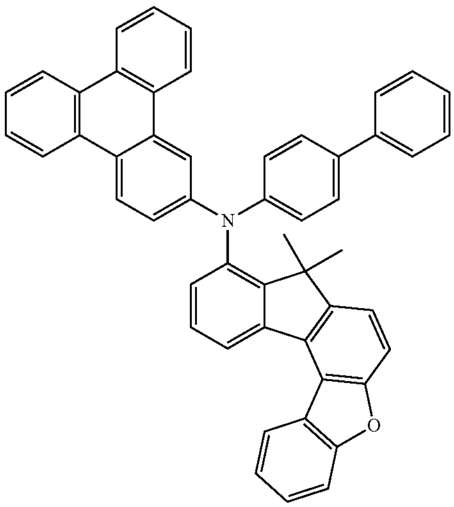
<Compound 44>
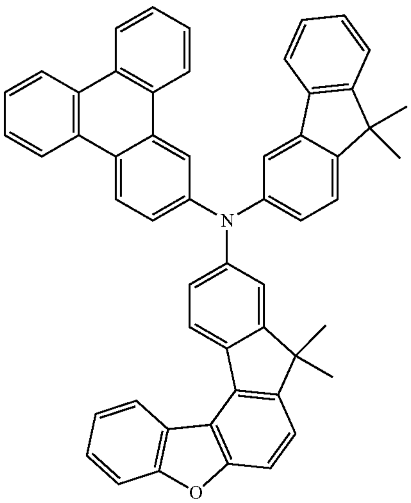

-continued
<Compound 45>
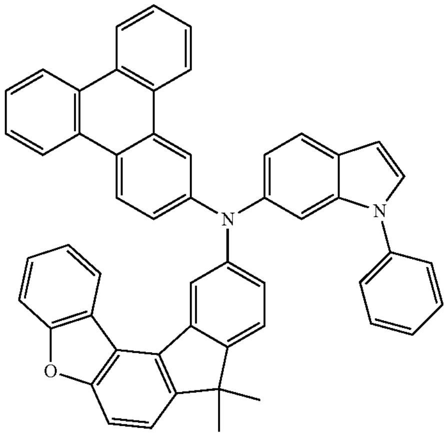
<Compound 46>
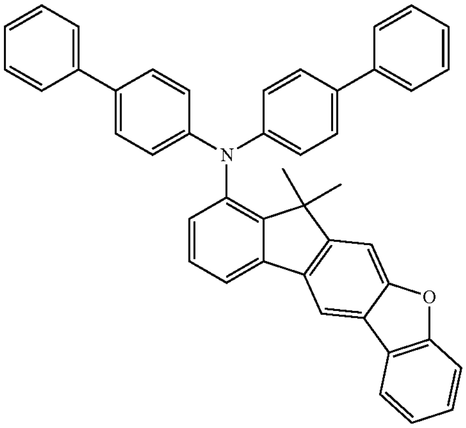
<Compound 47>
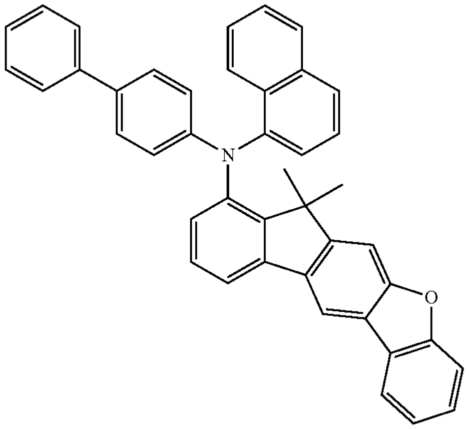
<Compound 48>
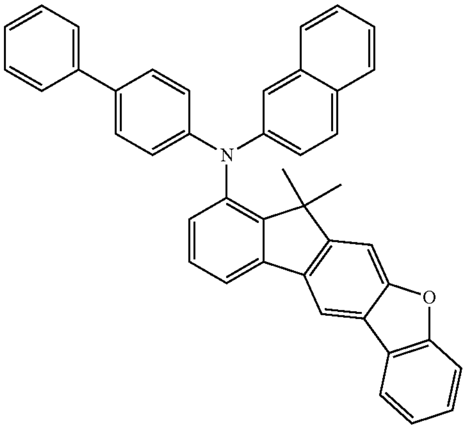
<Compound 49>
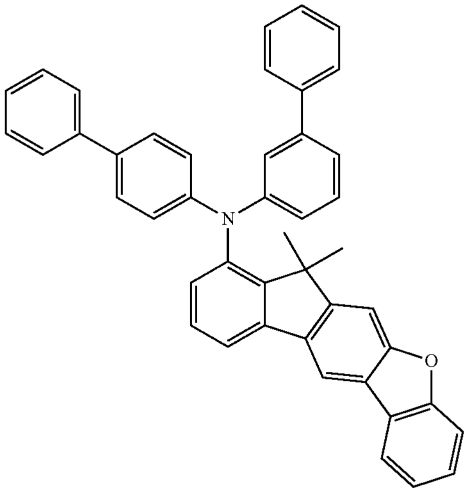
<Compound 50>
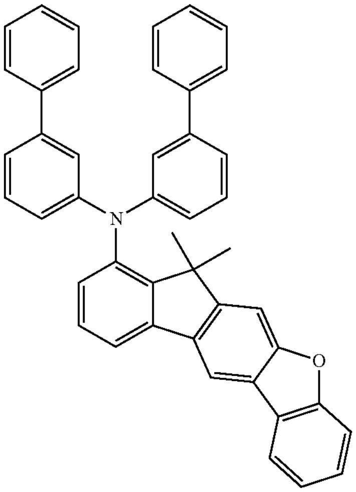

-continued
<Compound 51>
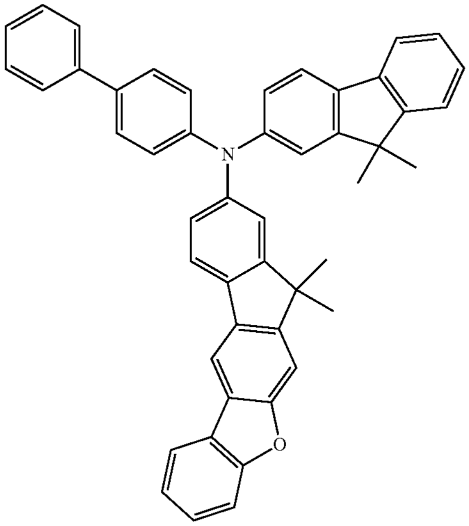
<Compound 52>
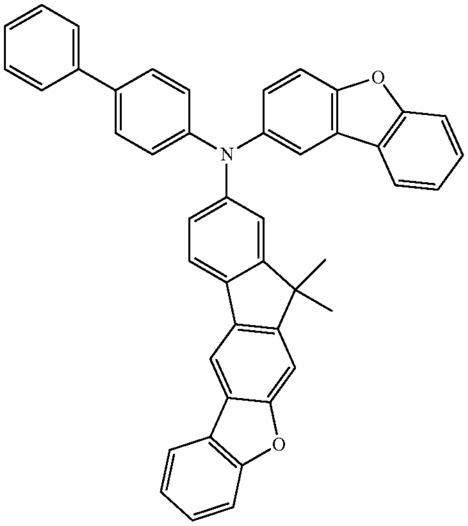
<Compound 53>
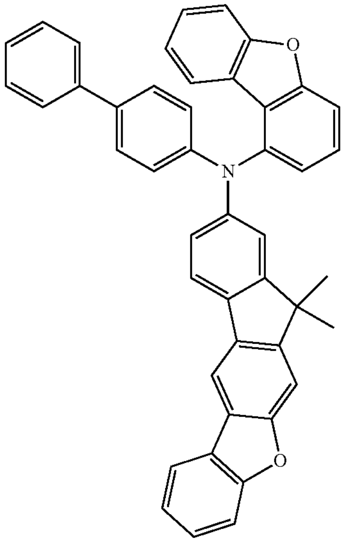
<Compound 54>
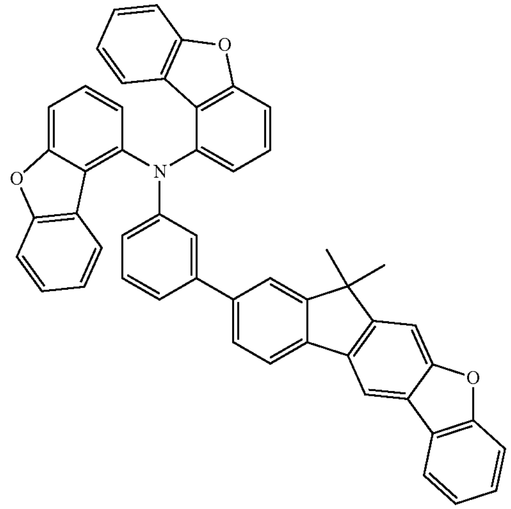

-continued
<Compound 55>
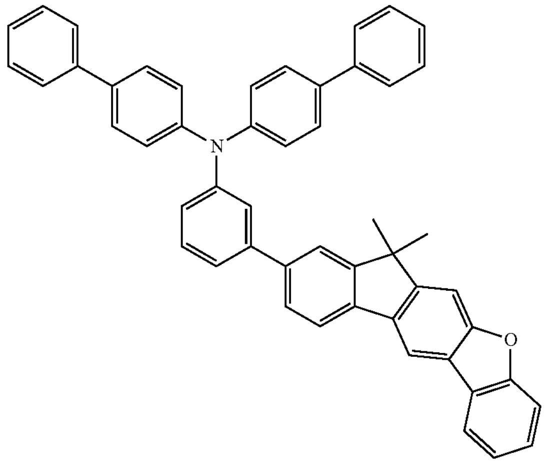
<Compound 56>
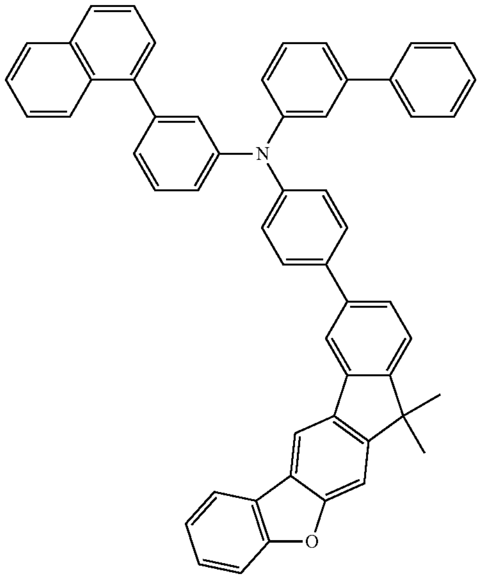
<Compound 57>
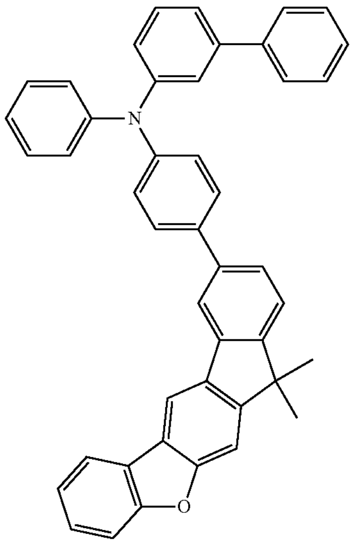
<Compound 58>
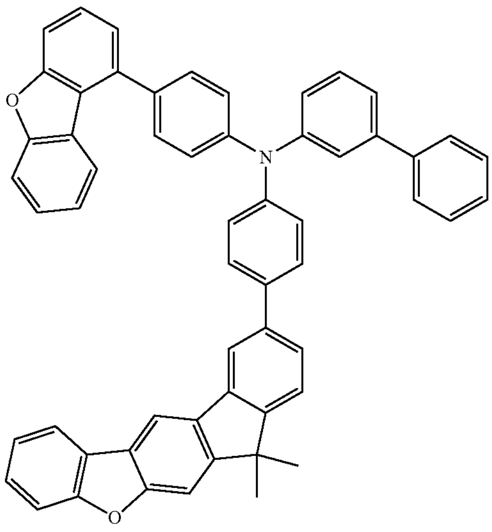

-continued
<Compound 59>
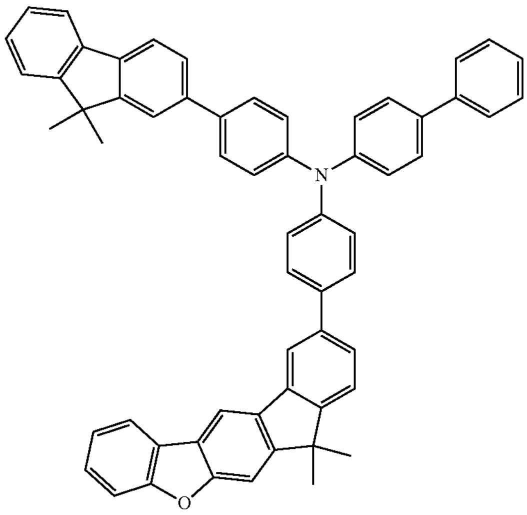
<Compound 60>
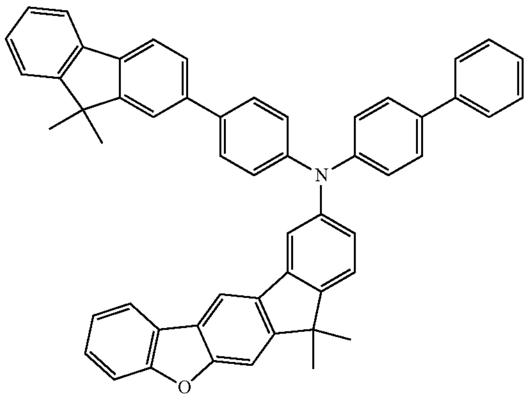
<Compound 61>
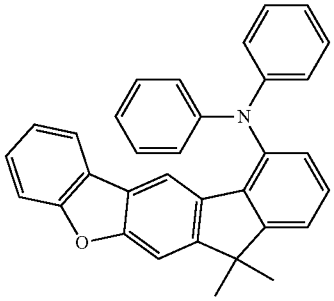
<Compound 62>
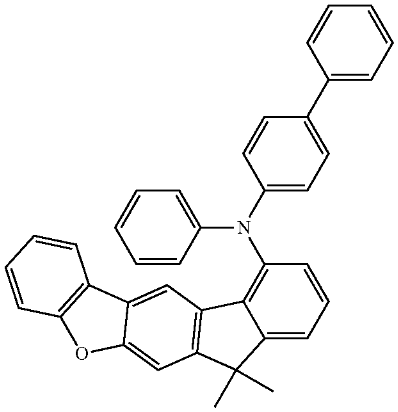
<Compound 63>
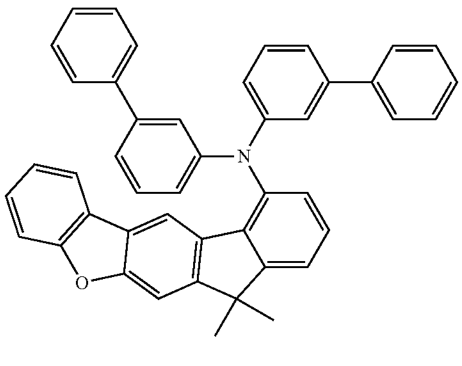
<Compound 64>
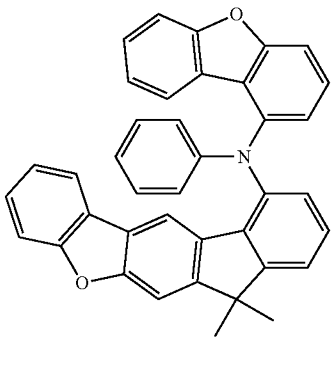

-continued
<Compound 65>
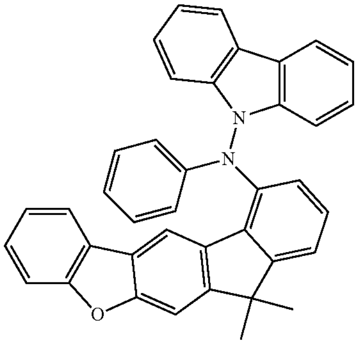
<Compound 66>
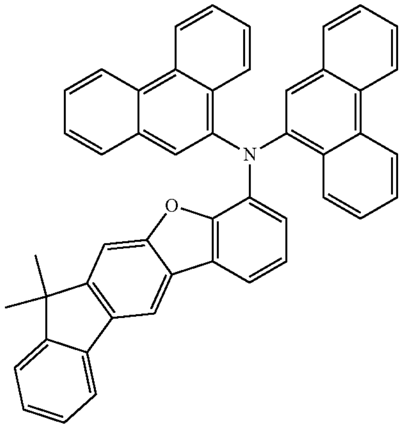
<Compound 67>
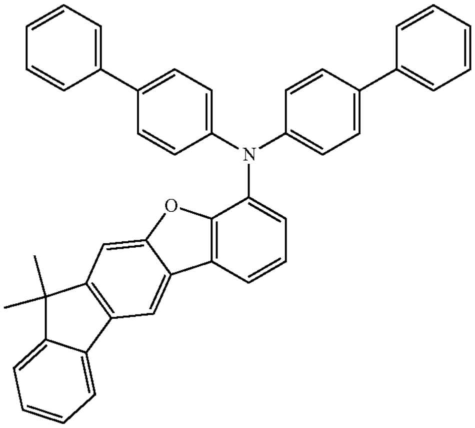
<Compound 68>
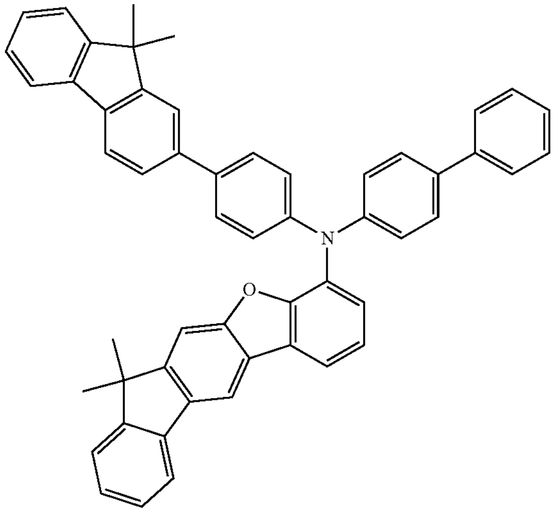
<Compound 69>
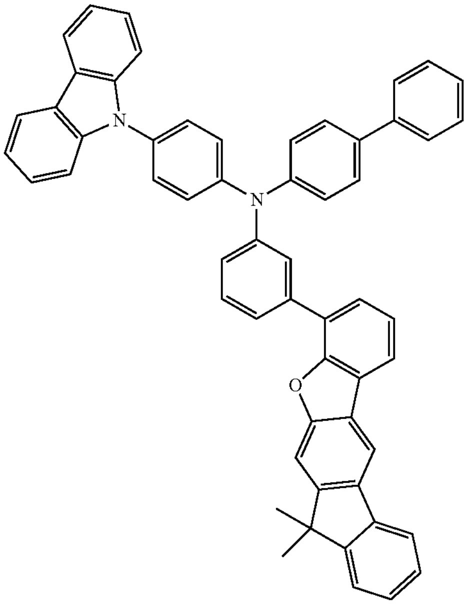
<Compound 70>
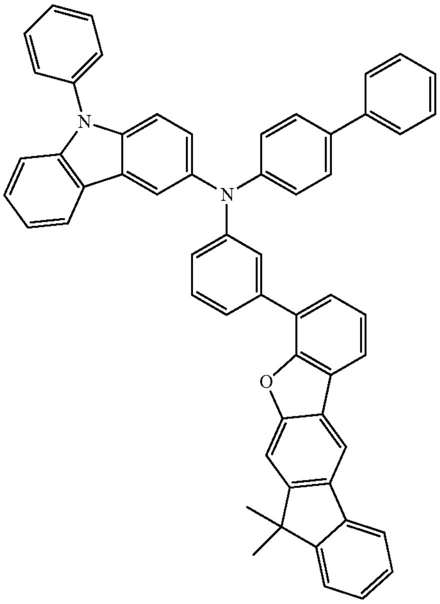

-continued
<Compound 71>
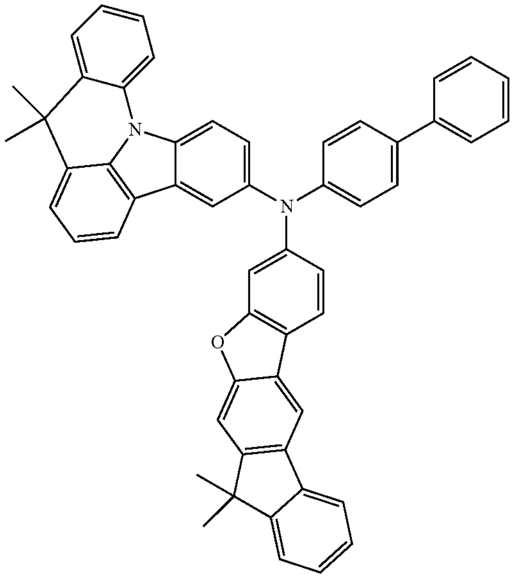
<Compound 72>
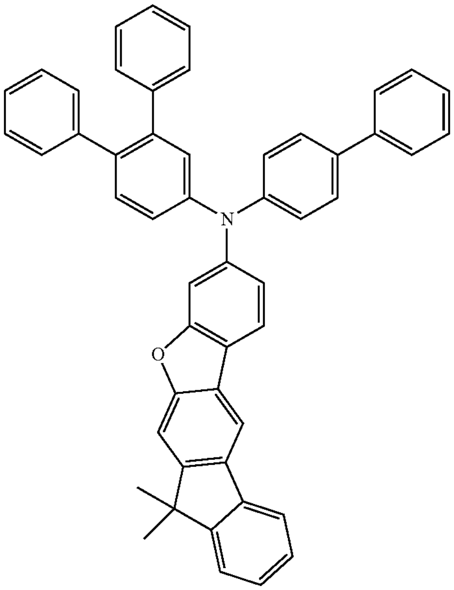
<Compound 73>
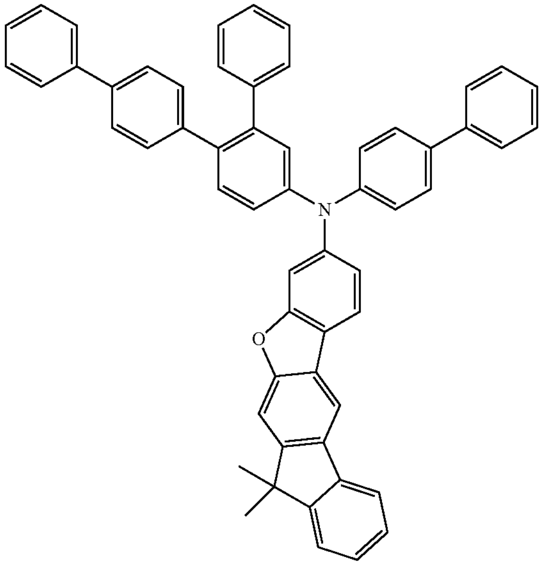
<Compound 74>
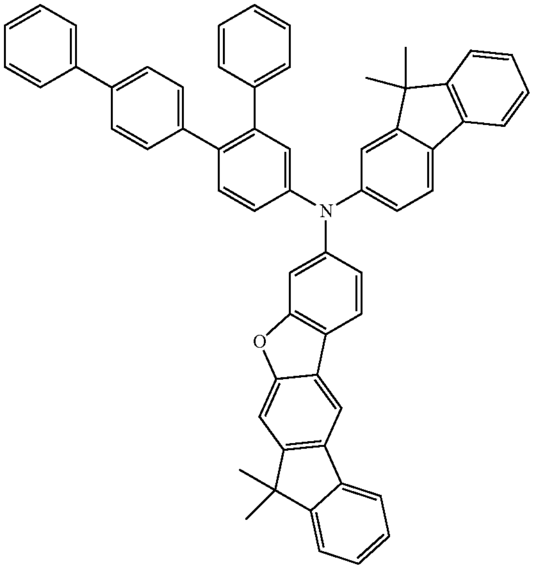

-continued
<Compound 75>
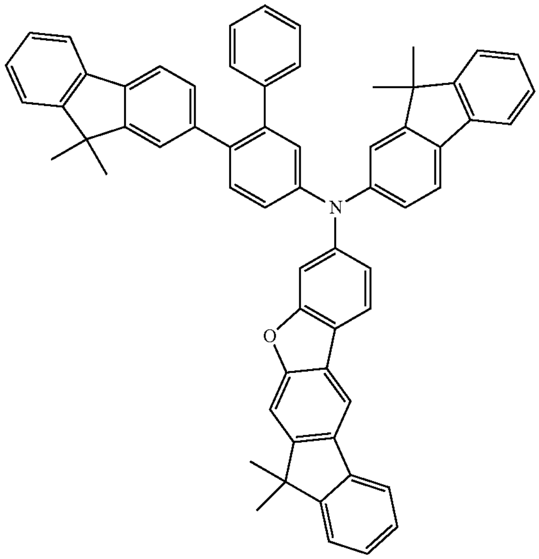
<Compound 76>
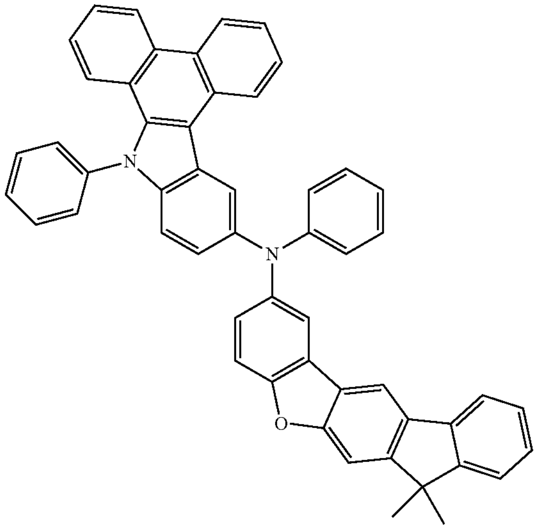
<Compound 77>
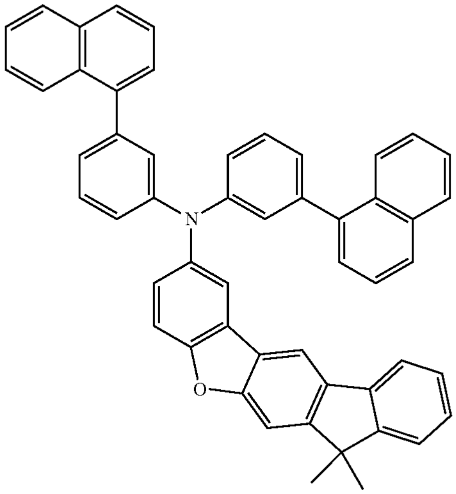
<Compound 78>
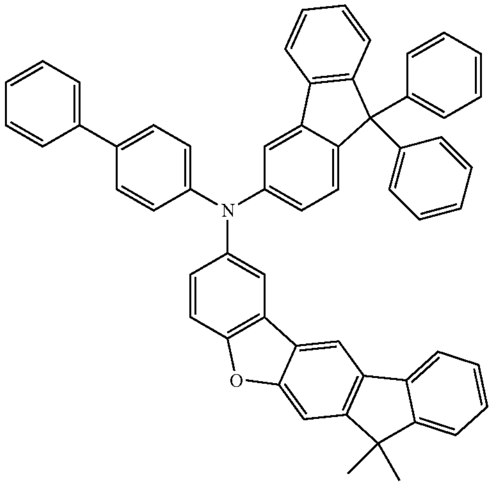

-continued
<Compound 79>
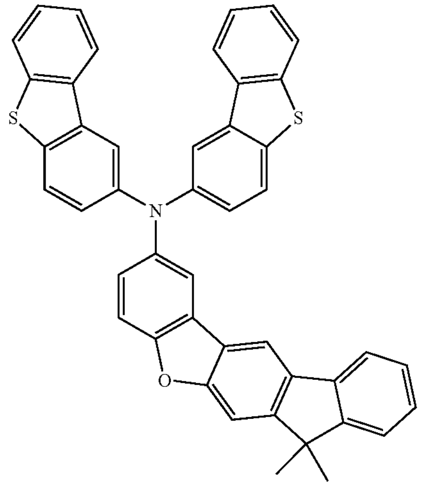
<Compound 80>
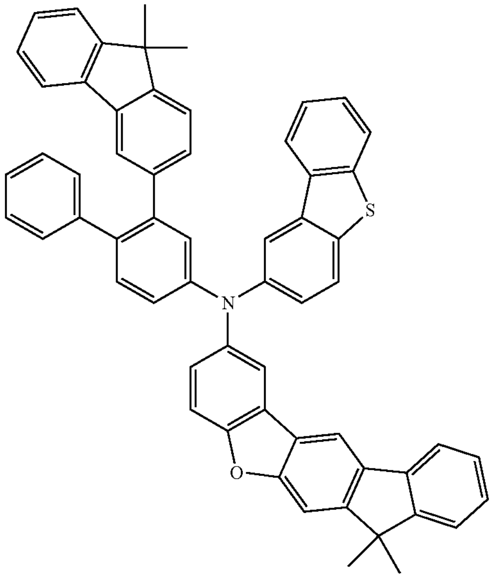
<Compound 81>
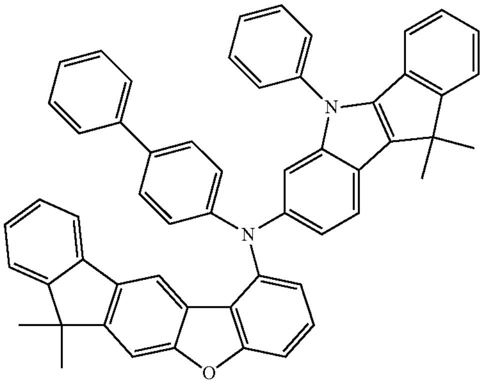
<Compound 82>
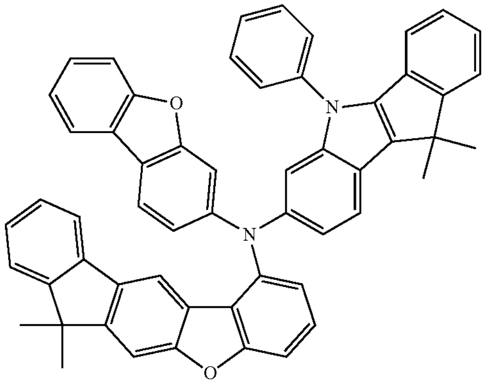
<Compound 83>
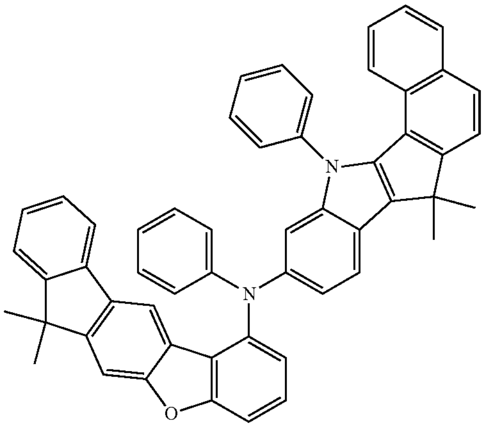
<Compound 84>
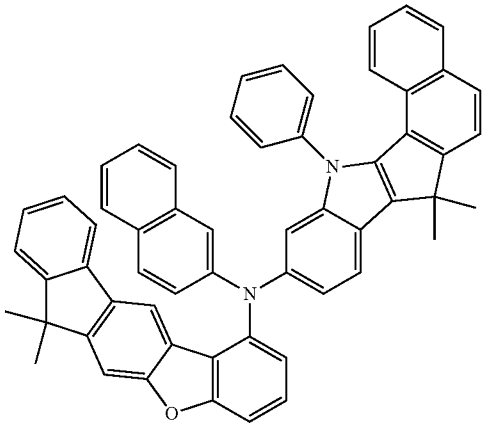

-continued
<Compound 85>
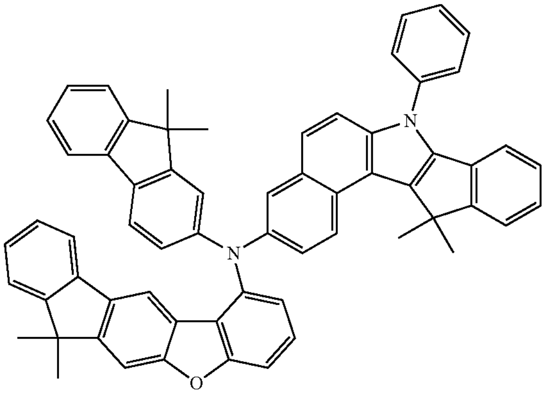
<Compound 86>
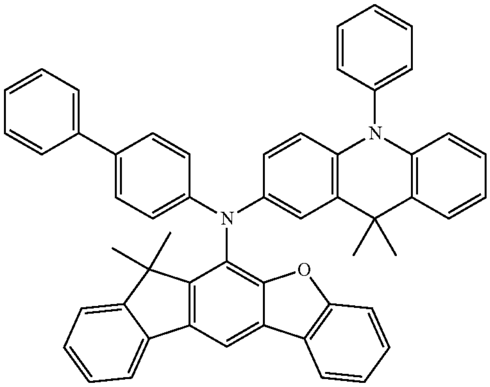
<Compound 87>
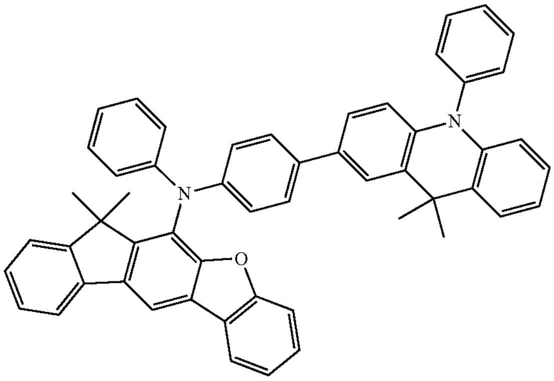
<Compound 88>
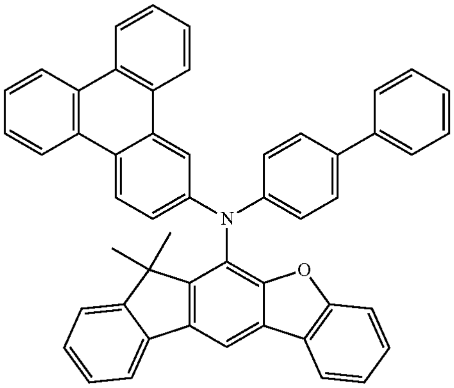
<Compound 89>
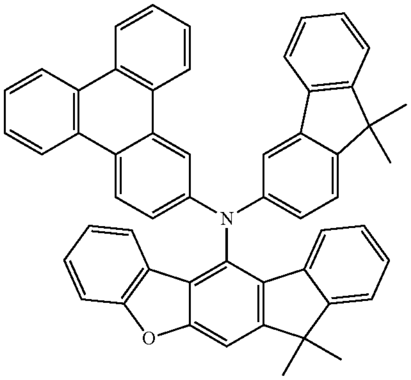
<Compound 90>
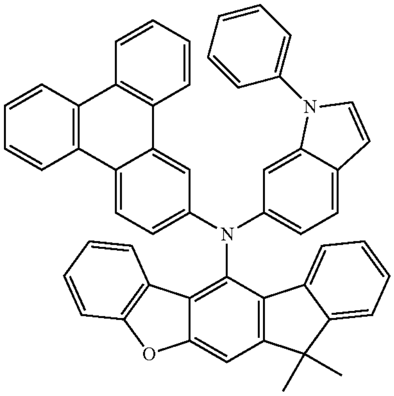
<Compound 91>
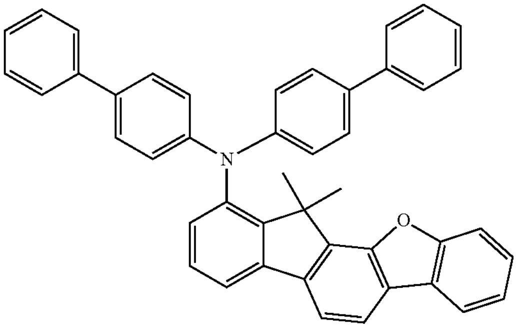
<Compound 92>
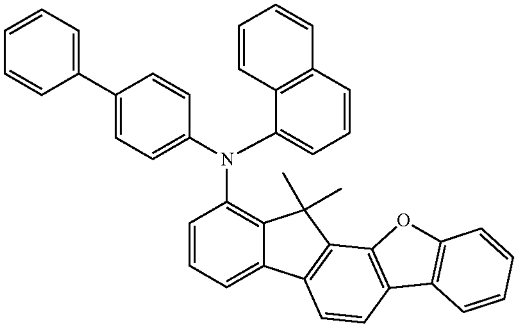

-continued
<Compound 93>
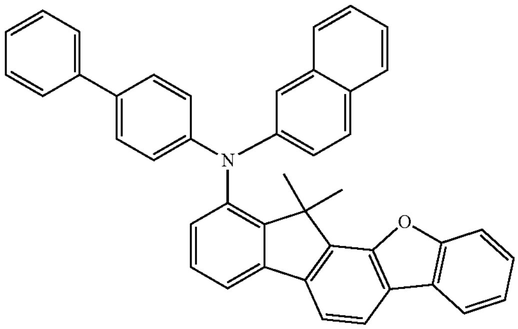
<Compound 94>
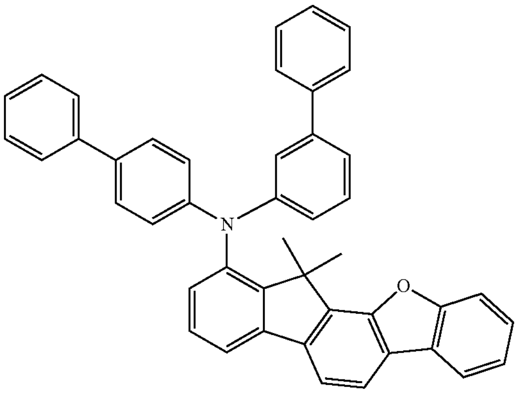
<Compound 95>
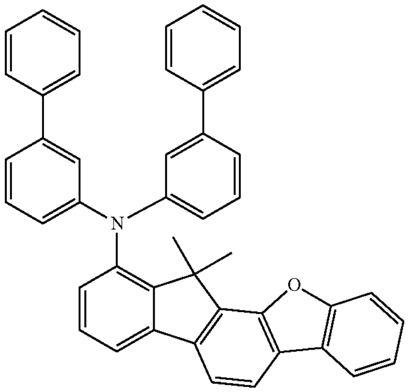
<Compound 96>
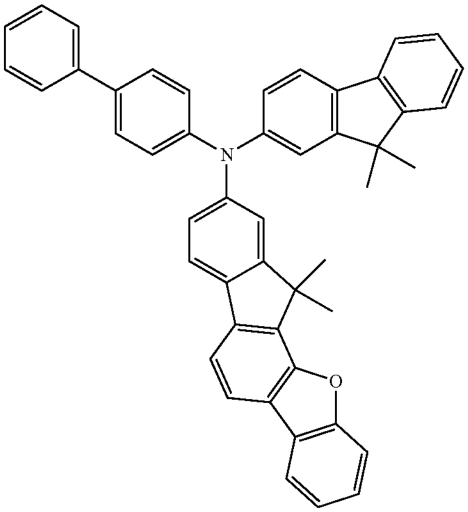
<Compound 97>
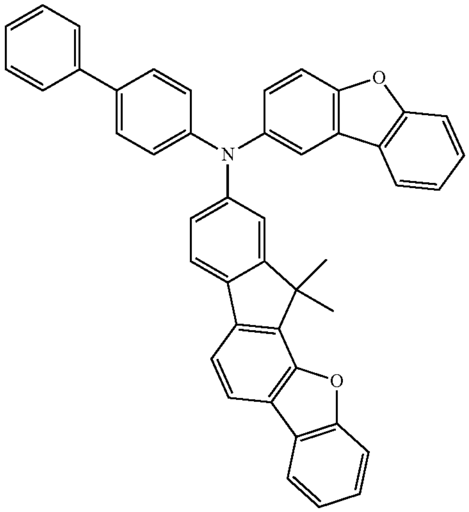
<Compound 98>
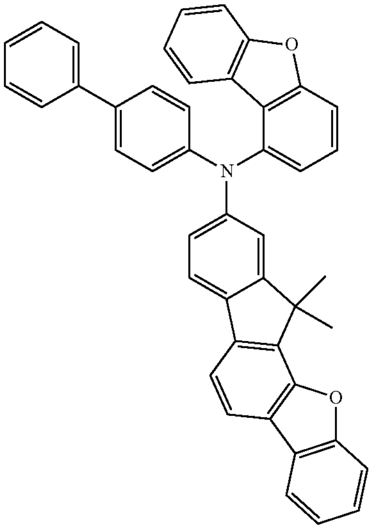

-continued
<Compound 99>
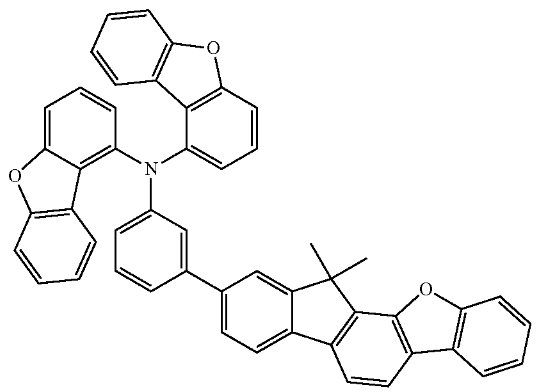
<Compound 100>
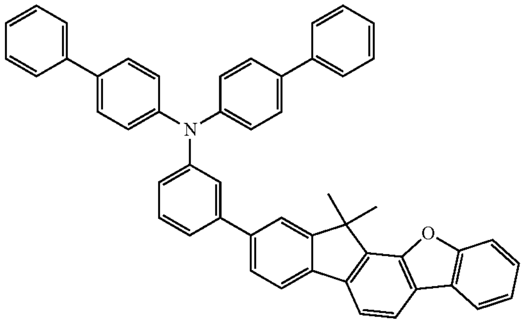
<Compound 101>
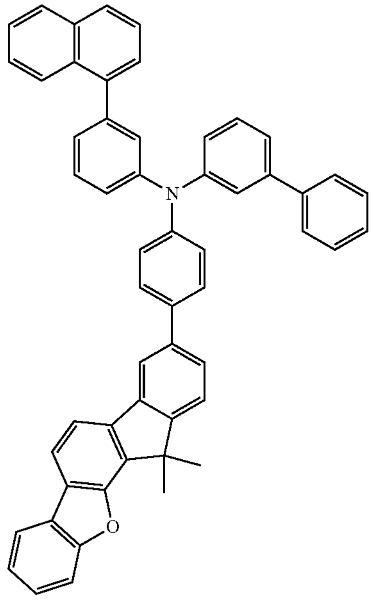
<Compound 102>
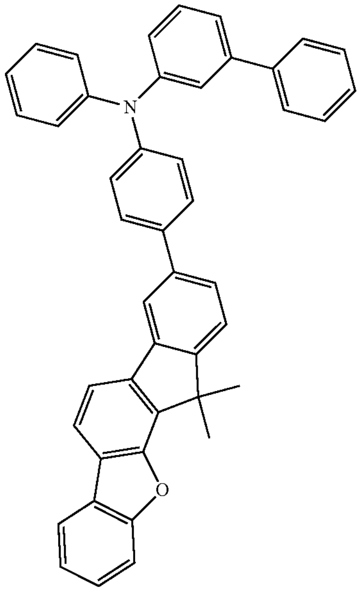
<Compound 103>
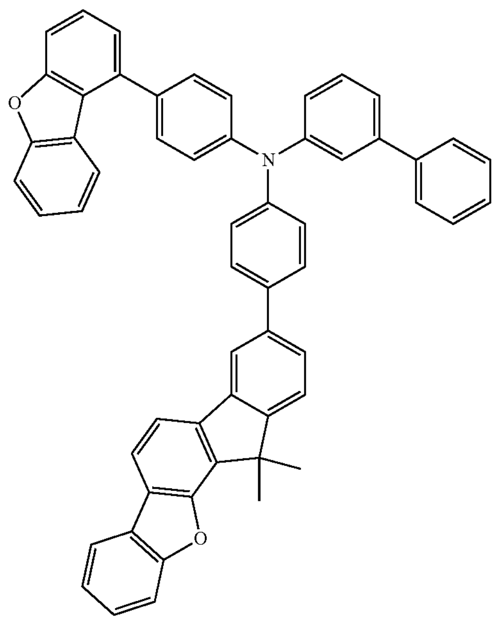
<Compound 104>
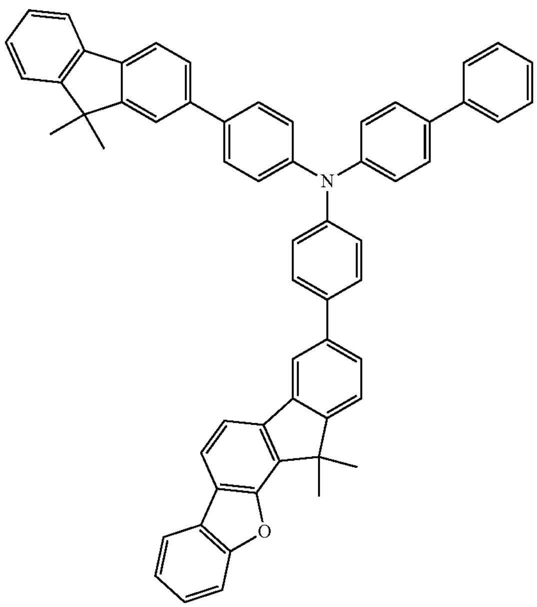

-continued
<Compound 105>
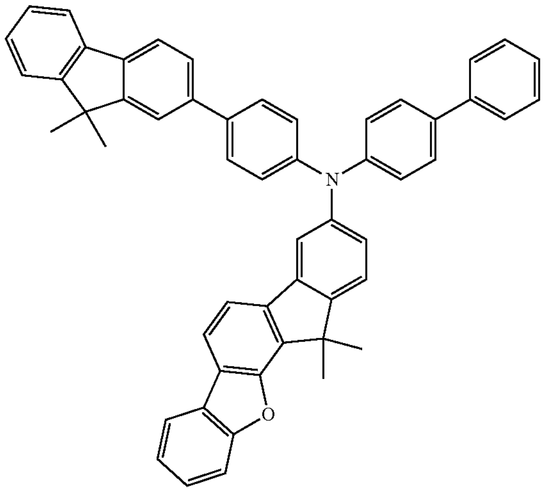
<Compound 106>
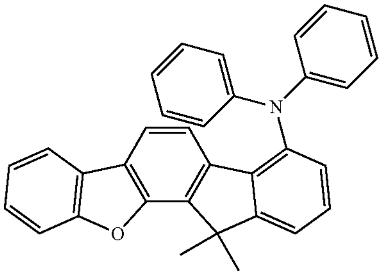
<Compound 107>
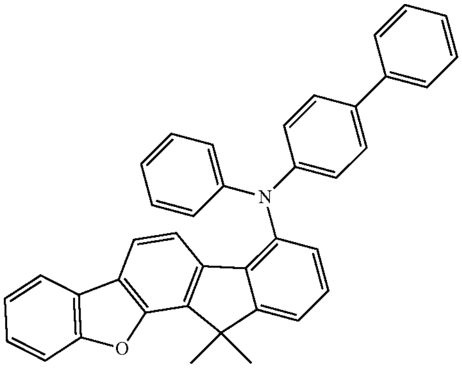
<Compound 108>
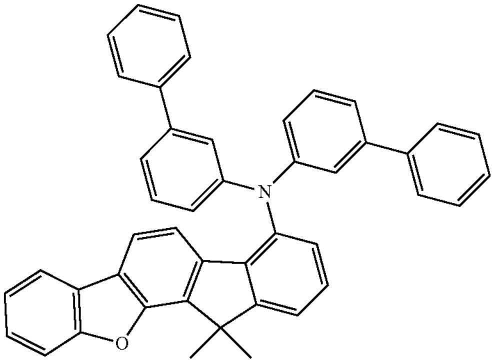
<Compound 109>
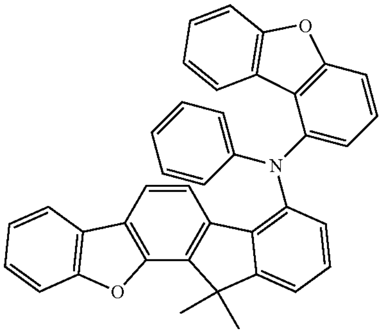
<Compound 110>
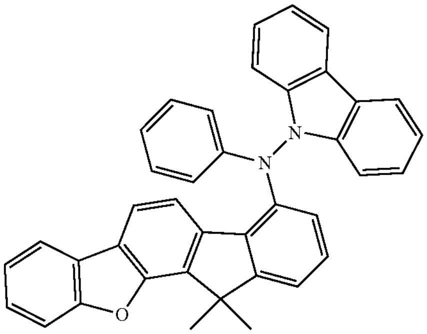

-continued
<Compound 111>
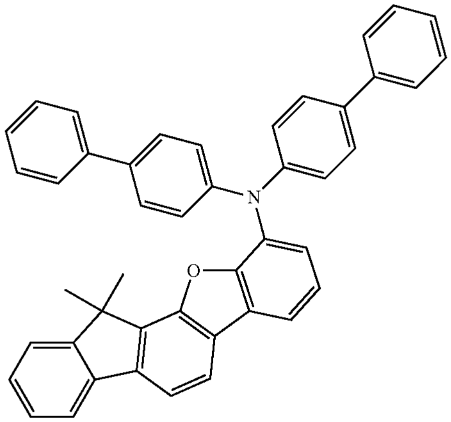
<Compound 112>
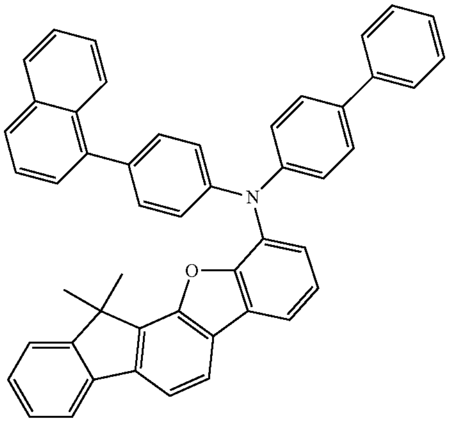
<Compound 113>
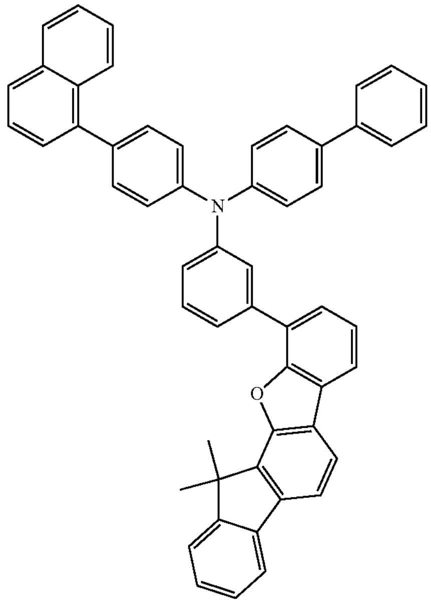
<Compound 114>
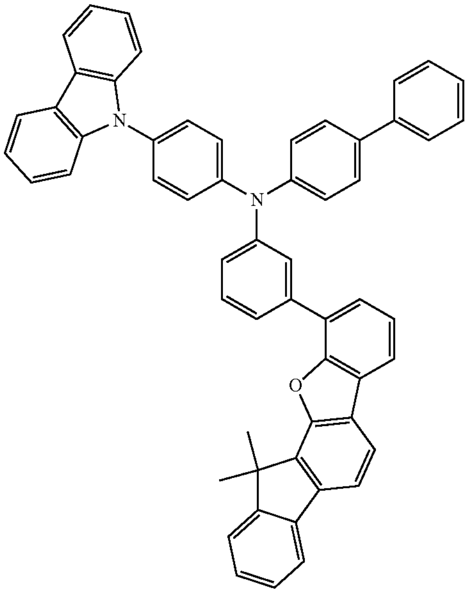

-continued
<Compound 115>
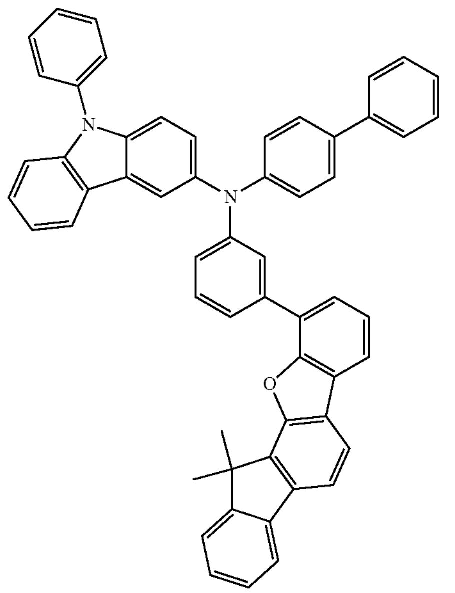
<Compound 116>
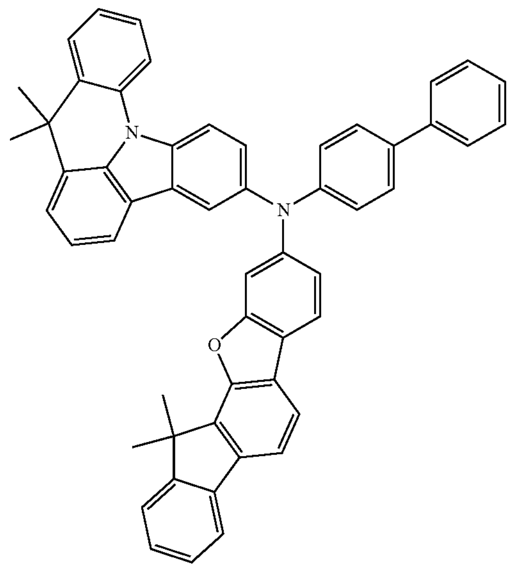
<Compound 117>
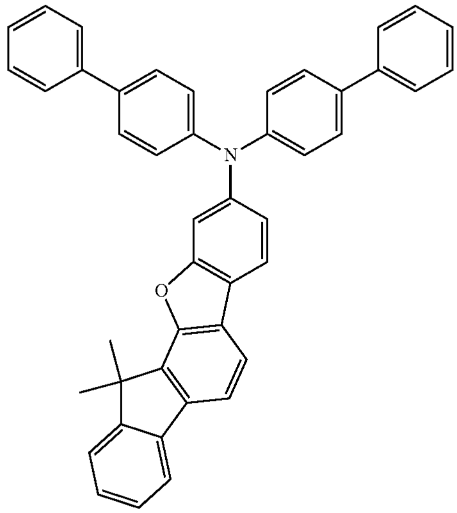
<Compound 118>
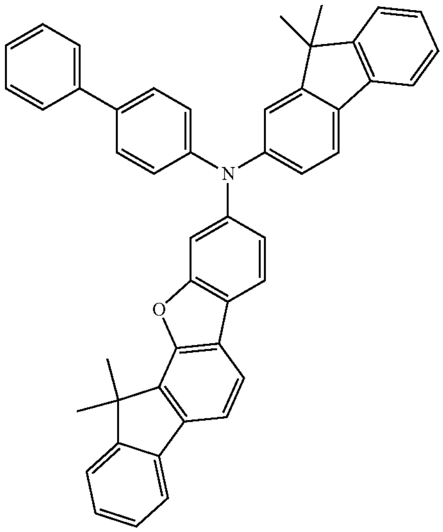

-continued
<Compound 119>
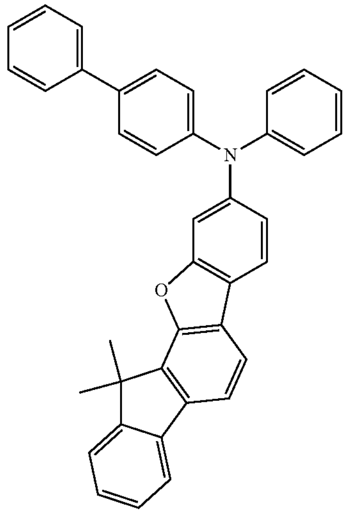
<Compound 120>
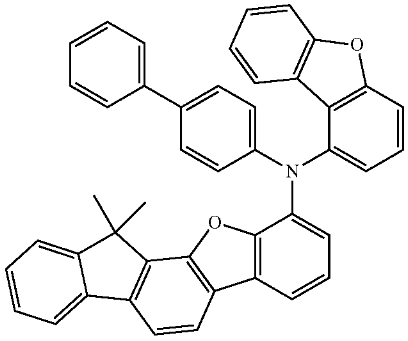
<Compound 121>
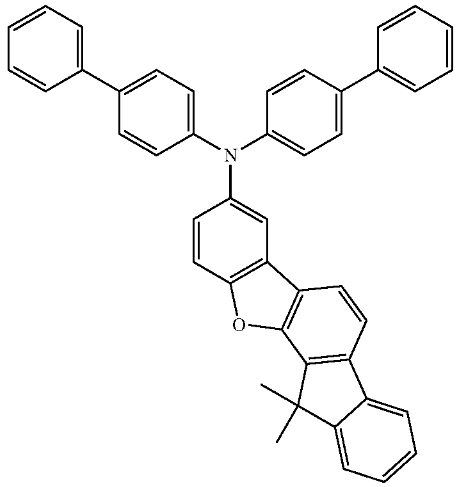
<Compound 122>
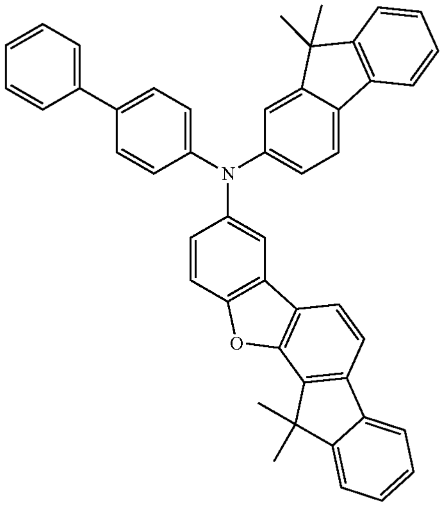
<Compound 123>
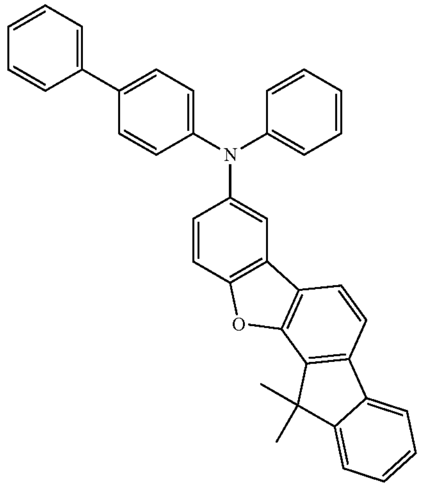
<Compound 124>
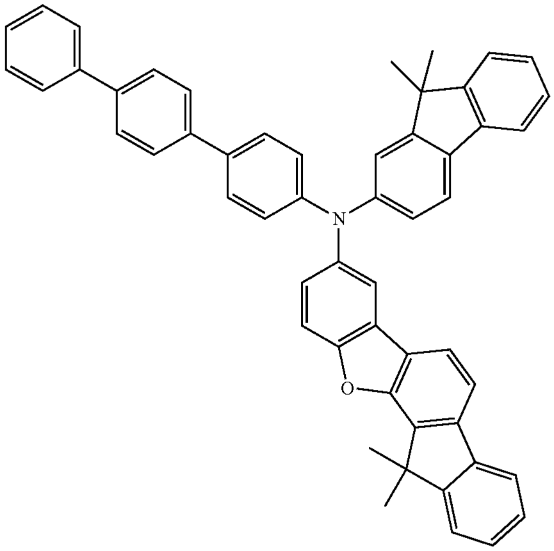

-continued
<Compound 125>
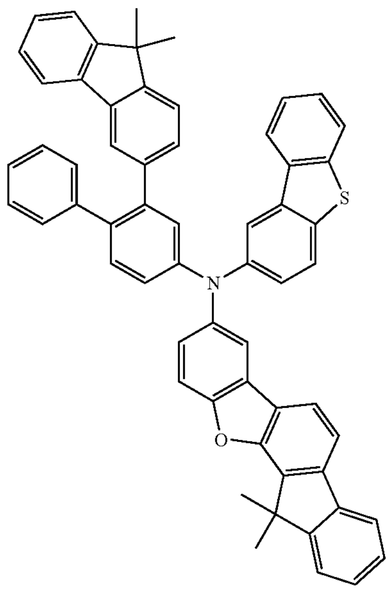
<Compound 126>
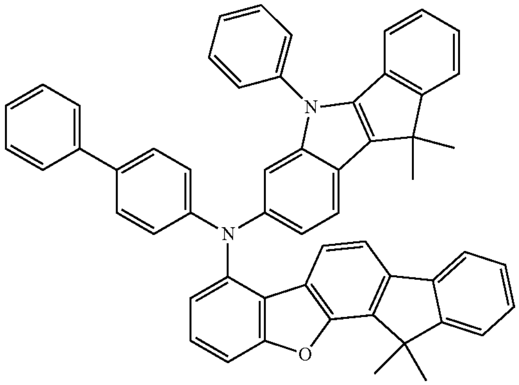
<Compound 127>
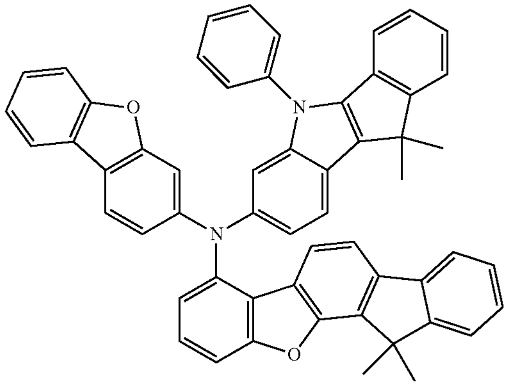
<Compound 128>
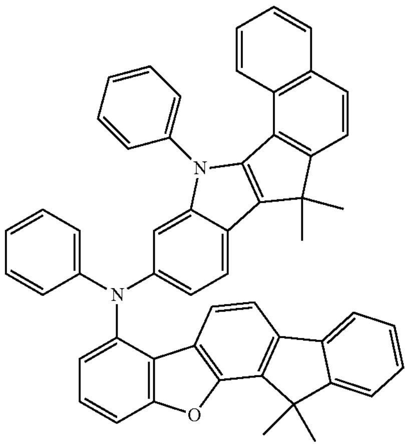
<Compound 129>
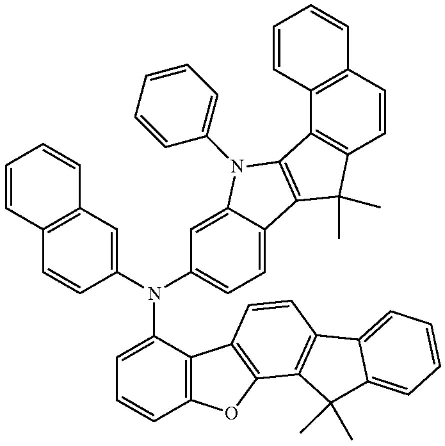
<Compound 130>
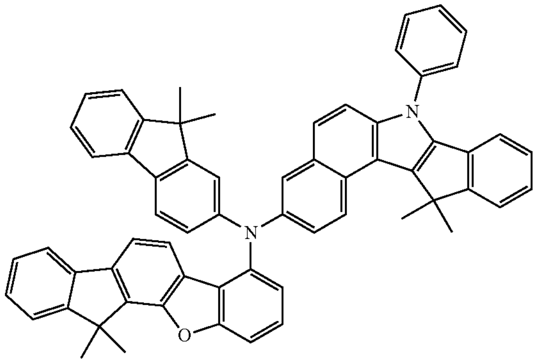

-continued
<Compound 131>
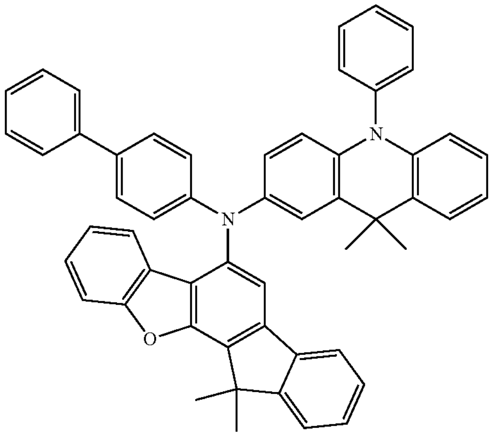
<Compound 132>
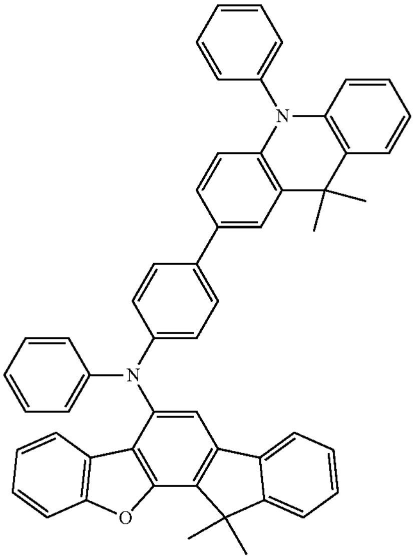
<Compound 133>
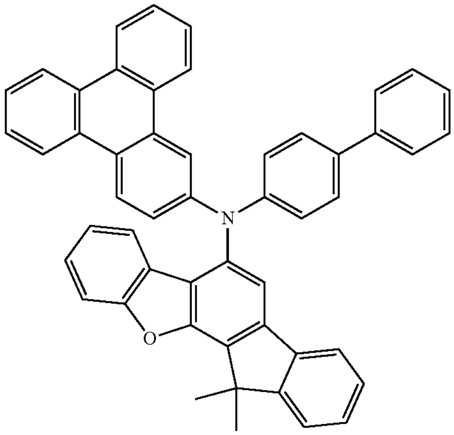
<Compound 134>
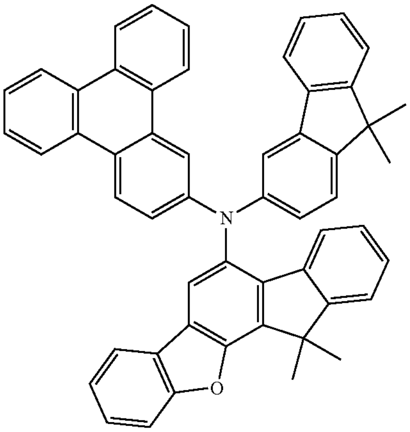
<Compound 135>
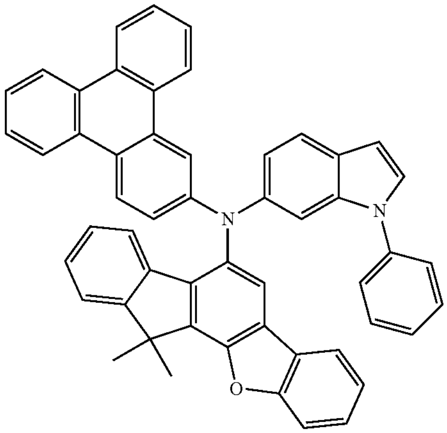
<Compound 136>
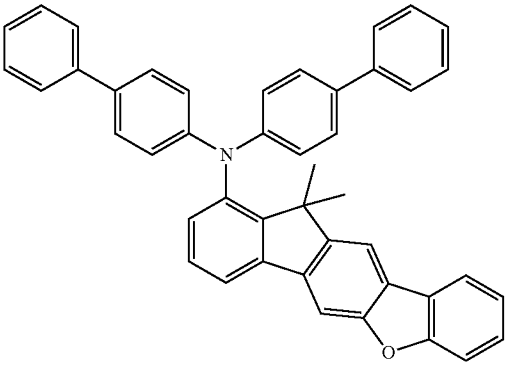

-continued
<Compound 137>
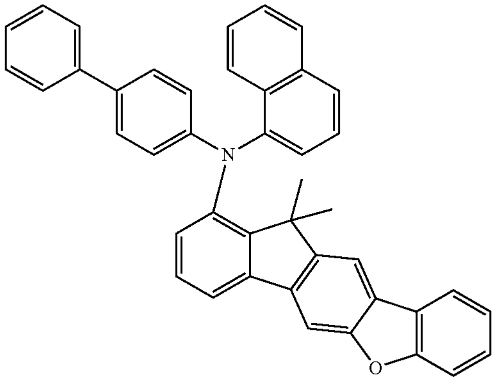
<Compound 138>
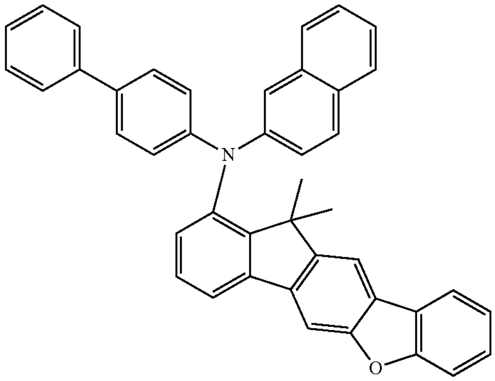
<Compound 139>
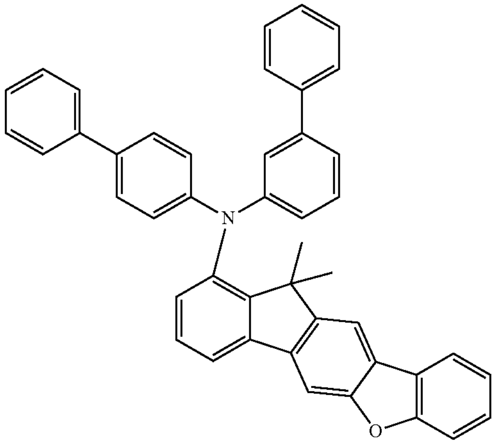
<Compound 140>
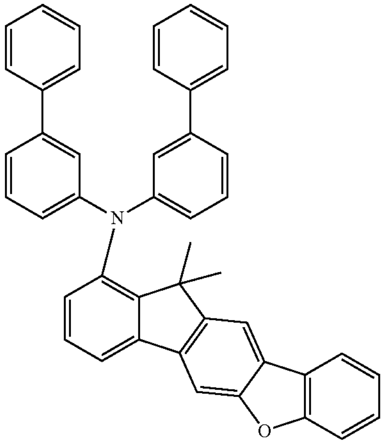
<Compound 141>
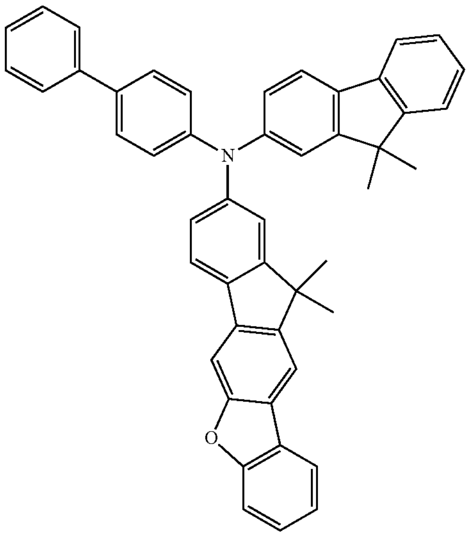
<Compound 142>
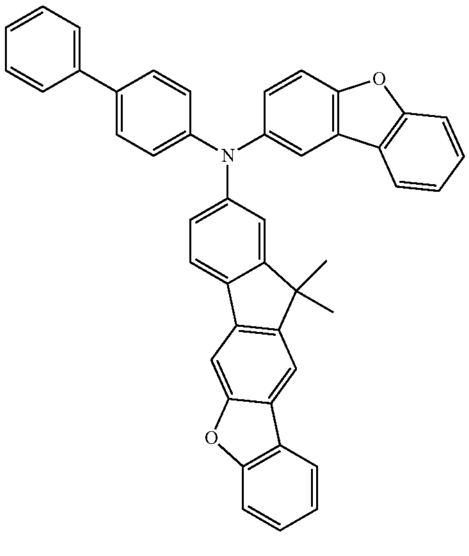

-continued
<Compound 143>
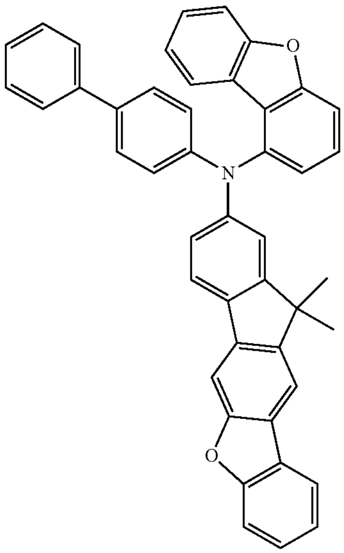
<Compound 144>
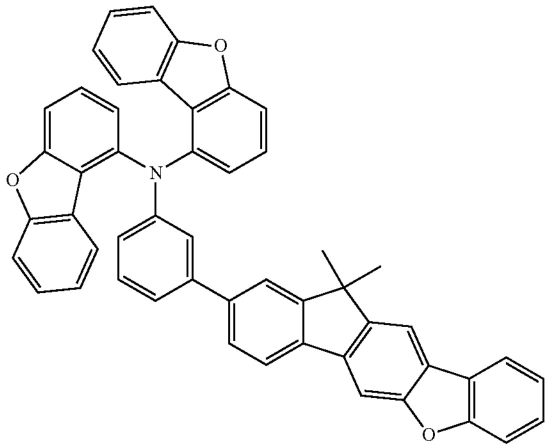
<Compound 145>
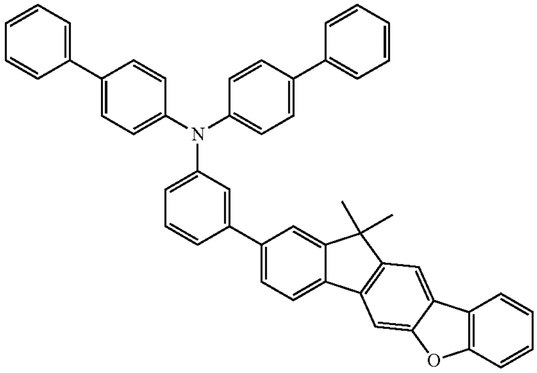
<Compound 146>
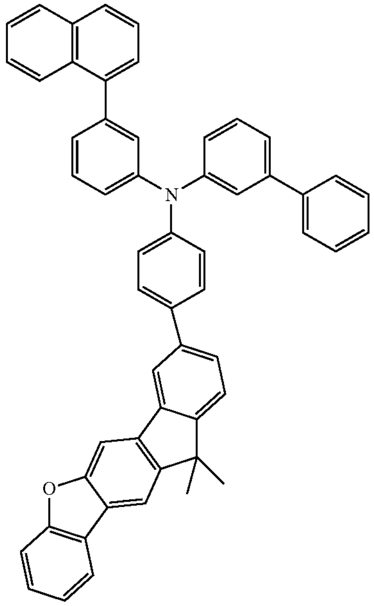

-continued
<Compound 147>
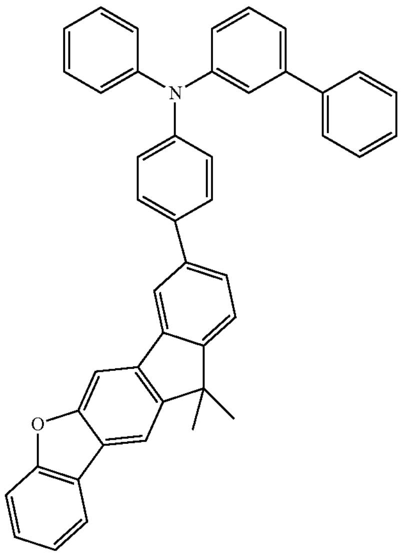
<Compound 148>
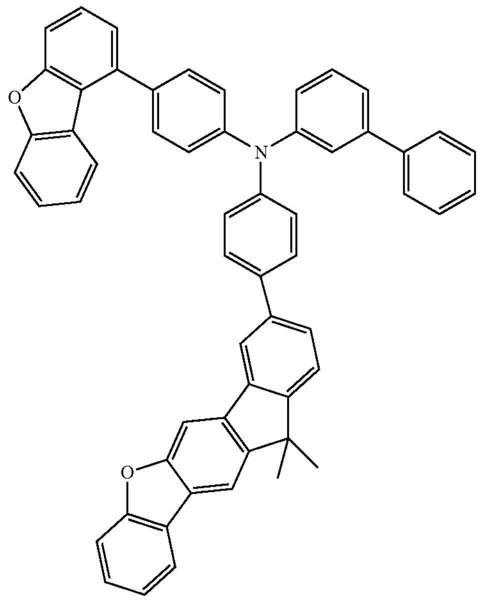
<Compound 149>
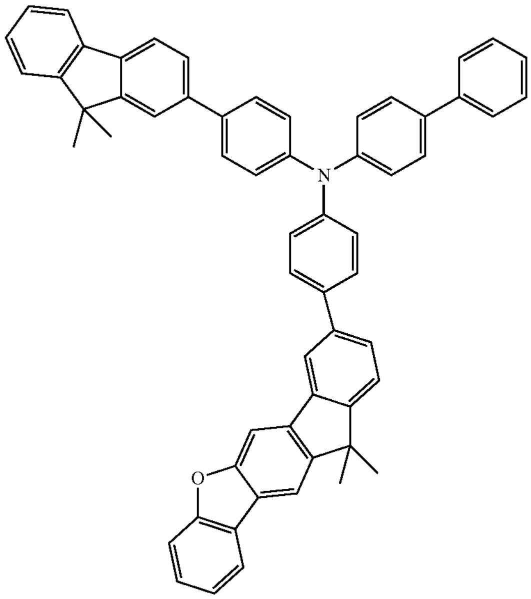
<Compound 150>
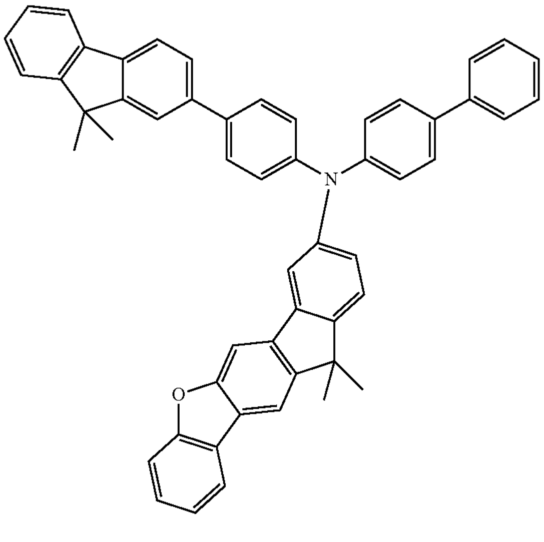
<Compound 151>
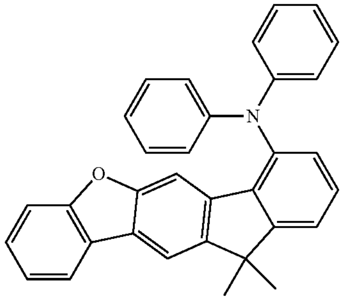
<Compound 152>
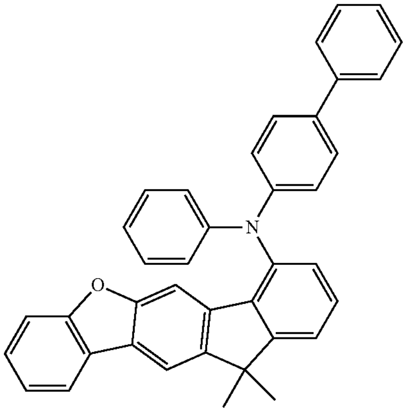

-continued
<Compound 153>
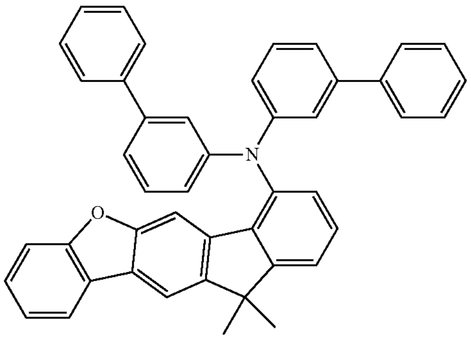
<Compound 154>
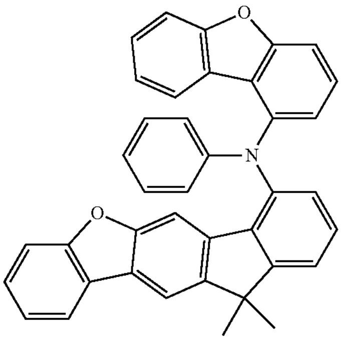
<Compound 155>
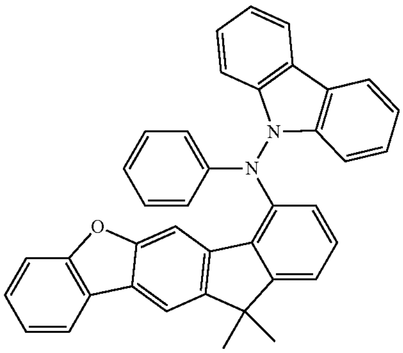
<Compound 156>
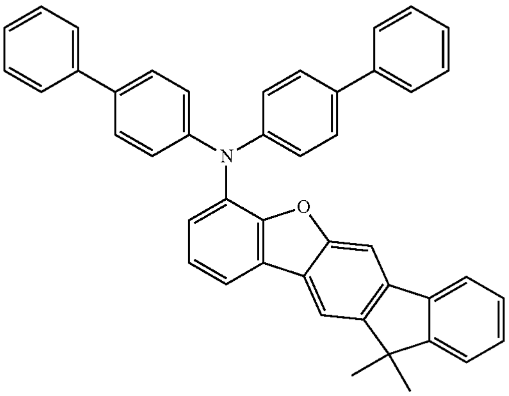
<Compound 157>
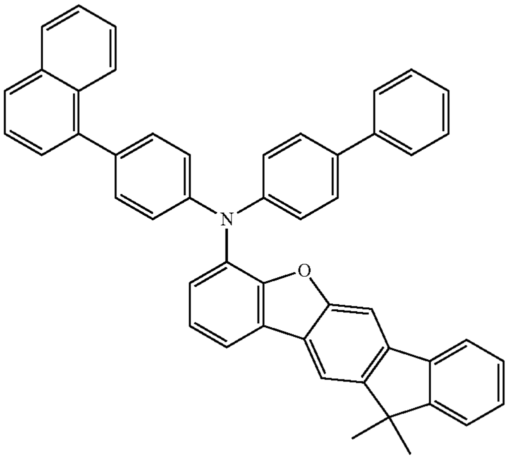
<Compound 158>
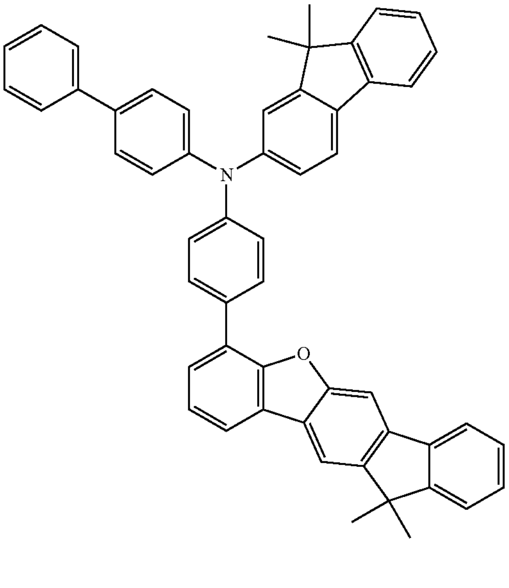

-continued
<Compound 159>
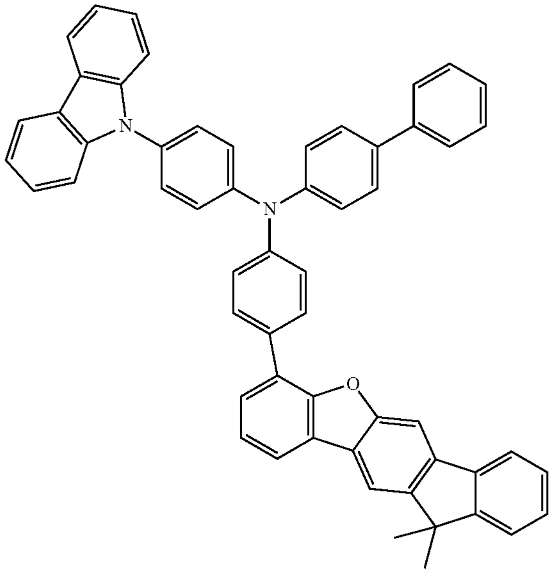
<Compound 160>
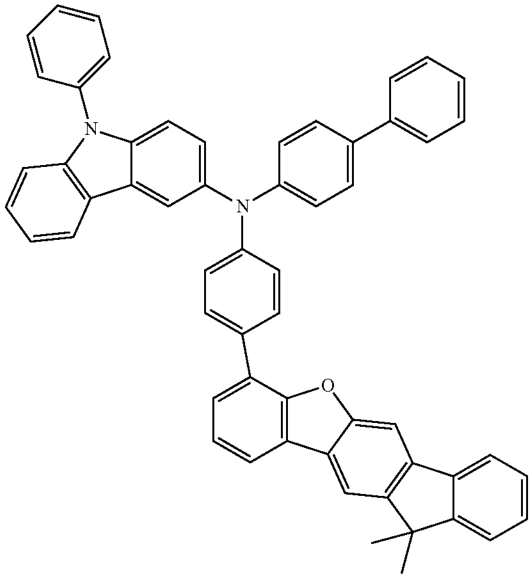
<Compound 161>
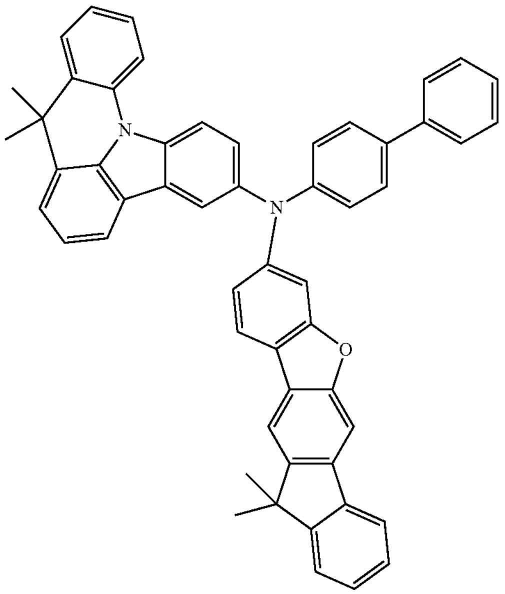
<Compound 162>
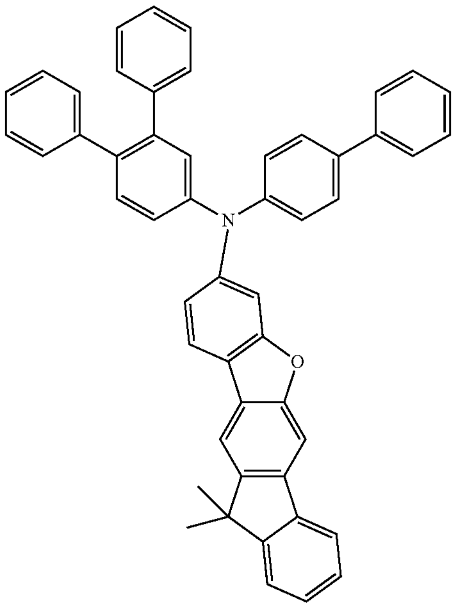

-continued
<Compound 163>
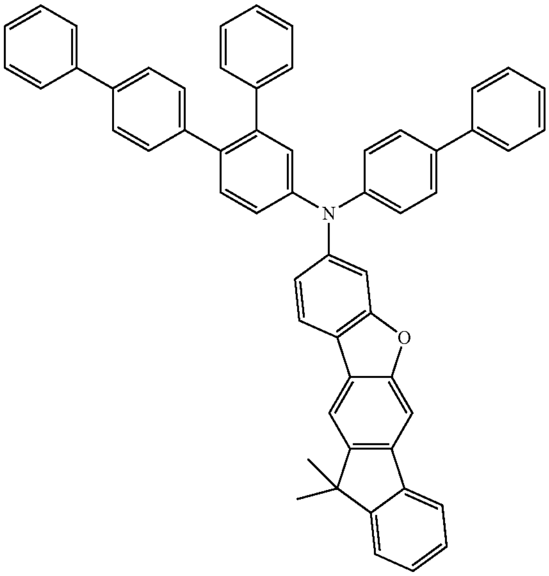
<Compound 164>
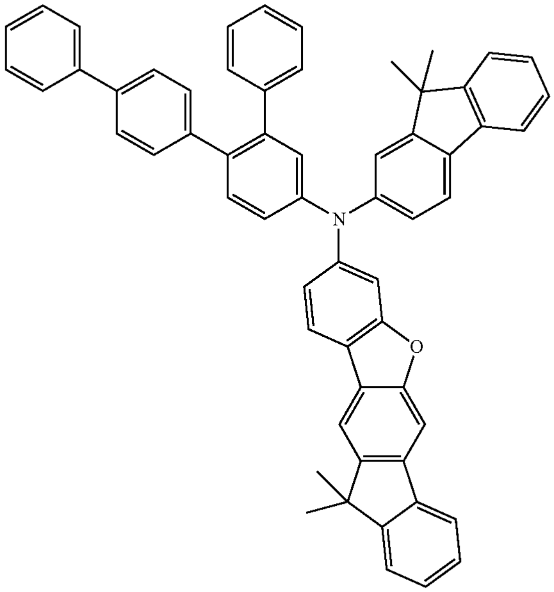
<Compound 165>
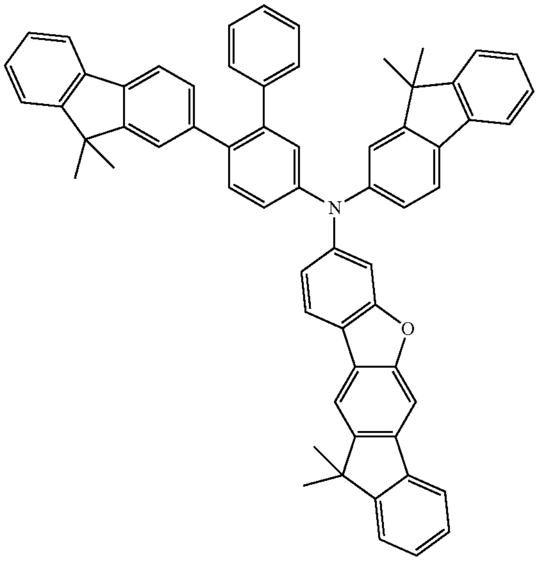
<Compound 166>
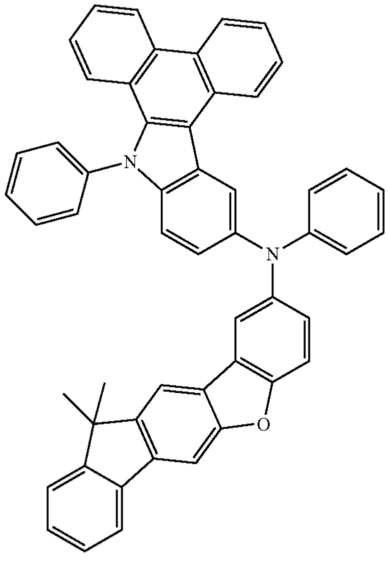

-continued
<Compound 167>
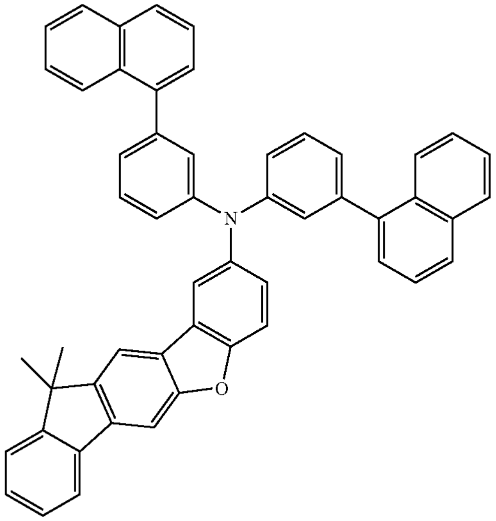
<Compound 168>
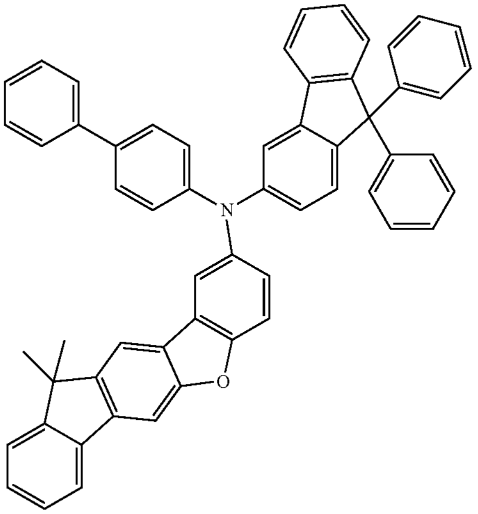
<Compound 169>
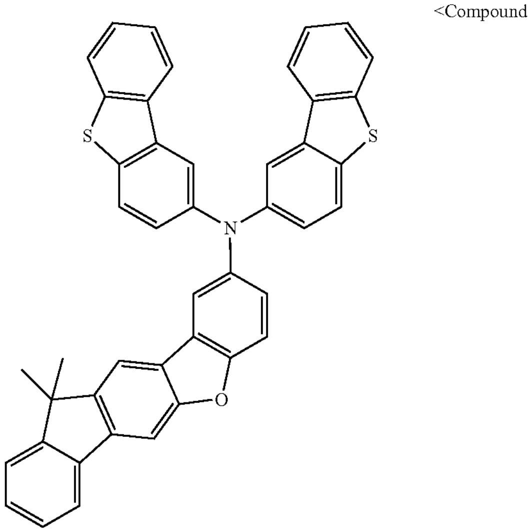
<Compound 170>
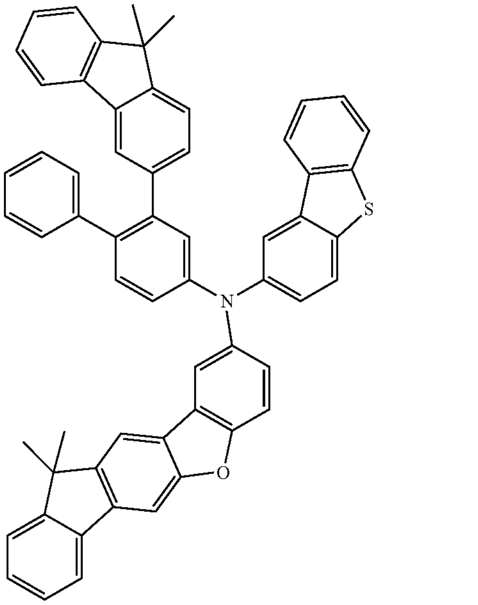
<Compound 171>
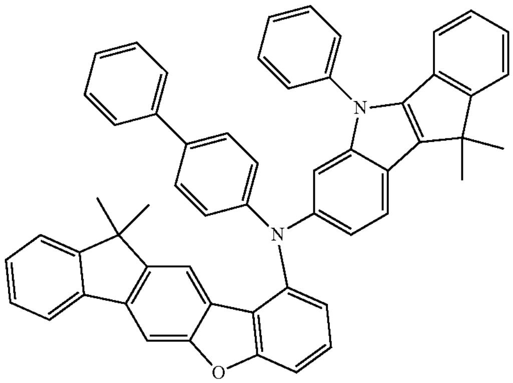
<Compound 172>
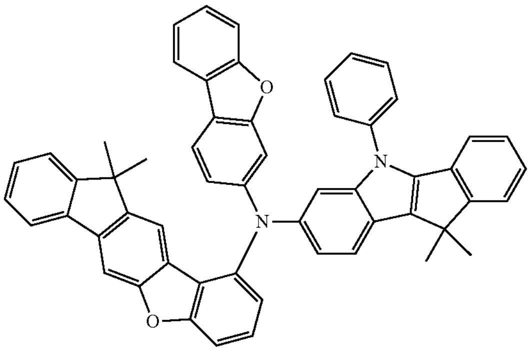

-continued
<Compound 173>
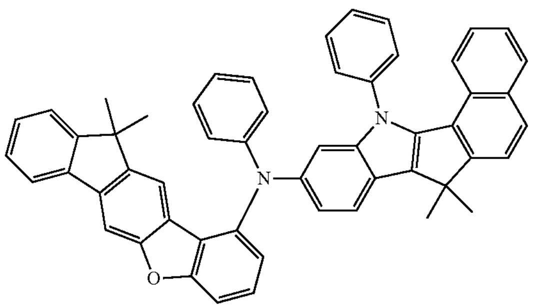
<Compound 174>
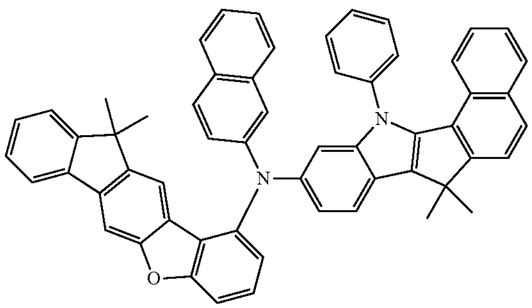
<Compound 175>
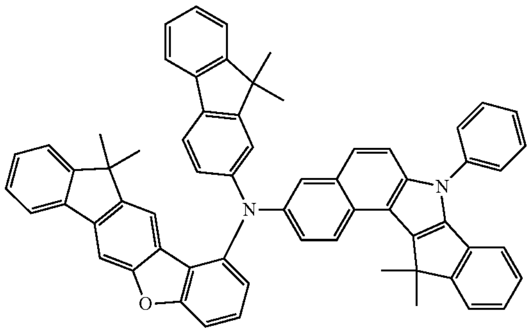
<Compound 176>
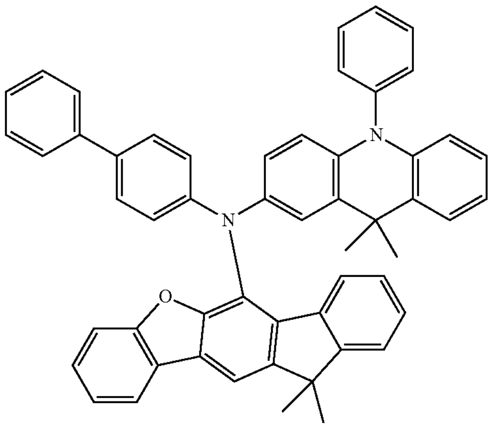
<Compound 177>
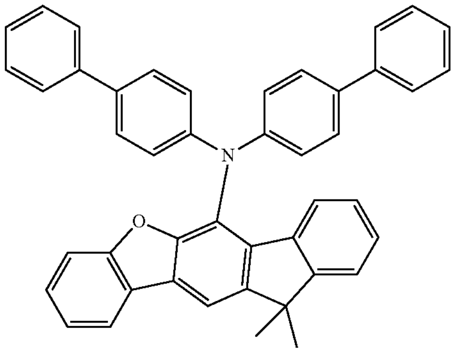
<Compound 178>
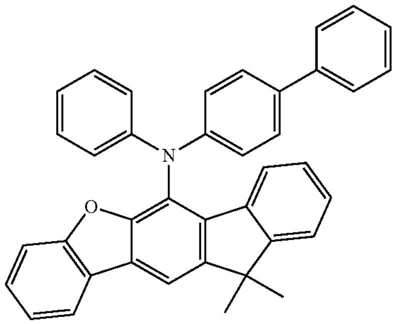
<Compound 179>
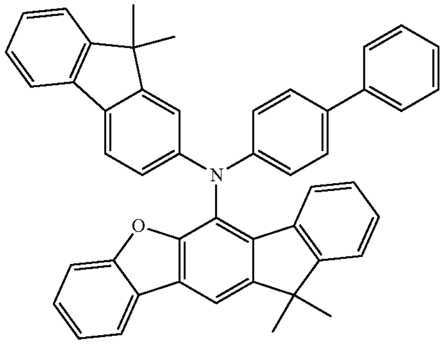
<Compound 180>
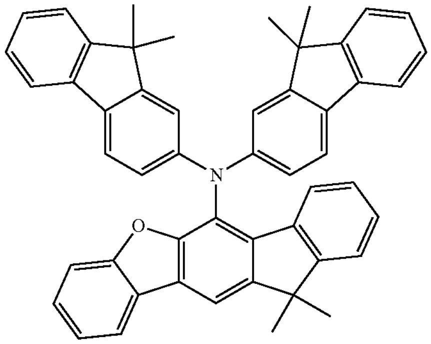

-continued
<Compound 181>
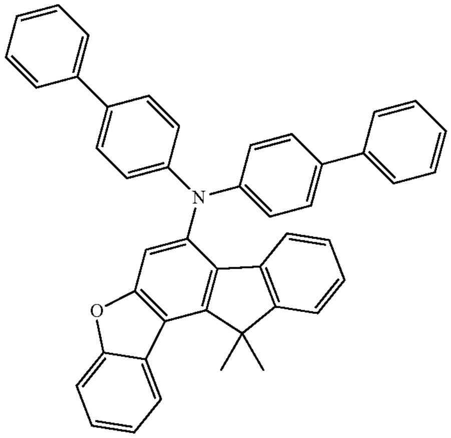
<Compound 182>
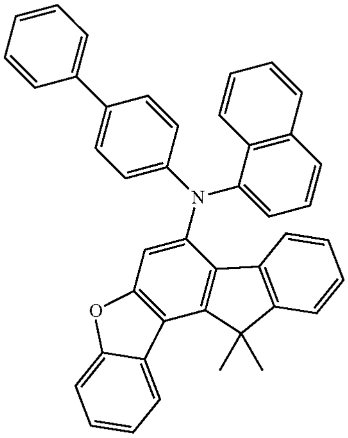
<Compound 183>
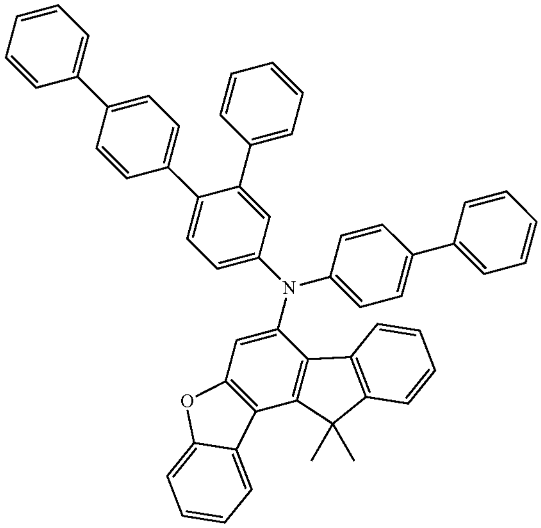
<Compound 184>
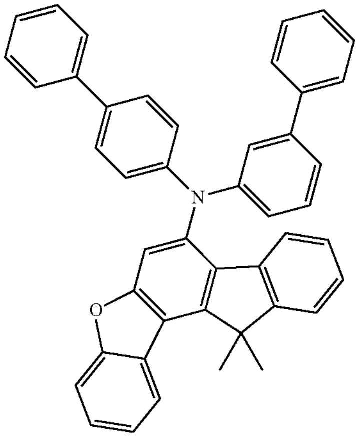
<Compound 185>
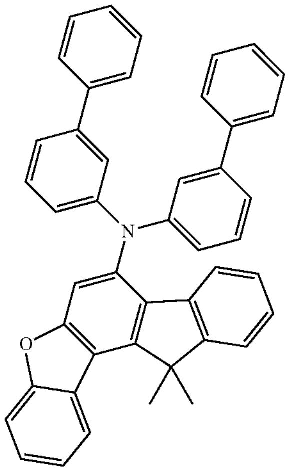
<Compound 186>
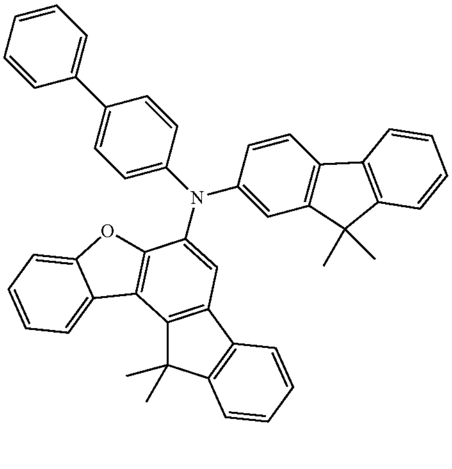

-continued
<Compound 187>
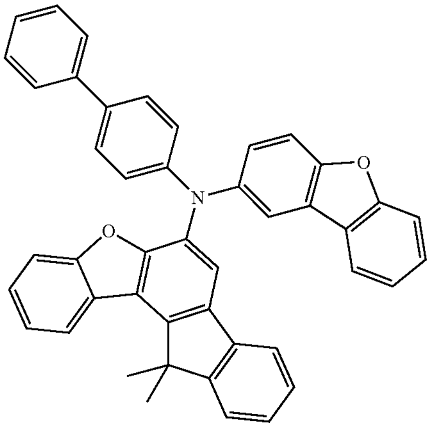
<Compound 188>
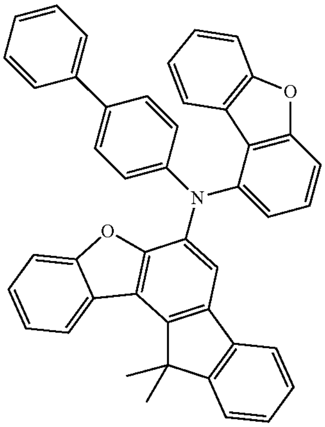
<Compound 189>
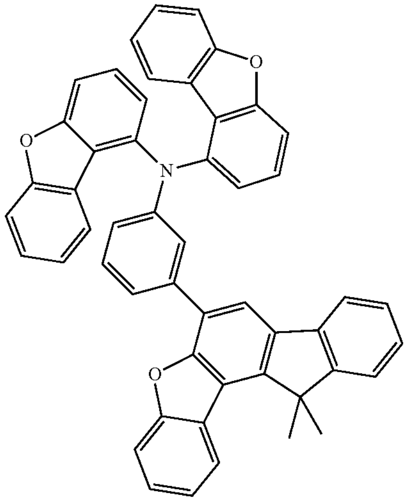
<Compound 190>
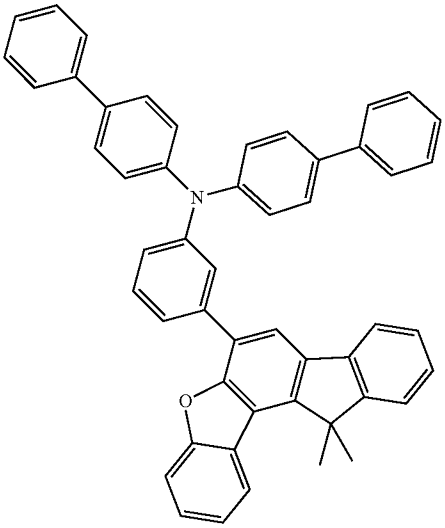
<Compound 191>
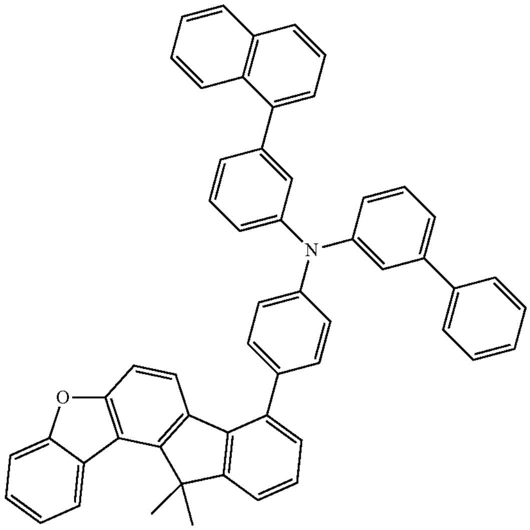
<Compound 192>
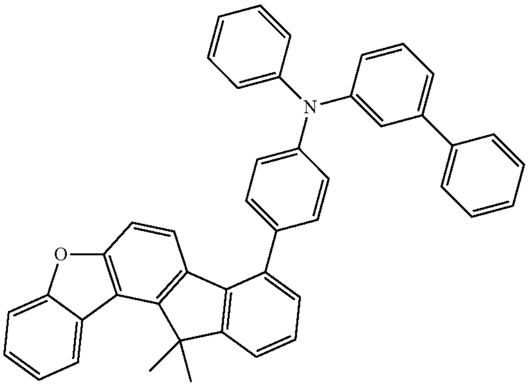

-continued
<Compound 193>
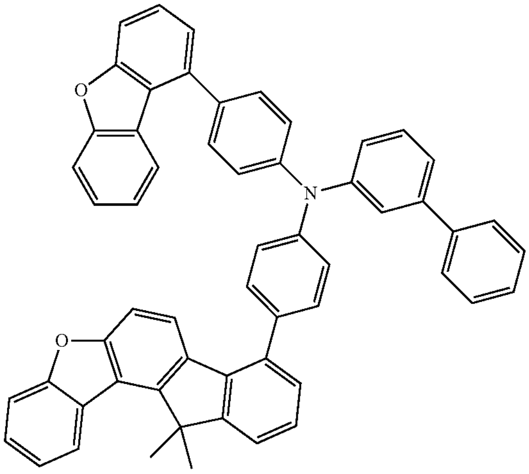
<Compound 194>
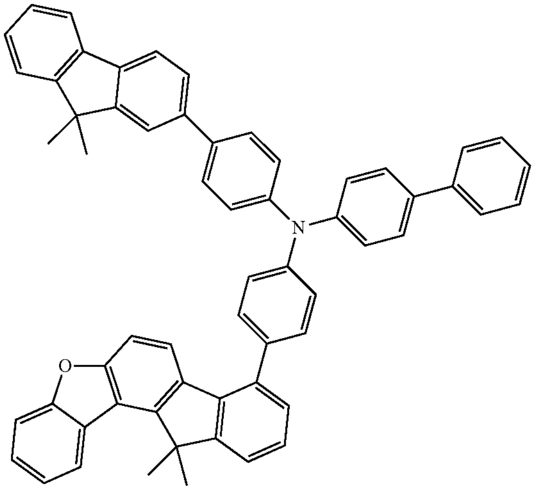
<Compound 195>
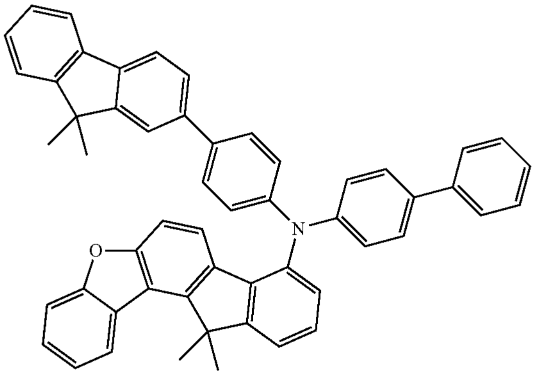
<Compound 196>
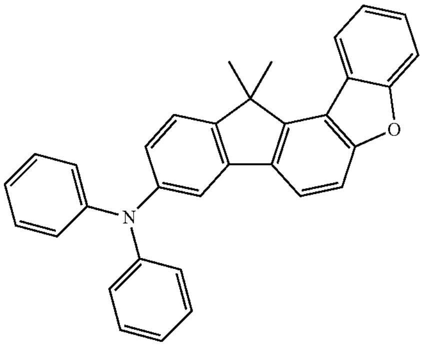
<Compound 197>
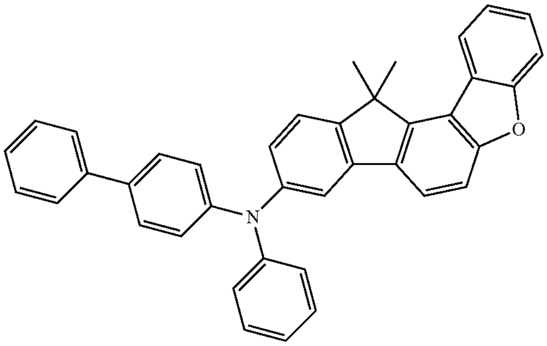
<Compound 198>
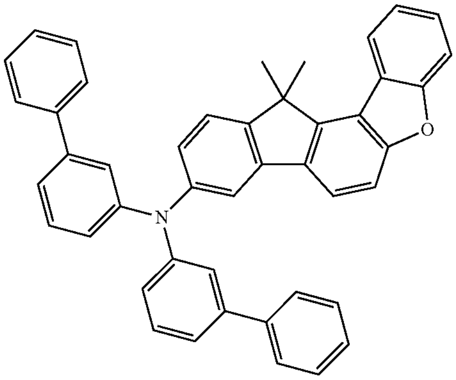

-continued
<Compound 199>
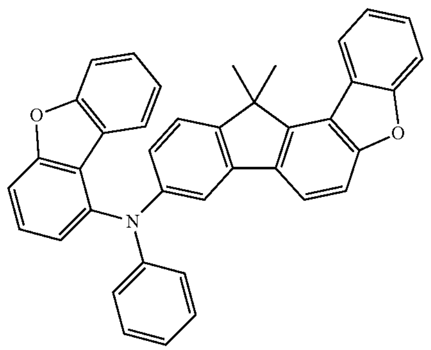
<Compound 200>
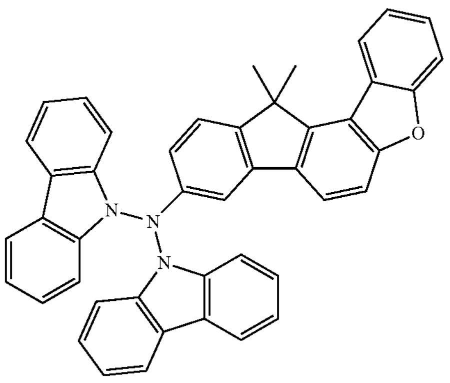
<Compound 201>
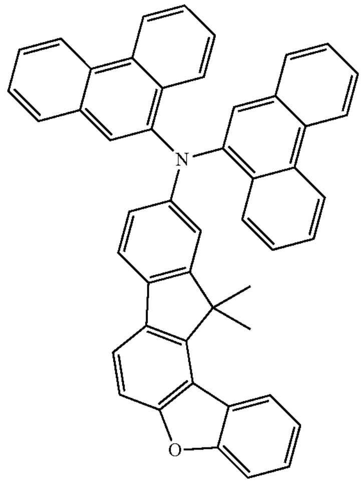
<Compound 202>
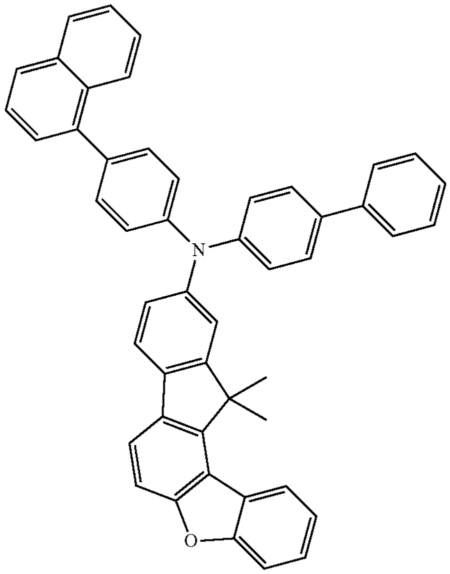
<Compound 203>
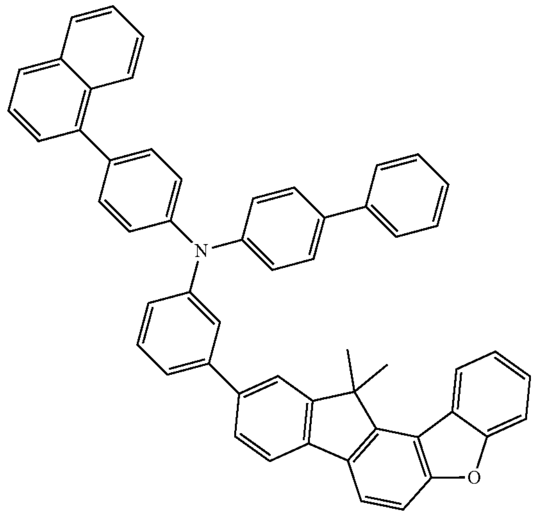
<Compound 204>
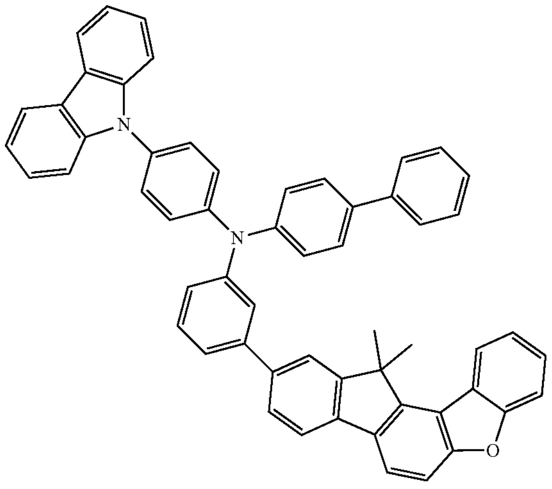

-continued
<Compound 205>
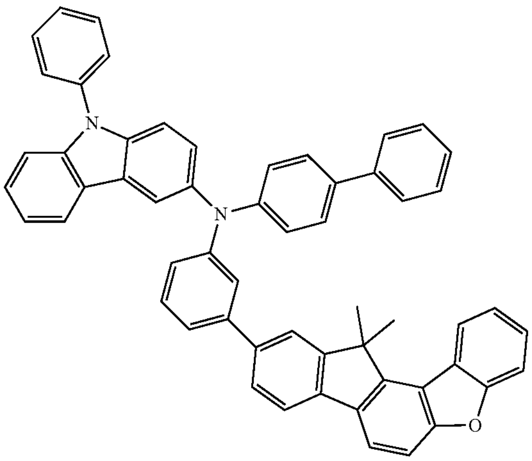
<Compound 206>
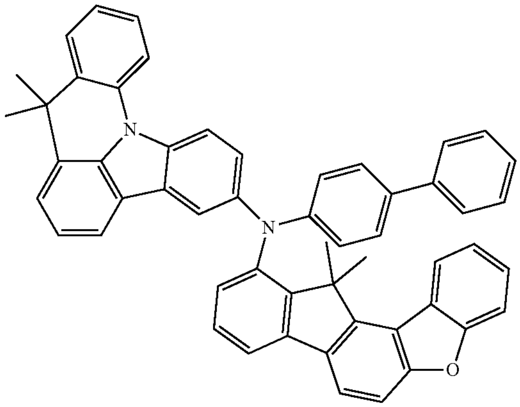
<Compound 207>
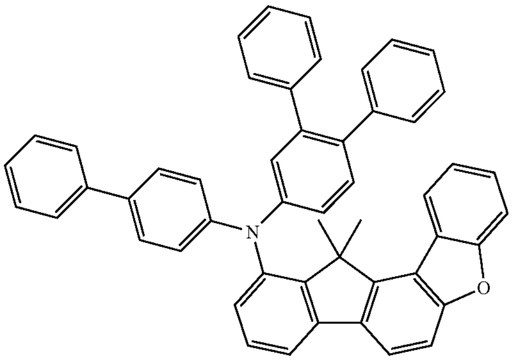
<Compound 208>
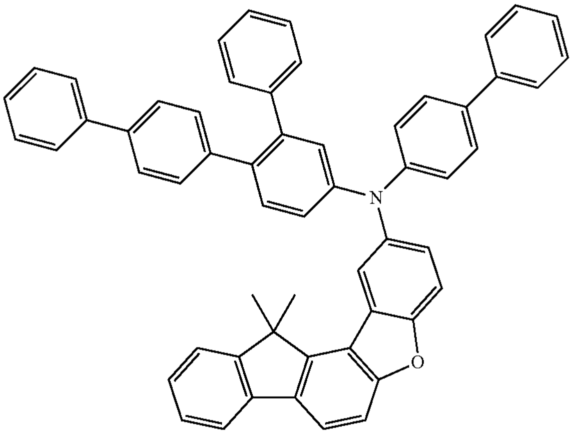
<Compound 209>
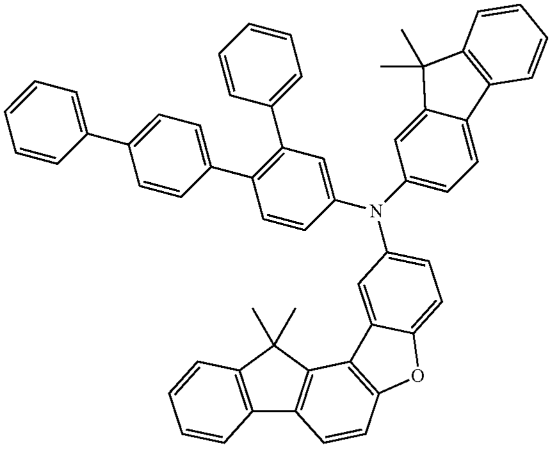
<Compound 210>
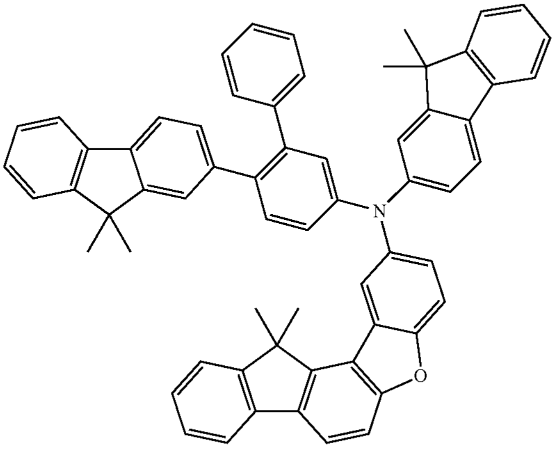

-continued
<Compound 211>
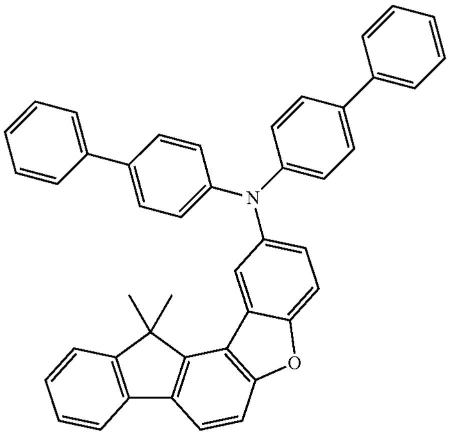
<Compound 212>
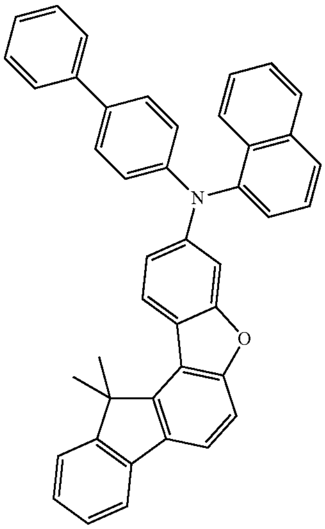
<Compound 213>
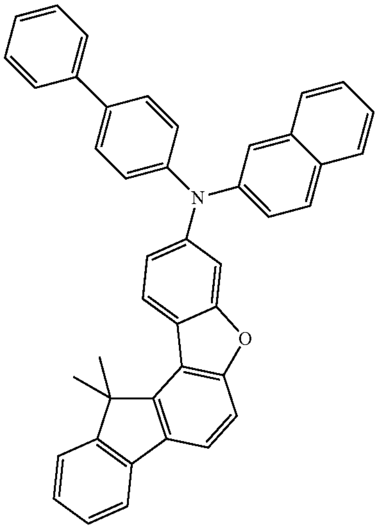
<Compound 214>
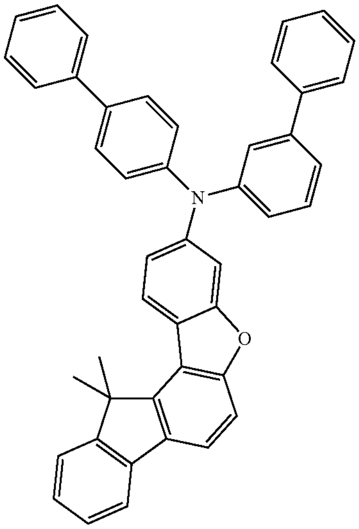
<Compound 215>
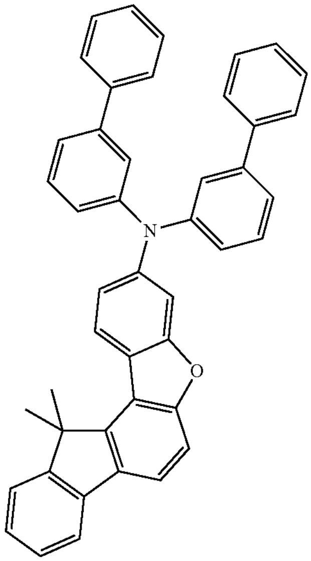
<Compound 216>
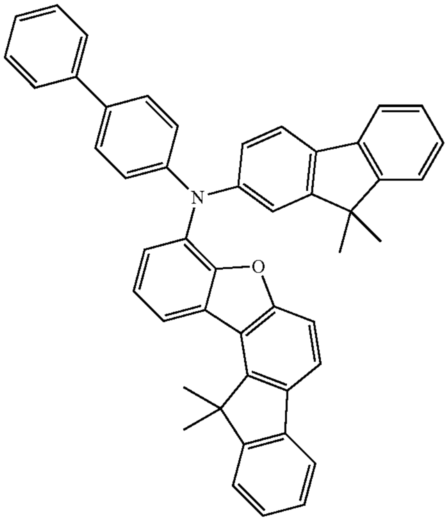

-continued
<Compound 217>
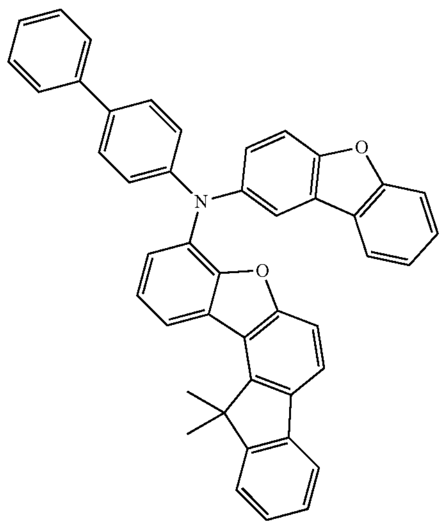
<Compound 218>
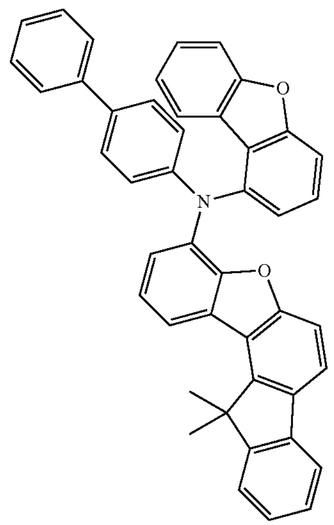
<Compound 219>
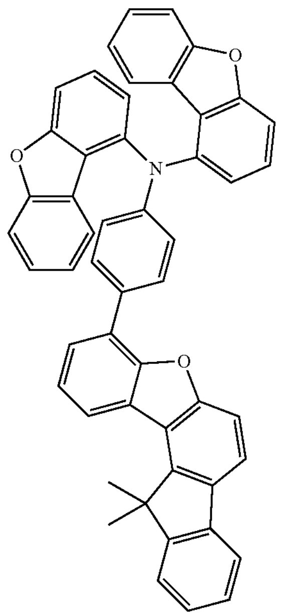
<Compound 220>
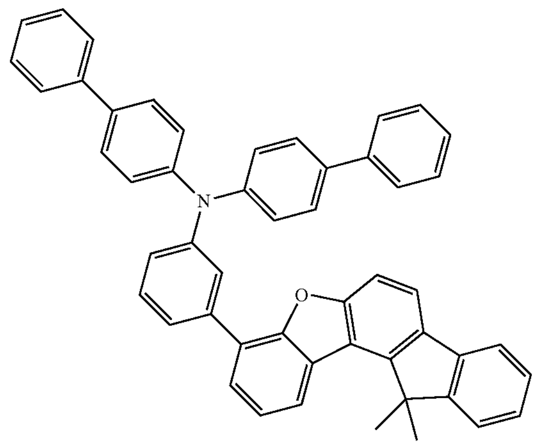
<Compound 221>
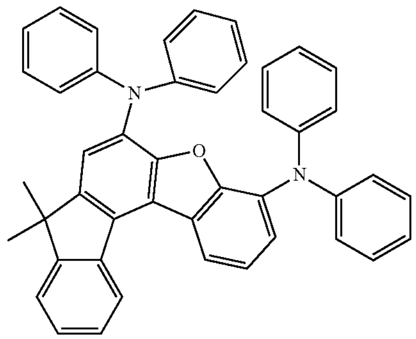
<Compound 222>
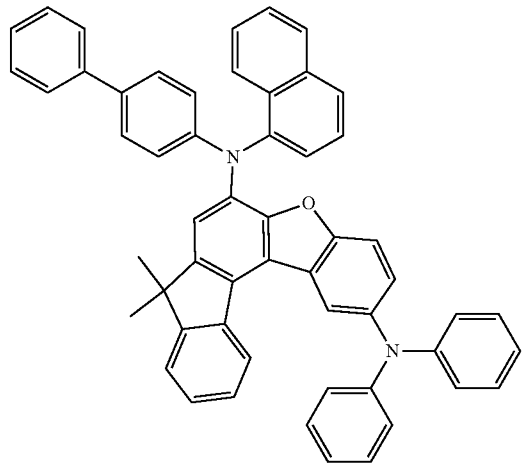

-continued
<Compound 223>
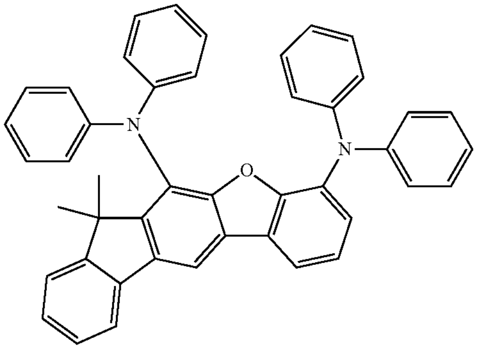
<Compound 224>
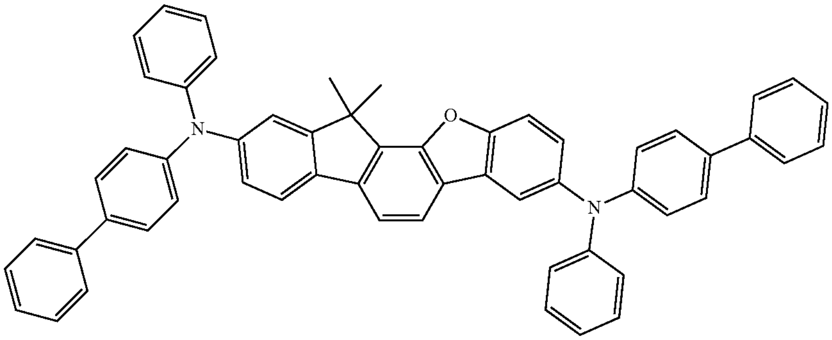
<Compound 225>
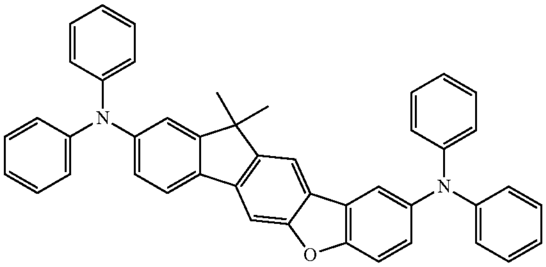
<Compound 226>
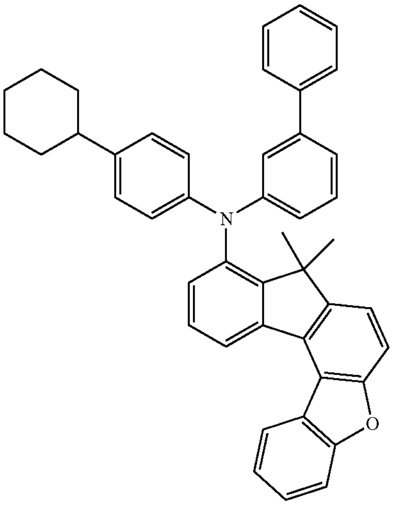

-continued
<Compound 227>
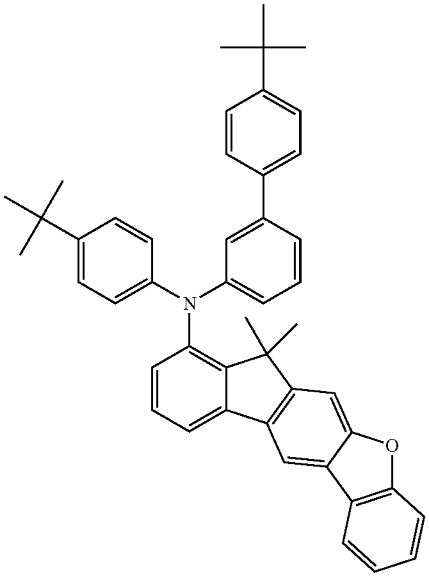
<Compound 228>
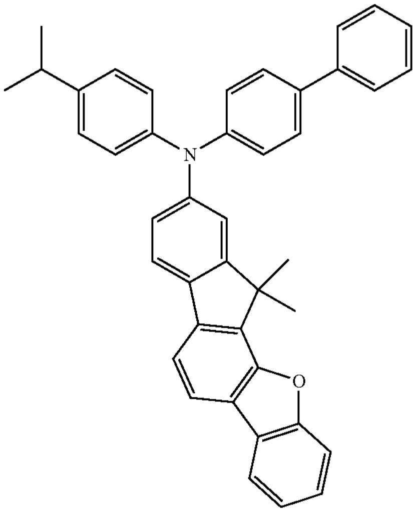
<Compound 229>
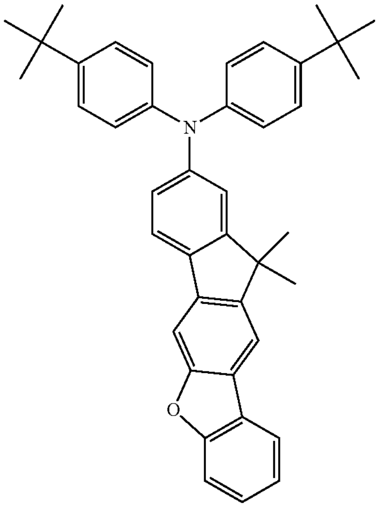
<Compound 230>
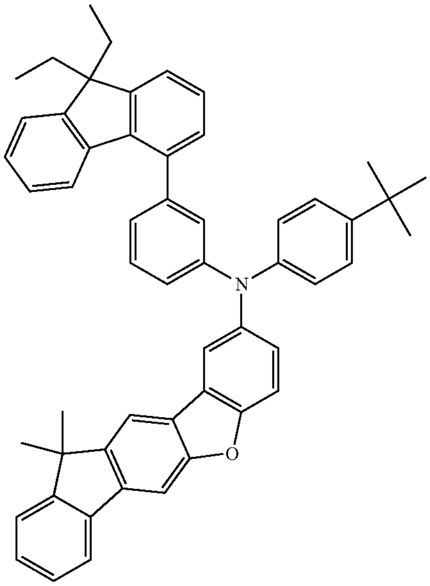
<Compound 231>
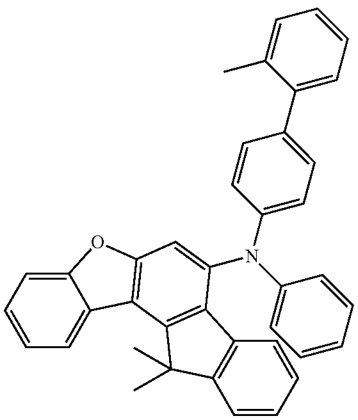
<Compound 232>
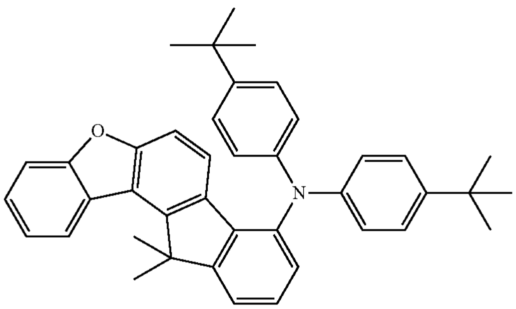

-continued
<Compound 233>
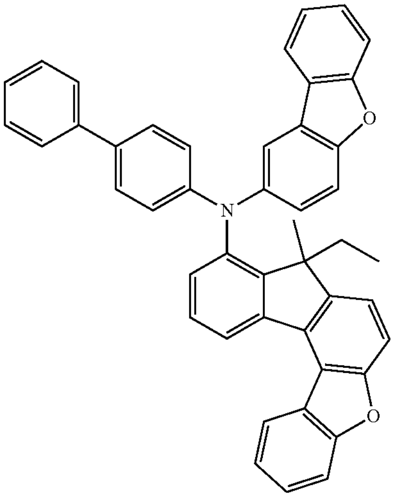
<Compound 234>
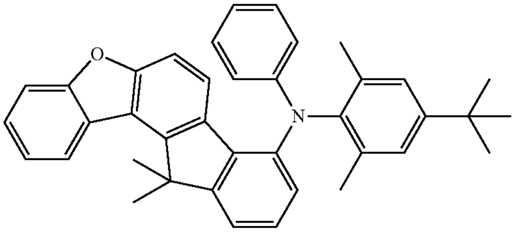
<Compound 235>
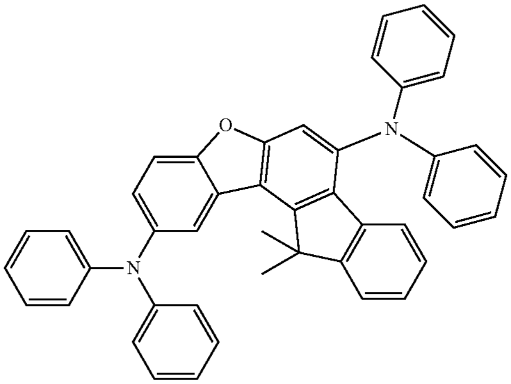
<Compound 236>
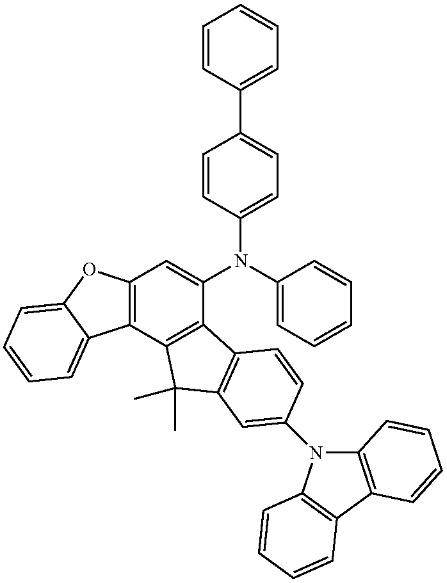
<Compound 237>
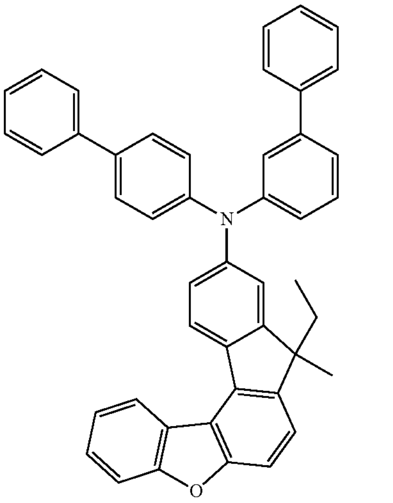
<Compound 238>
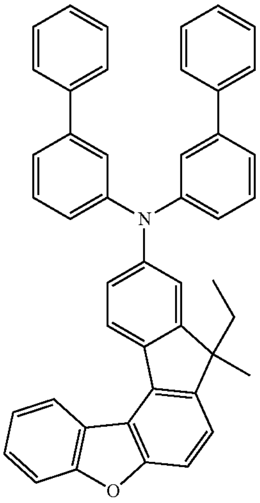

-continued
<Compound 239>
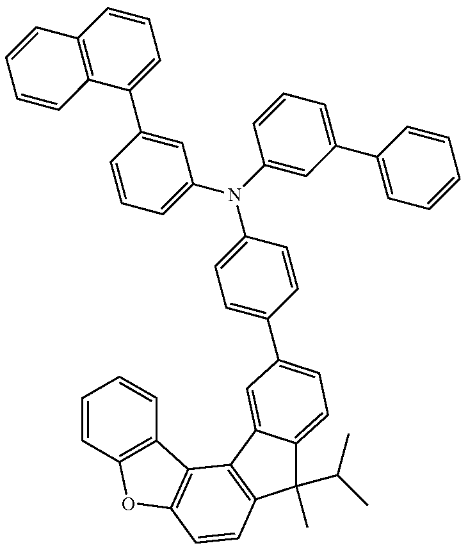
<Compound 240>
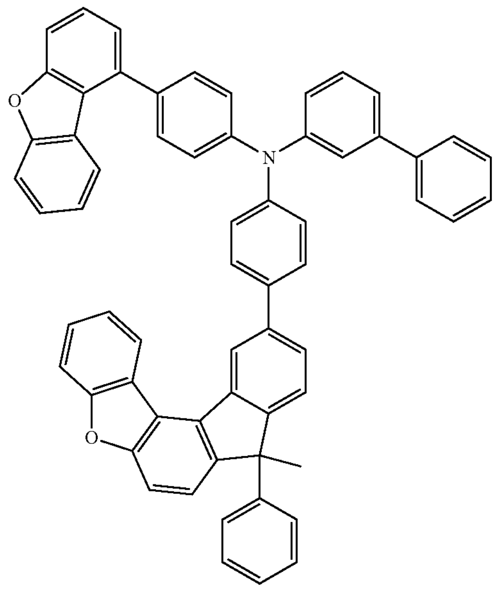
<Compound 241>
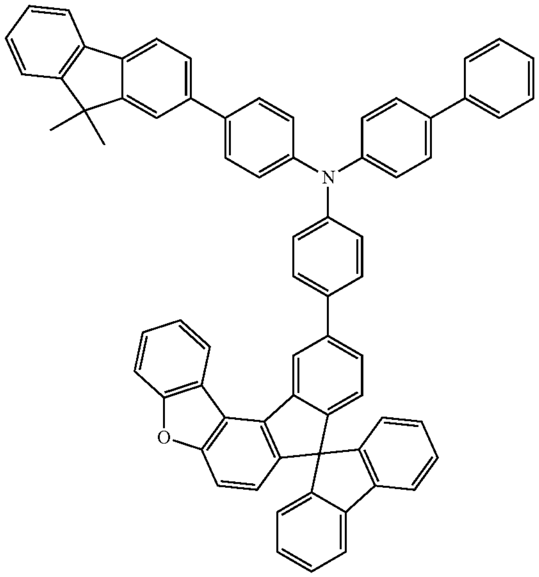
<Compound 242>
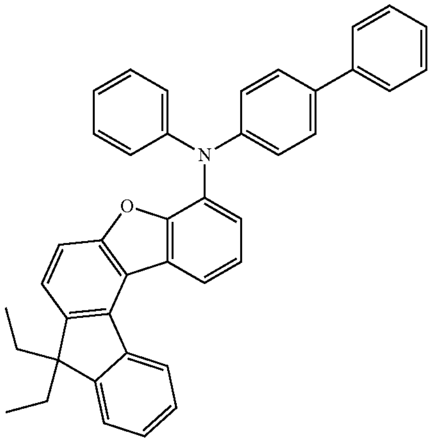

-continued
<Compound 243>
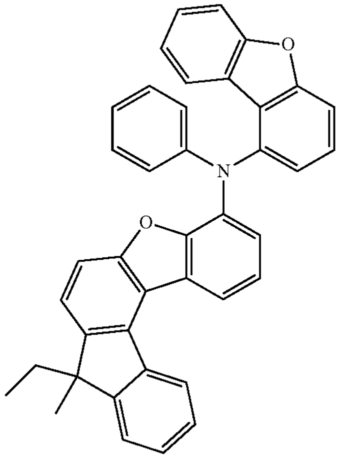
<Compound 244>
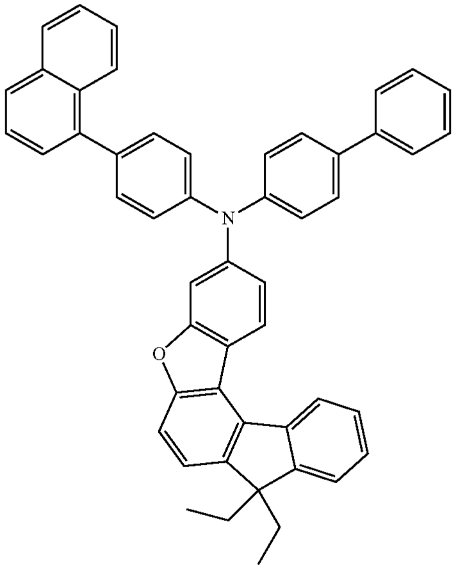
<Compound 245>
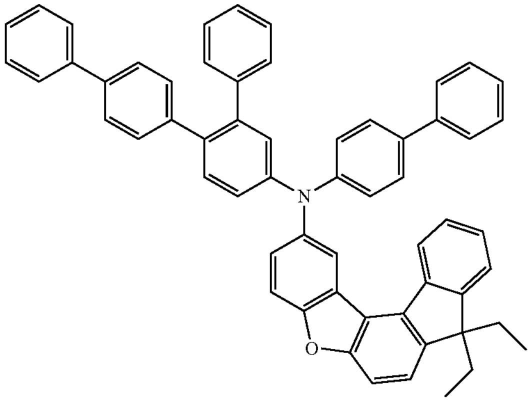
<Compound 246>
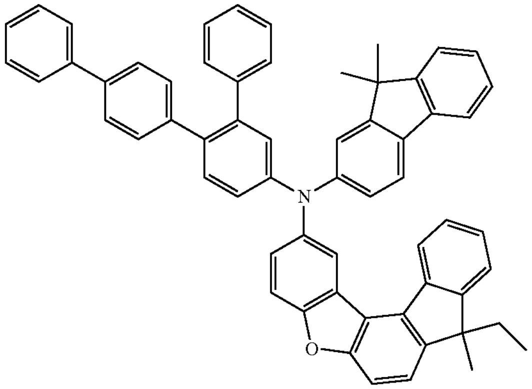
<Compound 247>
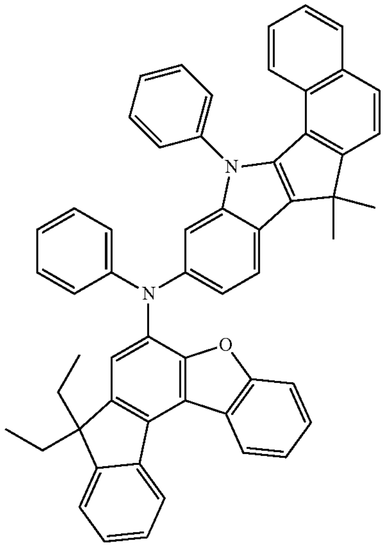
<Compound 248>
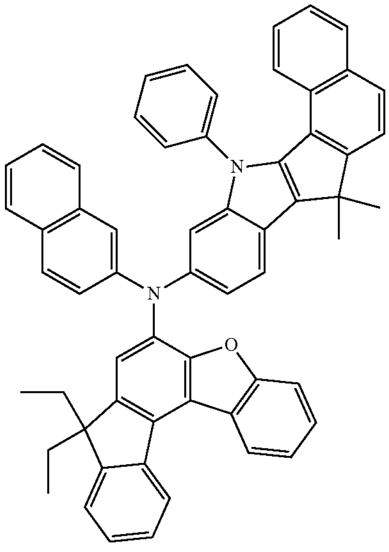

-continued
<Compound 249>
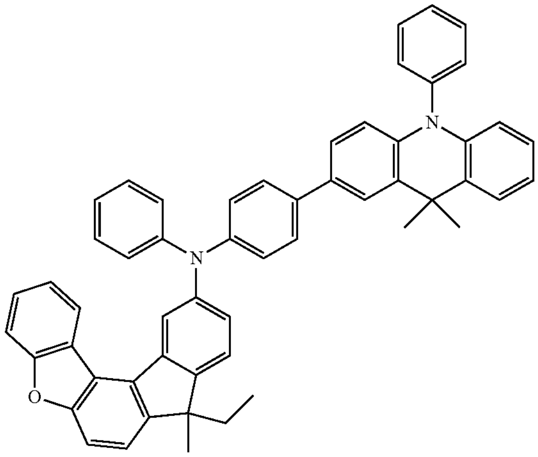
<Compound 250>
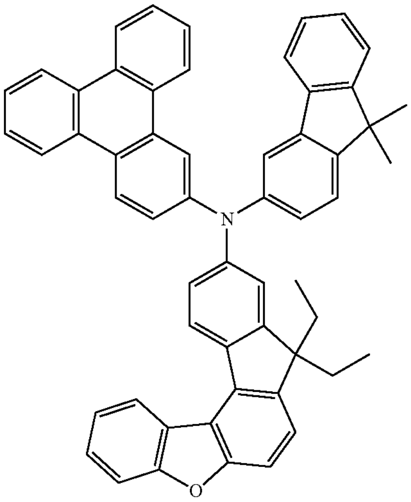
<Compound 251>
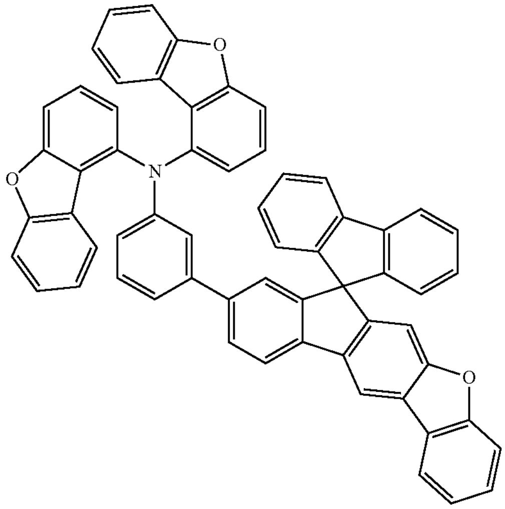
<Compound 252>
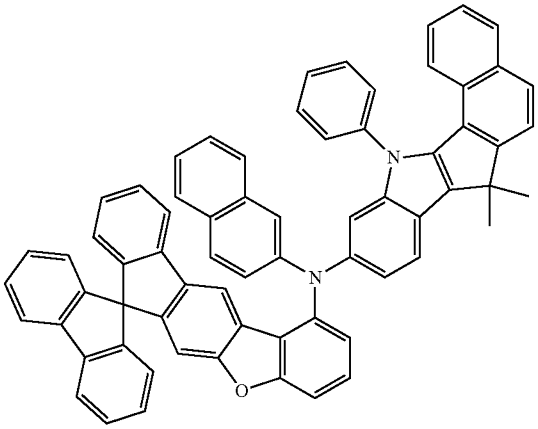

-continued
<Compound 253>
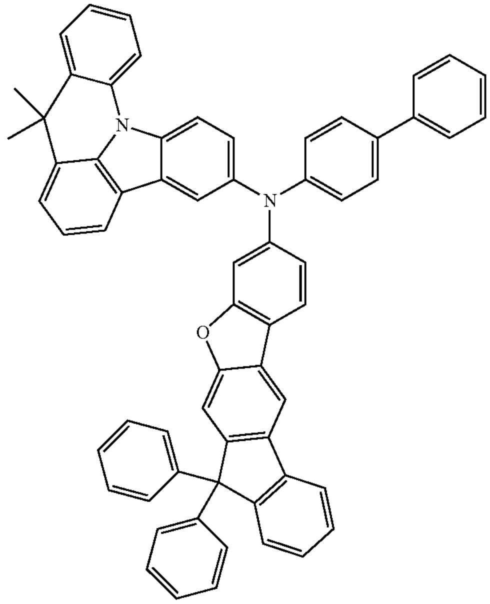
<Compound 254>
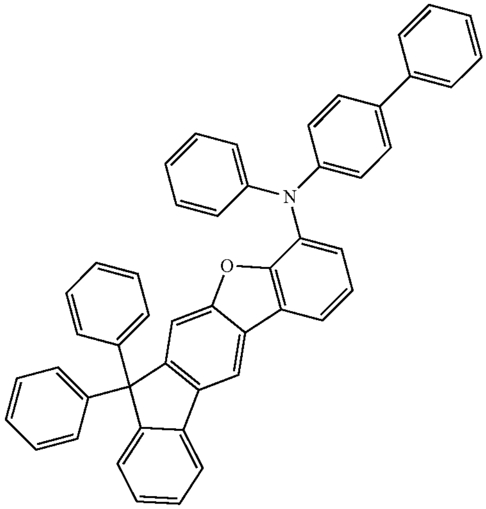
<Compound 255>
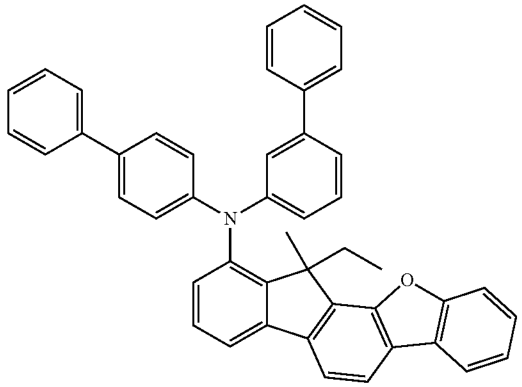
<Compound 256>
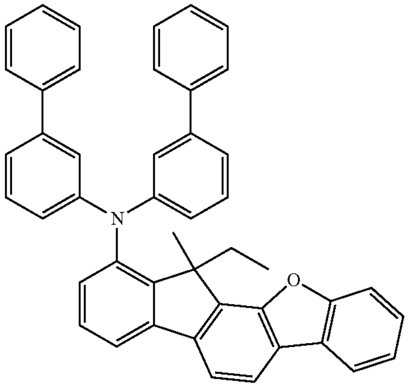
<Compound 257>
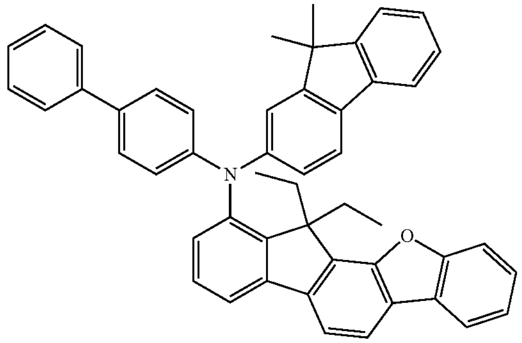
<Compound 258>
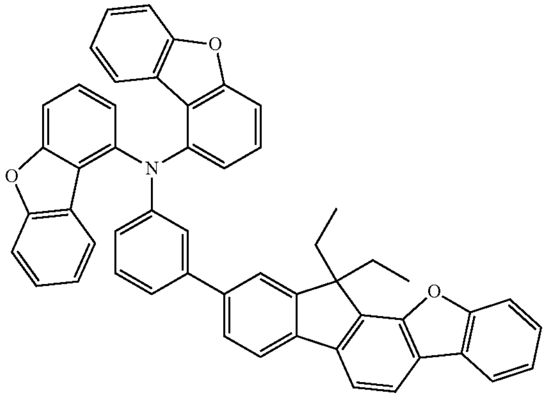

-continued
<Compound 259>
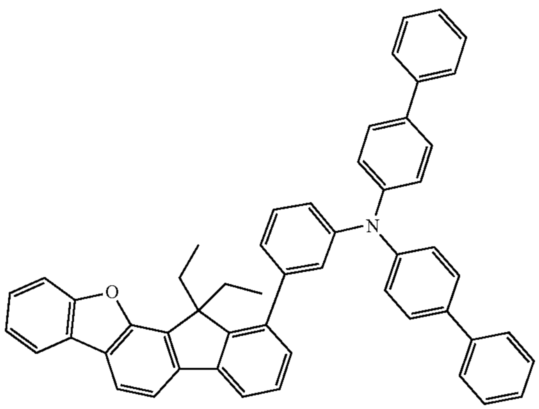
<Compound 260>
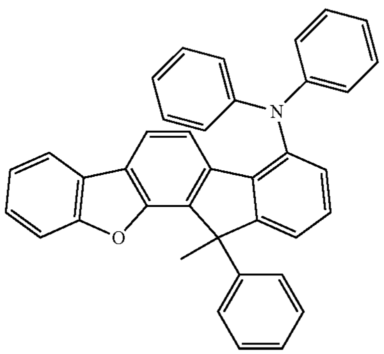
<Compound 261>
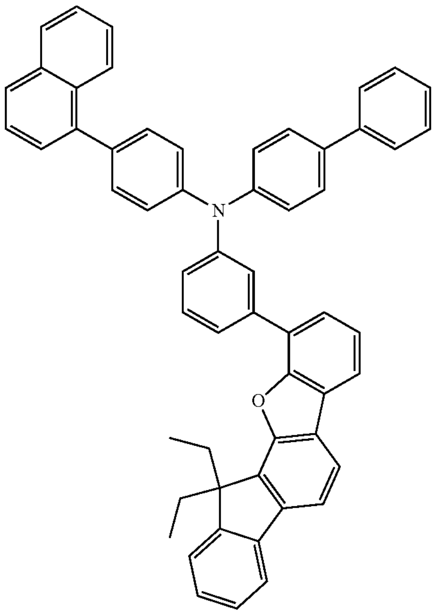
<Compound 262>
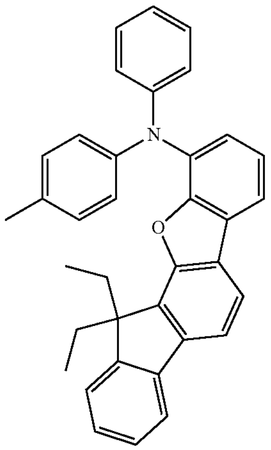
<Compound 263>
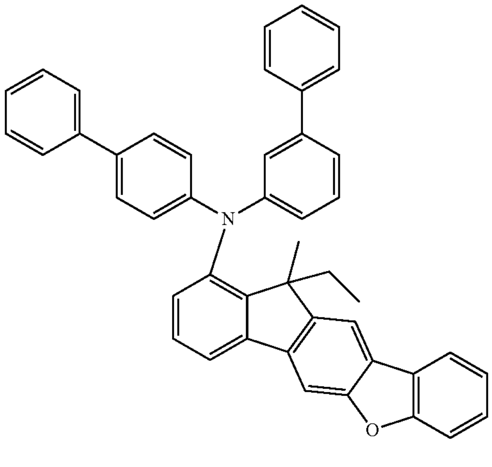
<Compound 264>
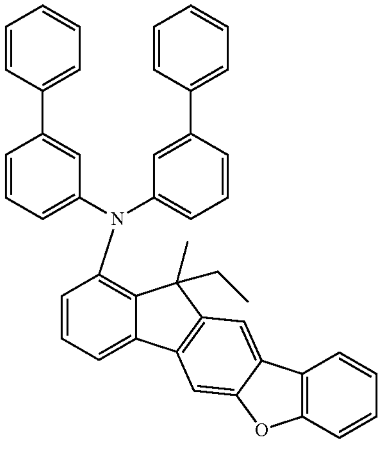

-continued
<Compound 265>
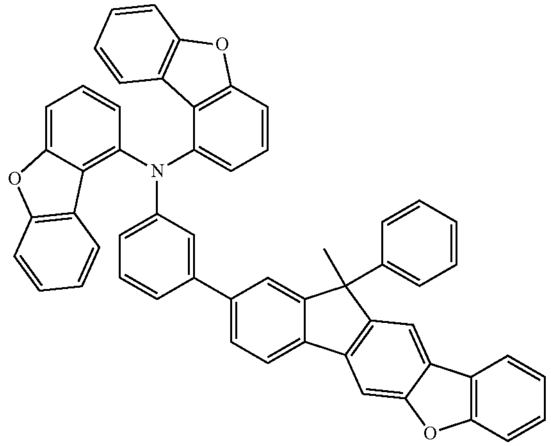
<Compound 266>
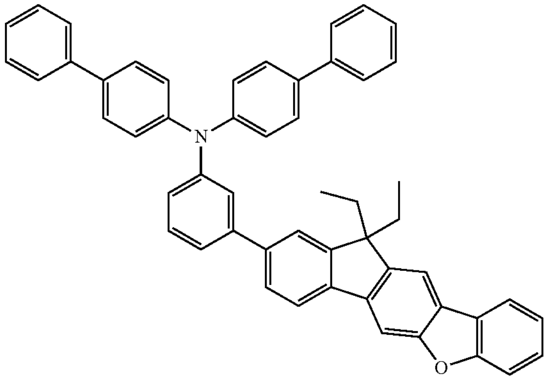
<Compound 267>
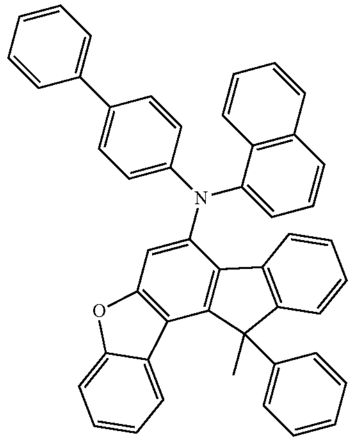
<Compound 268>
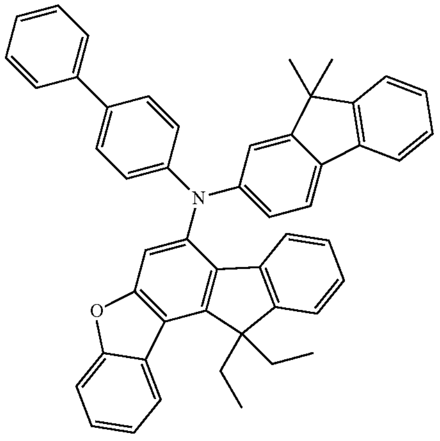
<Compound 269>
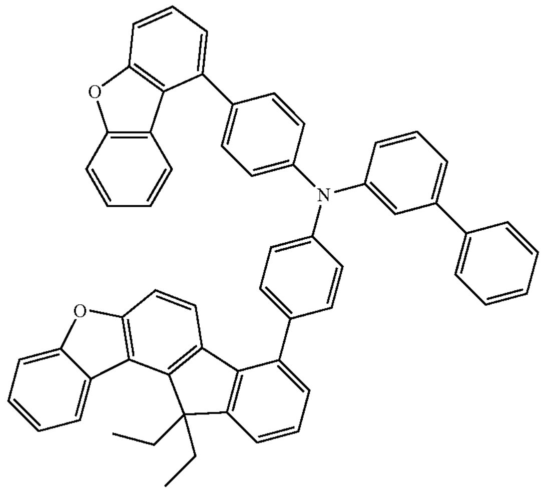
<Compound 270>
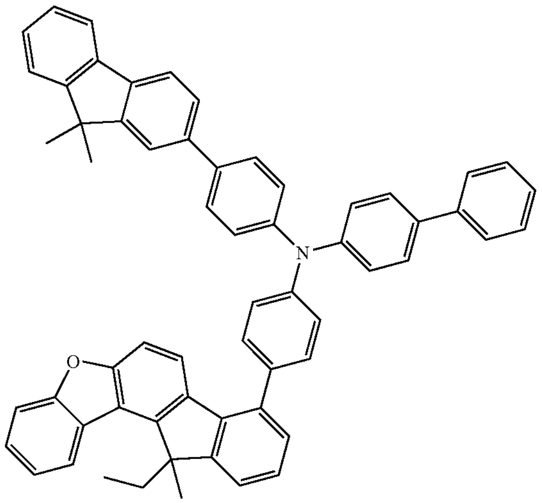

-continued
<Compound 271>
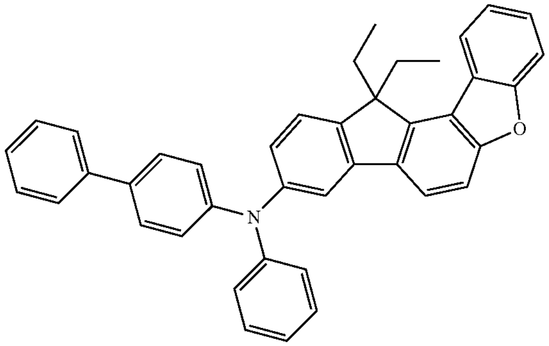
<Compound 272>
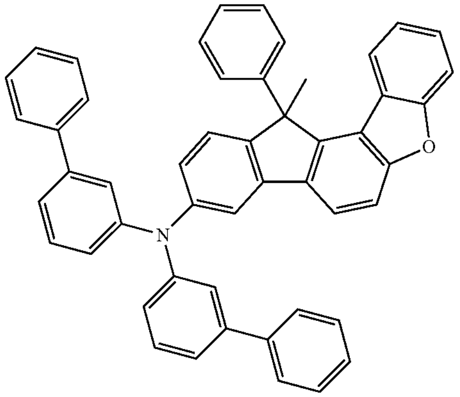
<Compound 273>
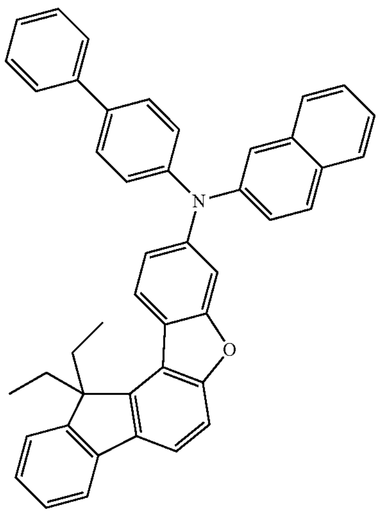
<Compound 274>
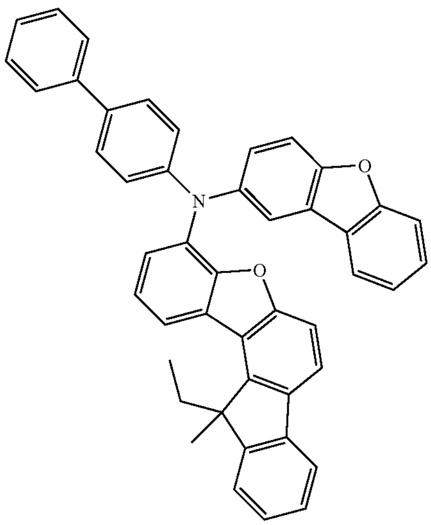
<Compound 275>
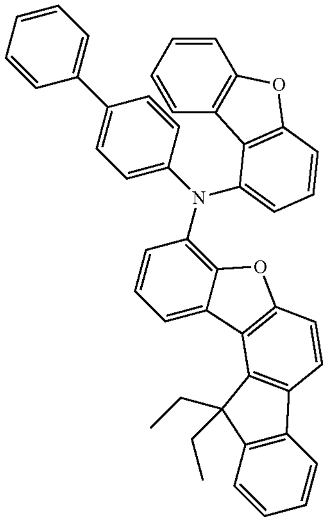
<Compound 276>
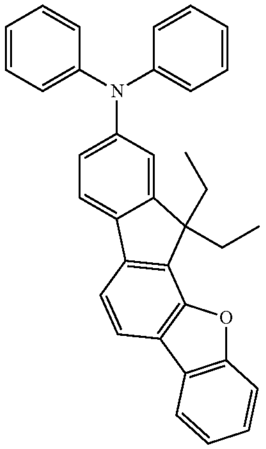

-continued
<Compound 277>
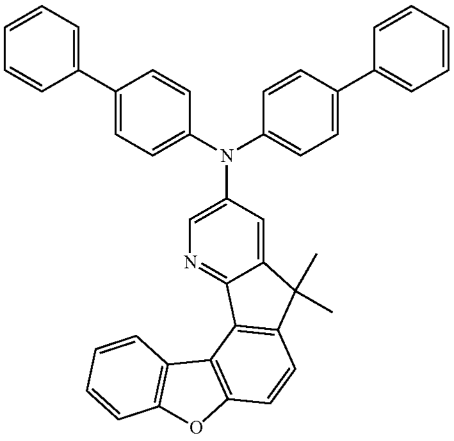
<Compound 278>
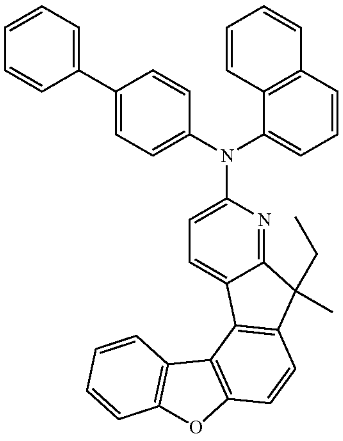
<Compound 279>
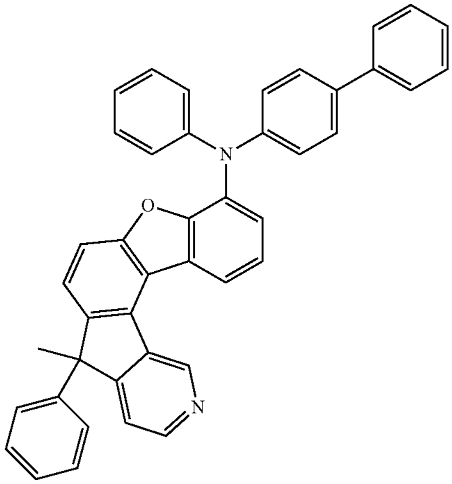
<Compound 280>
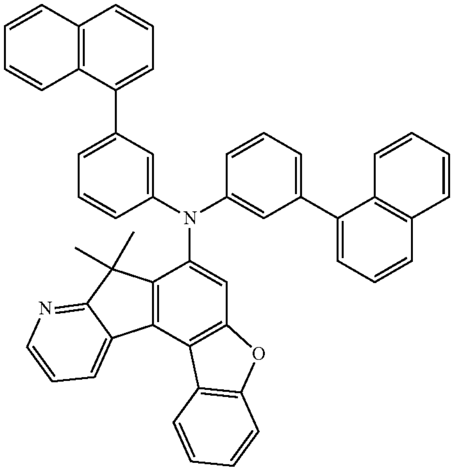
<Compound 281>
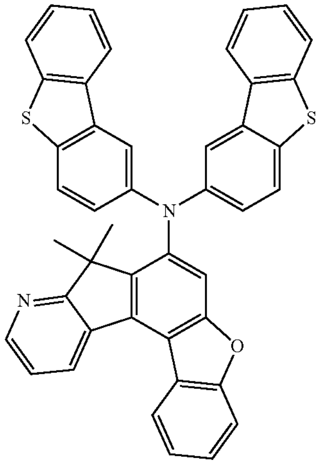
<Compound 282>
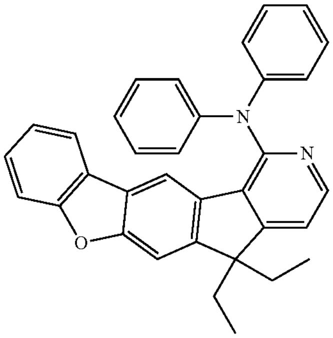

-continued
<Compound 283>
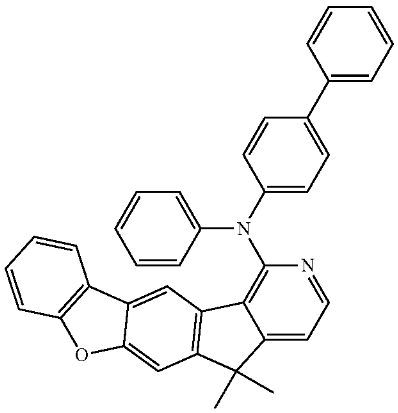
<Compound 284>
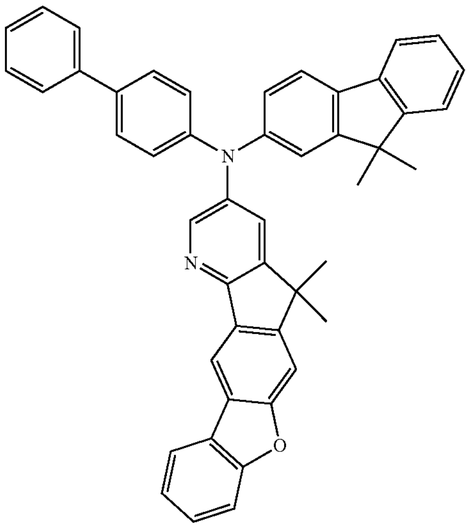
<Compound 285>
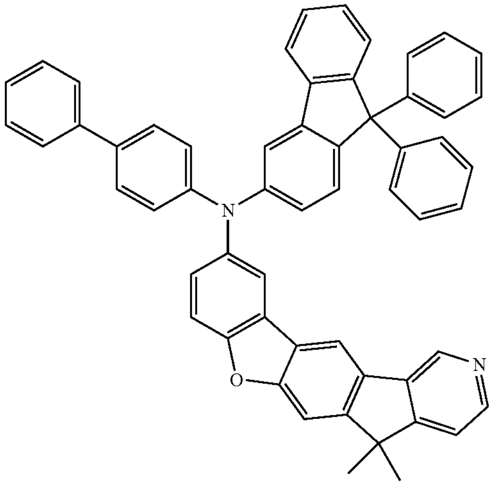
<Compound 286>
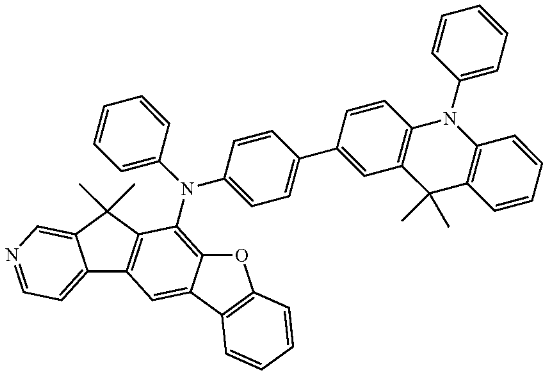
<Compound 287>
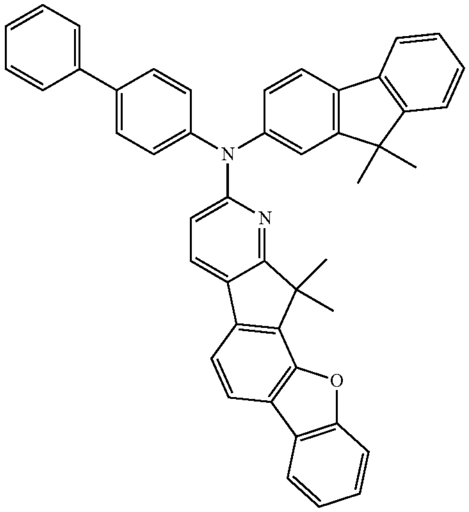
<Compound 288>
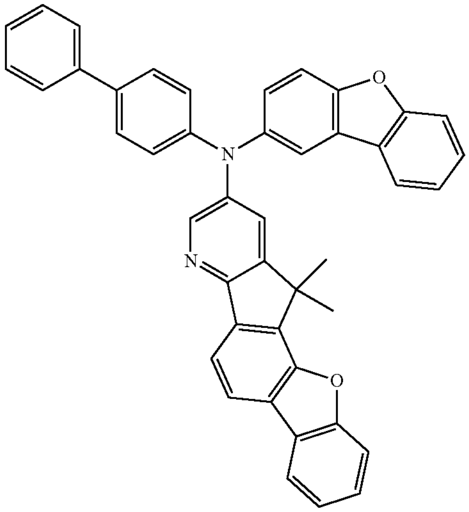

-continued
<Compound 289>
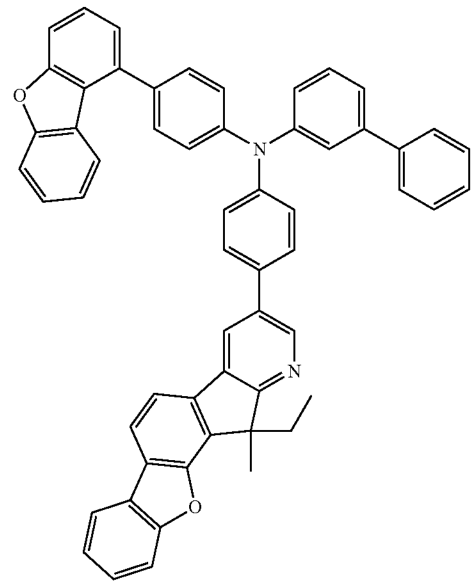
<Compound 290>
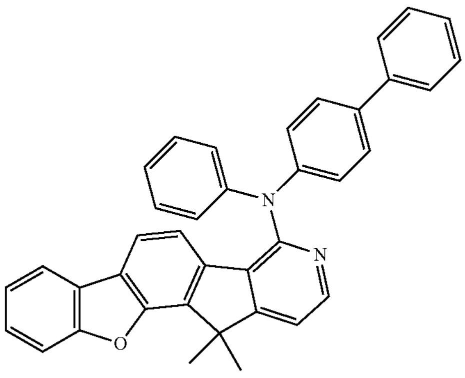
<Compound 291>
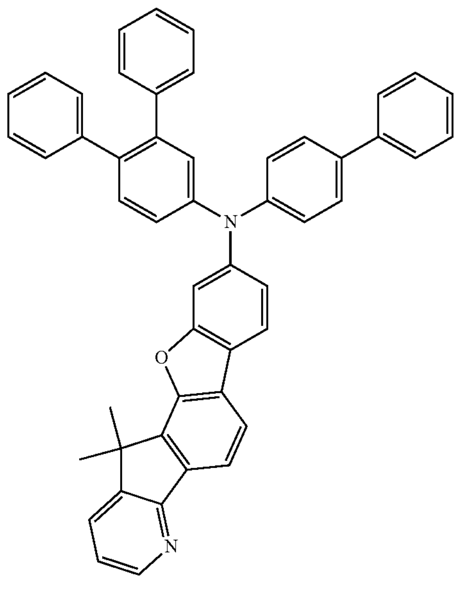
<Compound 292>
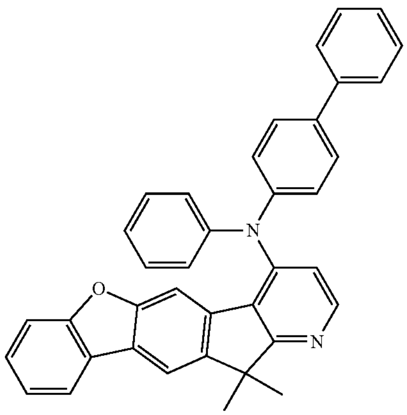

-continued
<Compound 293>
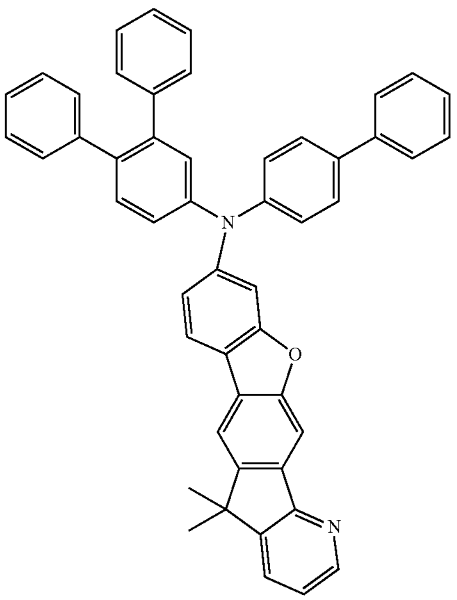
<Compound 294>
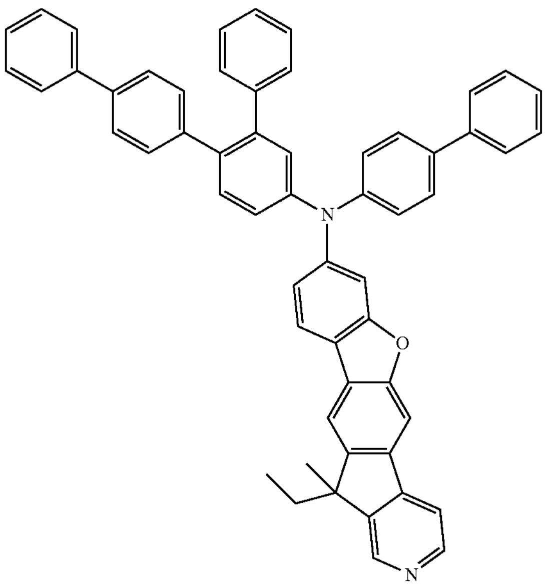
<Compound 295>
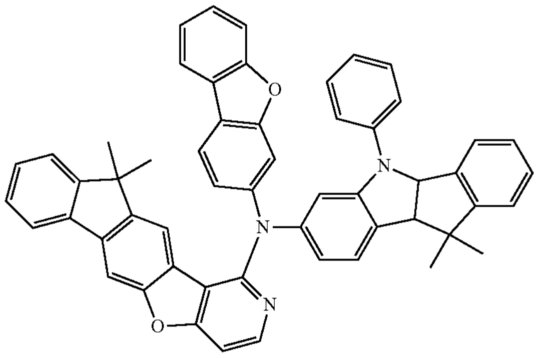
<Compound 296>
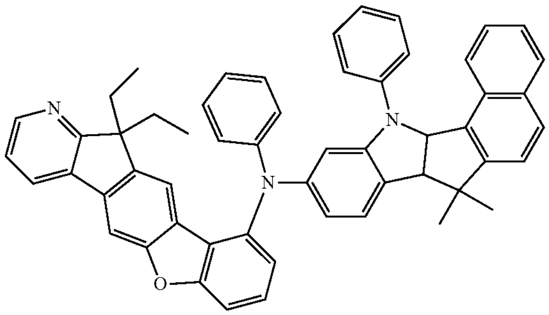
<Compound 297>
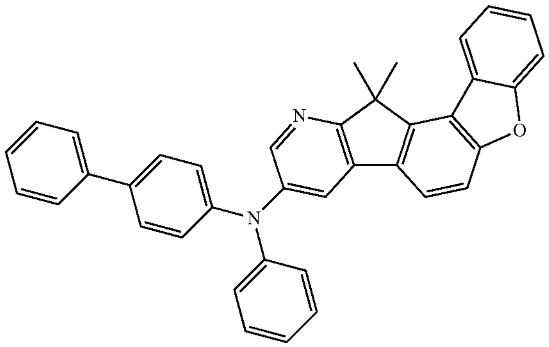
<Compound 298>
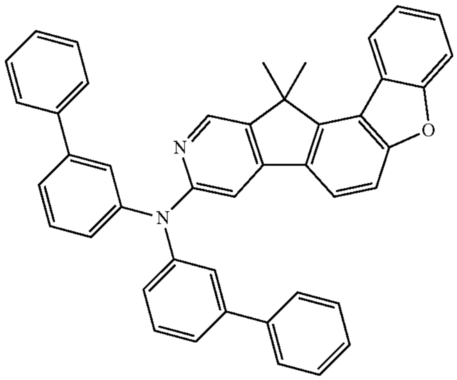

-continued
<Compound 299>
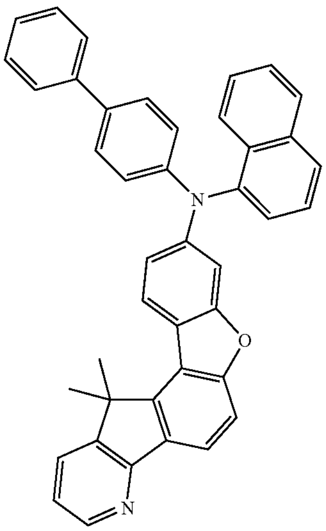
<Compound 300>
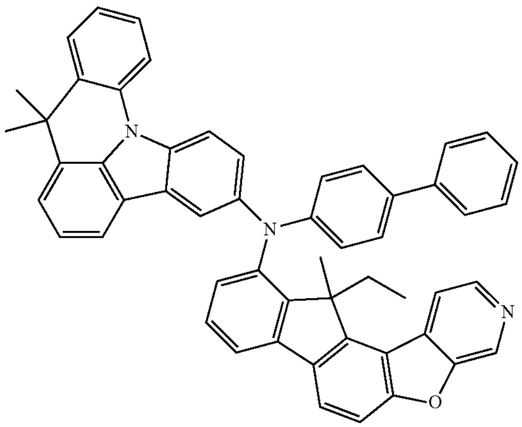
<Compound 301>
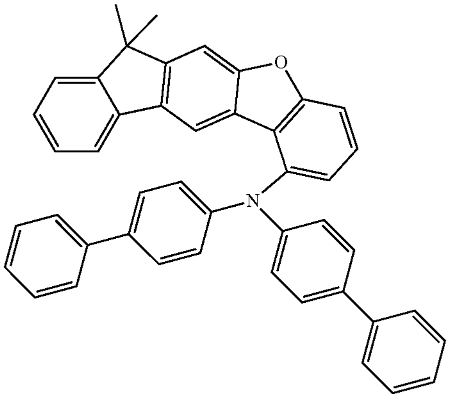
<Compound 302>
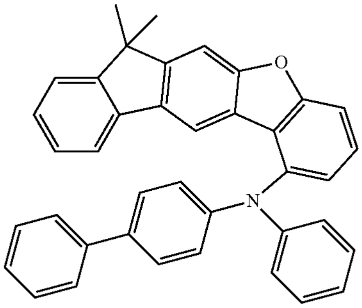
<Compound 303>
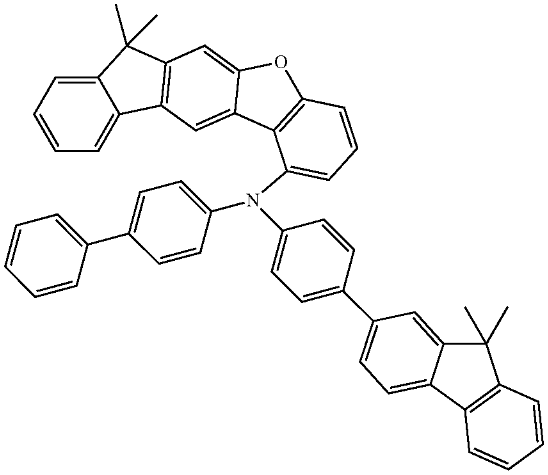
<Compound 304>
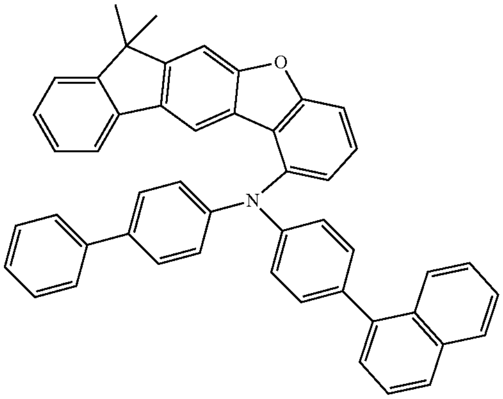

-continued
<Compound 305>
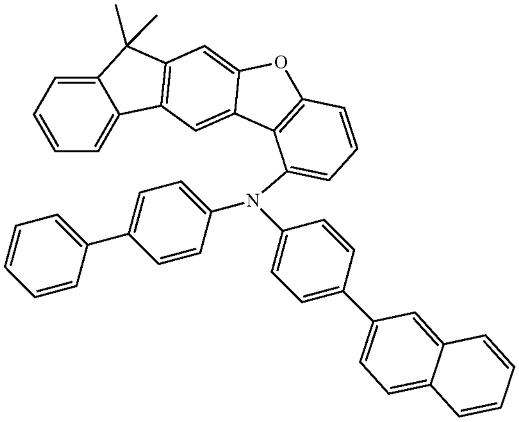
<Compound 306>
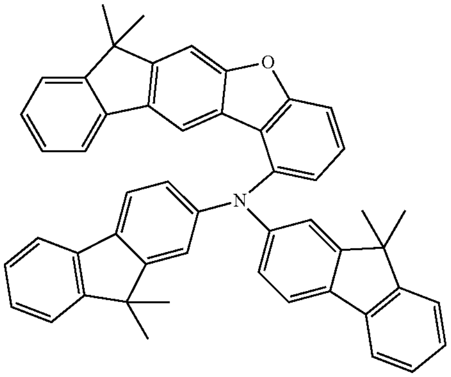
<Compound 307>
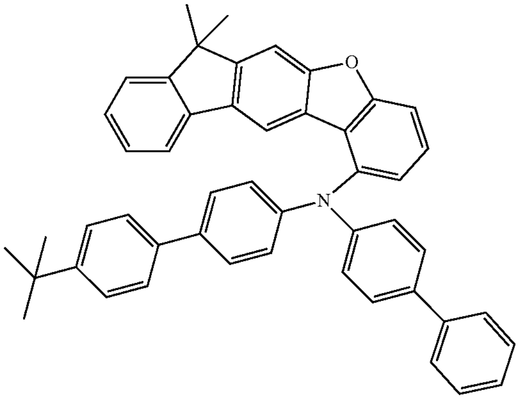
<Compound 308>
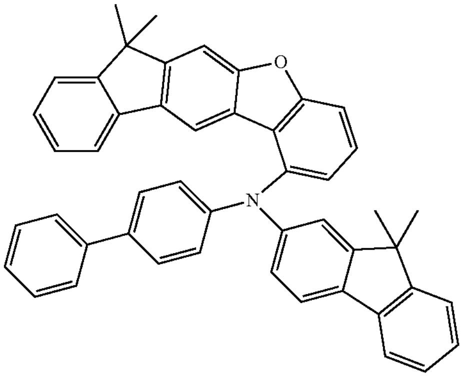
<Compound 309>
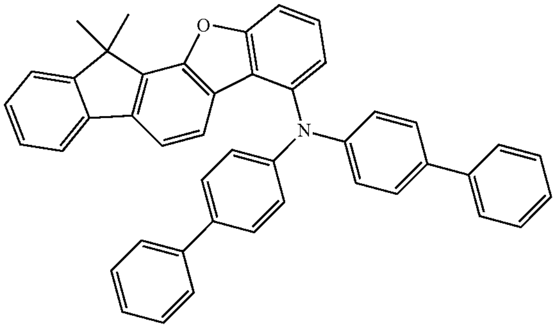
<Compound 310>
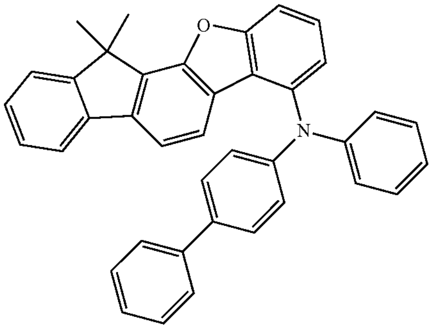
<Compound 311>
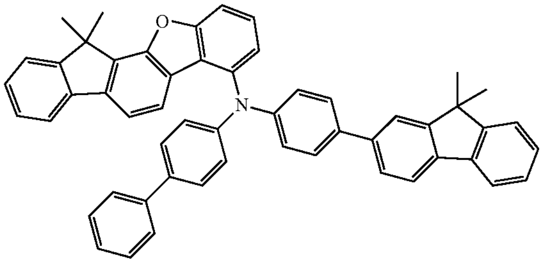
<Compound 312>
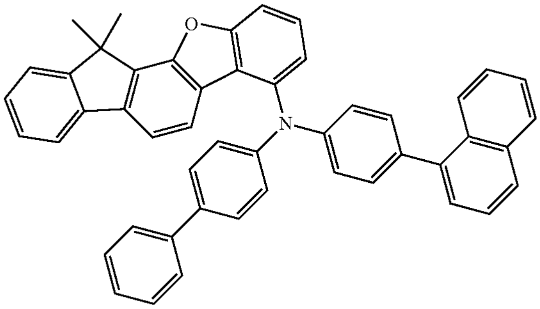

-continued
<Compound 313>
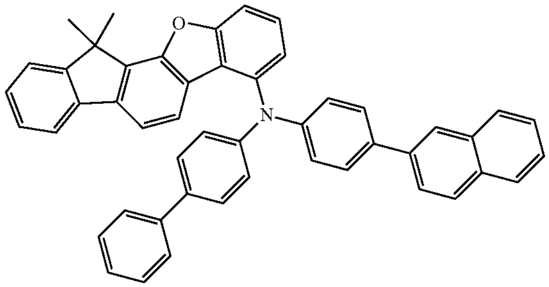
<Compound 314>
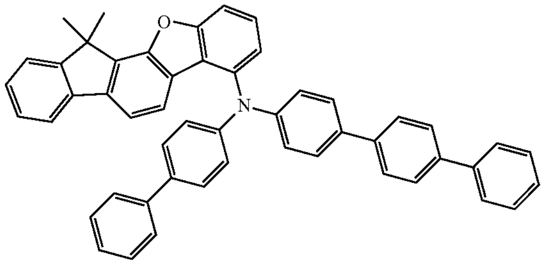
<Compound 315>
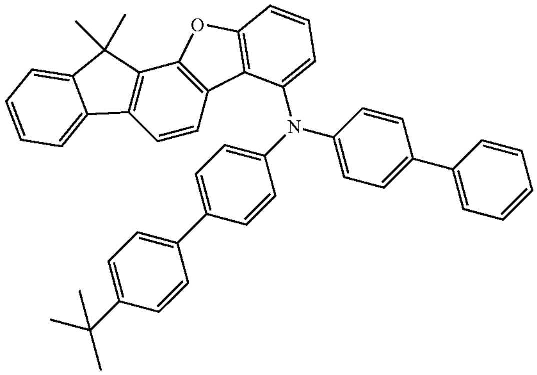
<Compound 316>
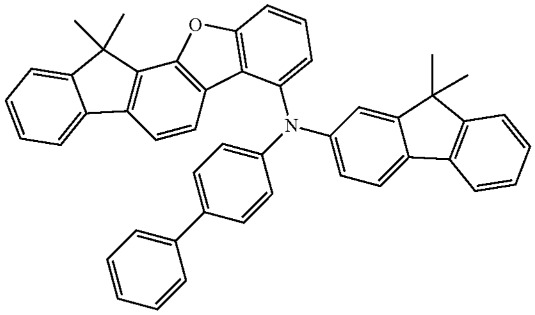
<Compound 317>
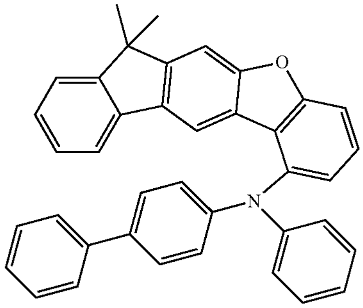
<Compound 318>
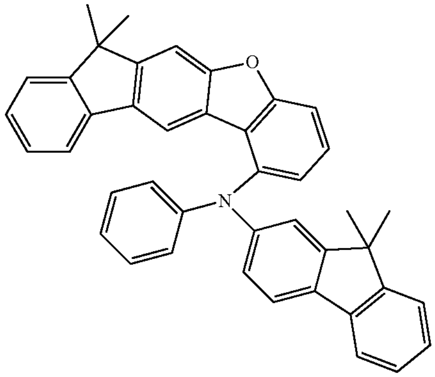
<Compound 319>
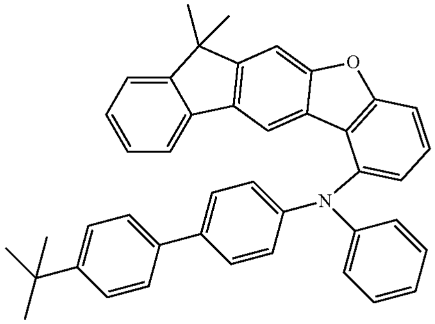
<Compound 320>
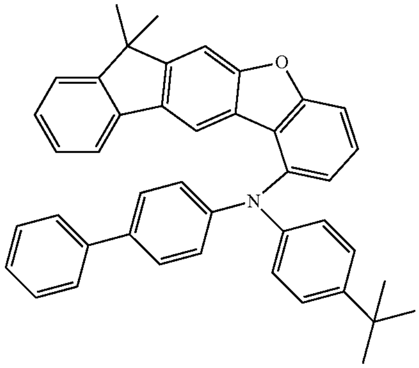

-continued

<Compound 321>

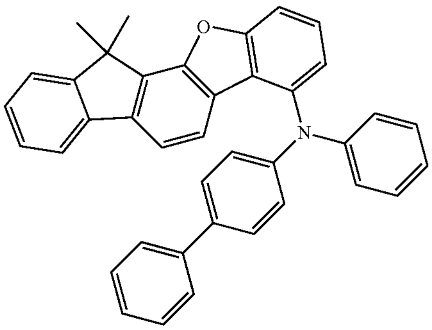

<Compound 322>

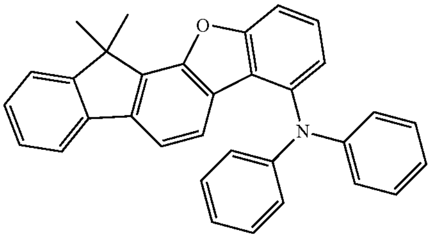

<Compound 323>

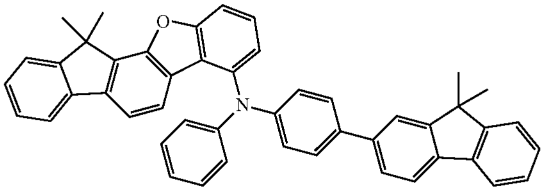

<Compound 324>

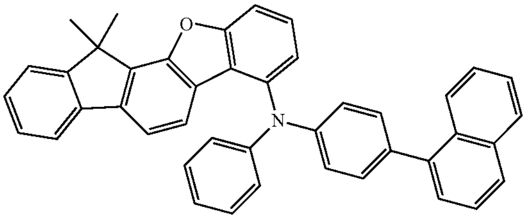

<Compound 325>

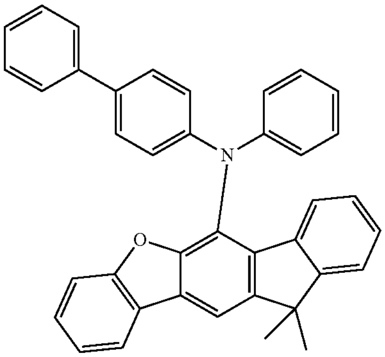

<Compound 326>

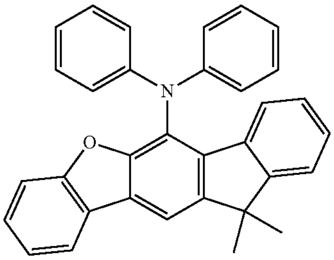

<Compound 327>

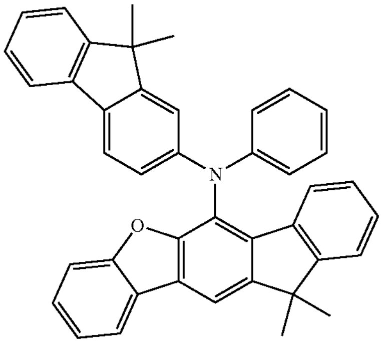

<Compound 328>

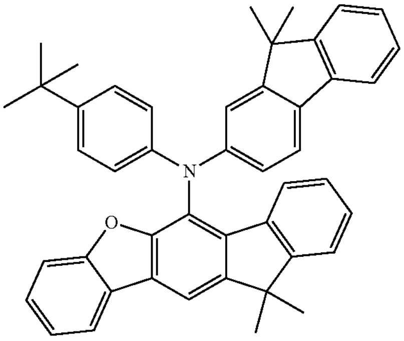

In accordance with another aspect thereof, the present disclosure addresses an organic light-emitting diode, comprising a first electrode; a second electrode facing the first electrode; and an organic layer interposed between the first electrode and the second electrode, wherein the organic layer includes at least one of the organic compounds according to the present disclosure.

As used herein, the expression "(the organic layer) . . . includes at least one of the organic compounds" is construed to mean that the organic layer may include one or two or more different organic compounds that fall within the scope of the present disclosure.

In this regard, the organic light-emitting diode of the present disclosure may further comprise at least one of a hole injection layer, a hole transport layer, a functional layer capable of both hole injection and hole transport, a light-emitting layer, an electron transport layer, and an electron injection layer.

The organic layer including the organic compound can be used in at least one of a hole injection layer, a hole transport layer, a functional layer capable of both hole injection and hole transport, a light-emitting layer, an electron transport layer, and an electron injection layer, and particularly, the organic compound may be recruited in a hole transport layer.

As a material for a hole transport layer in the organic light-emitting diode according to the present disclosure, the organic compound represented by any one of Chemical Formulas A to E of the present disclosure may be used.

Other compounds in addition to the organic compound represented by Chemical Formulas A to E may be further contained in the hole transport layer.

Compounds that are typically accepted in the art may be used in the hole transport layer.

For use as a material in a hole transport layer, an electron donating molecule having a low ionization potential is used. Predominantly, diamine, triamine or tetraamine derivatives having a triphenylamine skeleton are employed, as exemplified by N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

A hole injection layer (HIL) may be further deposited beneath the hole transport layer. The organic compound represented by any one of Chemical Formulas A to E may also be used as a material for the hole injection layer.

Otherwise, a compound that is typically used in the art may be employed in the hole injection layer.

Examples of such typical compounds for use in a hole injection layer include HATCN (Hexaazatriphenylenehexacarbonitrile), and the starburst amines TCTA (4,4',4"-tri (N-carbazolyl)triphenyl-amine) and m-MTDATA (4,4',4"-tris-(3-methylphenylphenyl amino)triphenylamine).

In addition, a light-emitting layer in the organic light-emitting diode of the present disclosure may include a host and a dopant. For this, the host in the light-emitting layer may include, but is not limited to, at least one of the compounds represented by the following Chemical Formula K:

[Chemical Formula K]

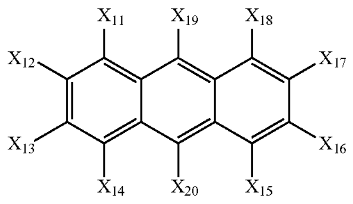

wherein,

X11 to X20, which may be the same or different, are each independently selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a substituted or unsubstituted silicone, a substituted or unsubstituted boron, a substituted or unsubstituted silane, a carbonyl, a phosphoryl, an amino, a nitrile, a hydroxy, a nitro, a halogen, an amide, and an ester, with a proviso that adjacent radicals may form an aliphatic, an aromatic, an aliphatic hetero, or an aromatic hetero fused ring.

Meanwhile, a dopant used in a light-emitting layer of the organic light-emitting diode according to the present disclosure may be a compound represented by the following Chemical Formula 1 or 2. In this regard, the light-emitting layer may further contain various dopant materials known in the art.

[Chemical Formula 1]

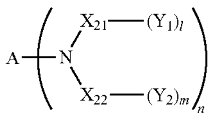

[Chemical Formula 2]

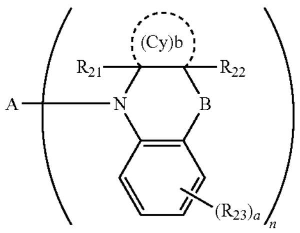

wherein,

A may be any one selected from among a substituted or unsubstituted aryl of 6 to 50 carbon atoms, a substituted or unsubstituted heteroaryl of 2 to 50 carbon atoms bearing O, N, or S as a heteroatom, a substituted or unsubstituted arylene of 6 to 60 carbon atoms, and a substituted or unsubstituted heteroarylene of 3 to 50 carbon atoms bearing O, N, or S as a heteroatom.

In greater detail, A may be a substituted or unsubstituted arylene of 6 to 60 carbon atoms, or a single bond, and particularly any one selected from among anthracene, pyrene, phenanthrene, indenophenanthrene, chrysene, naphthacene, pycene, triphenylene, perylene, and pentacene, and more particularly a substituent represented by the following Chemical Formulas A1 to A10:

[Chemical FormulaA1]

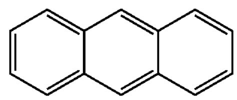

[Chemical FormulaA2]

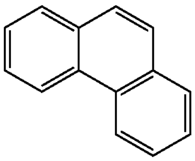

[Chemical FormulaA3]

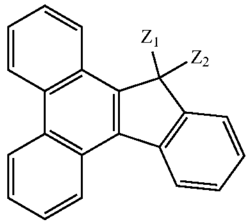

-continued

[Chemical FormulaA4]

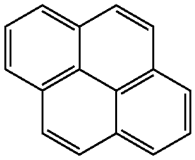

[Chemical FormulaA5]

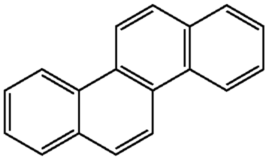

[Chemical FormulaA6]

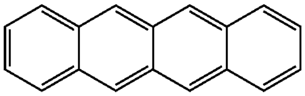

[Chemical FormulaA7]

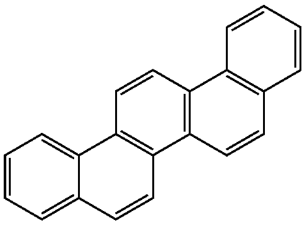

[Chemical FormulaA8]

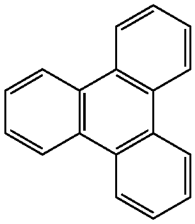

[Chemical FormulaA9]

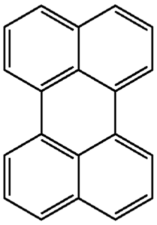

[Chemical FormulaA10]

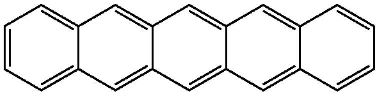

In Chemical Formula A3, Z1 and Z2 may be the same or different and are each independently selected from the group consisting of a hydrogen atom, a deuterium atom, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl) amino of 1 to 60 carbon atoms or a (substituted or unsubstituted aryl)amino of 6 to 60 carbon atoms, and a di(substituted or unsubstituted aryl)amino of 6 to 60 carbon atoms, with the proviso that Z1 and Z2 may the same or different and each form a fused ring with an adjacent radical.

In Chemical Formula 1,

X21 and X22 may each be independently a substituted or unsubstituted arylene of 6 to 30 carbon atoms or a single bond, with the proviso that X21 and X22 may bond to each other, Y1 and Y2 may be the same or different and are each independently selected from the group consisting of a substituted or unsubstituted aryl of 6 to 24 carbon atoms, a substituted or unsubstituted heteroaryl of 2 to 24 carbon atoms, a substituted or unsubstituted alkyl of 1 to 24 carbon atoms, a substituted or unsubstituted heteroalkyl of 1 to 24 carbon atoms, a substituted or unsubstituted cycloalkyl of 3 to 24 carbon atoms, a substituted or unsubstituted alkoxy of 1 to 24 carbon atoms, a cyano, a halogen, a substituted or unsubstituted aryloxy of 6 to 24 carbon atoms, a substituted or unsubstituted alkylsilyl of 1 to 40 carbon atoms, a substituted or unsubstituted arylsilyl of 6 to 30 carbon atoms, a germanium, a phosphorus, a boron, a deuterium, and a hydrogen, with the proviso that Y1 and Y2 may each form with an aliphatic, aromatic, heteroaliphatic, or heteroaromatic fused ring with an adjacent radical, l and m are each an integer of 1 to 20, and n is an integer of 1 to 4.

In Chemical Formula 2,

Cy is a substituted or unsubstituted cycloalkyl of 3 to 8 carbon atoms and b is an integer of 1 to 4, with the proviso that when b is an integer of 2 or greater, the corresponding cycloalkanes may be the same or different and may each be in a fused form having a deuterium or an alkyl as a substituent;

B is a single bond or —[C(R25) (R26)]p- wherein p is an integer of 1 to 3, with the proviso that when p is 2 or greater, the corresponding two or more R25's are the same or different and the corresponding two or more R26's are the same or different;

R21, R22, R23, R25, and R26 may each be independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl) amino of 1 to 60 carbon atoms, a di(substituted or unsubstituted alkyl)amino of 1 to 60 carbon atoms or a (substituted or unsubstituted aryl)amino of 6 to 60 carbon atoms, a di(substituted or unsubstituted aryl) amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorus, and a boron, a is an integer of 1 to 4, with the proviso that when a is 2 or greater, the corresponding plural R23's may be the same or different and may each be in a fused form, and n is an integer of 1 to 4.

The amine radical of Chemical Formulas 1 and 2, which is linked to A, may be represented by any one selected from among, but not limited to, the following Substituents 1 to 52:

[Substituent 1]

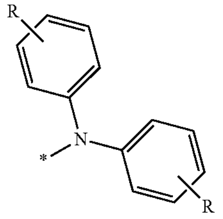

[Substituent 2]

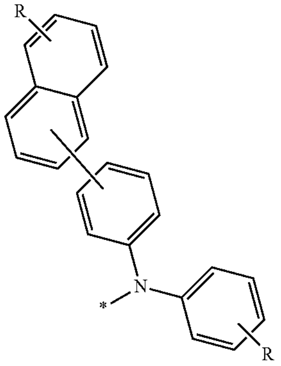

[Substituent 3]

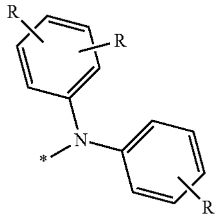

[Substituent 4]

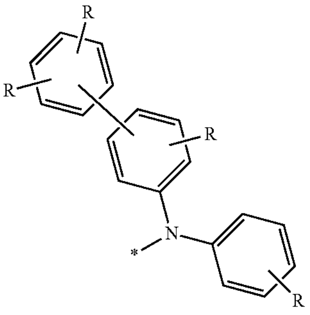

-continued

[Substituent 5]

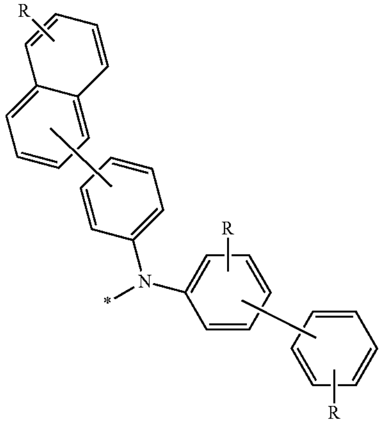

[Substituent 6]

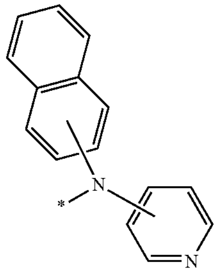

[Substituent 7]

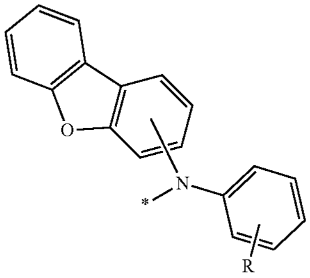

[Substituent 8]

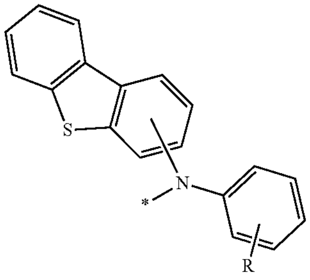

[Substituent 9]

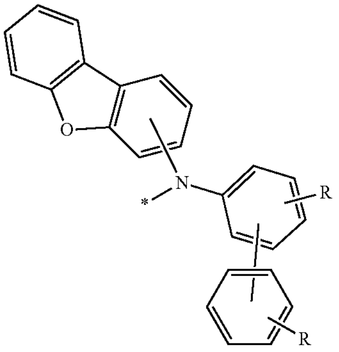

[Substituent 10]
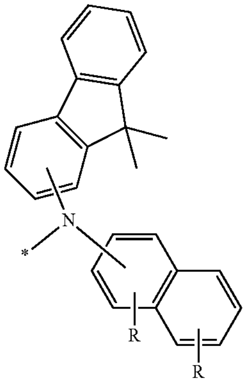
[Substituent 11]
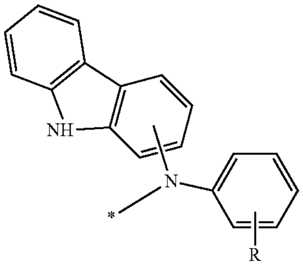
[Substituent 12]
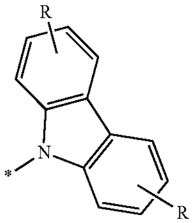
[Substituent 13]
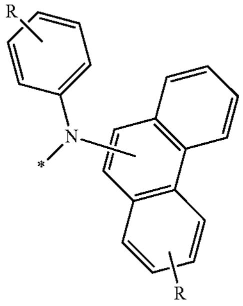
[Substituent 14]
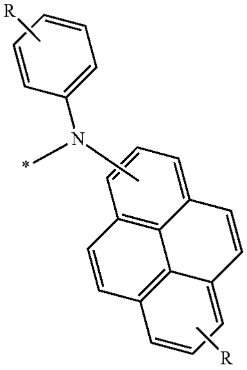
[Substituent 15]
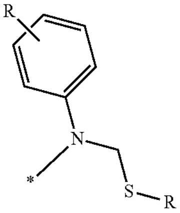
[Substituent 16]
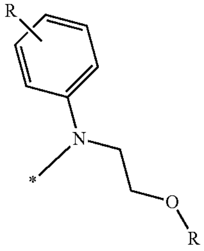
[Substituent 17]
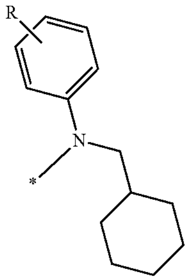
[Substituent 18]
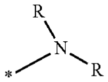
[Substituent 19]
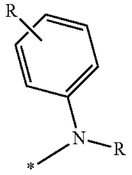
[Substituent 20]
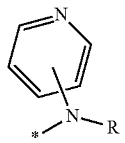
[Substituent 21]
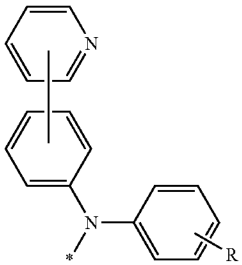

[Substituent 22]
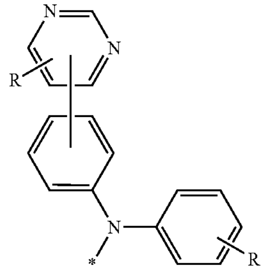
[Substituent 23]
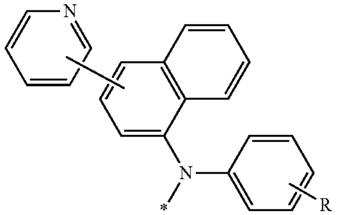
[Substituent 24]
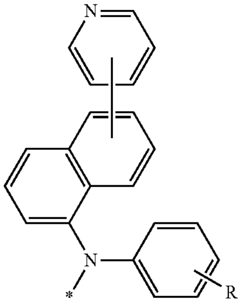
[Substituent 25]
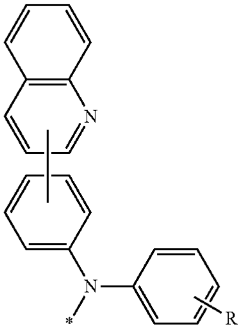
[Substituent 26]
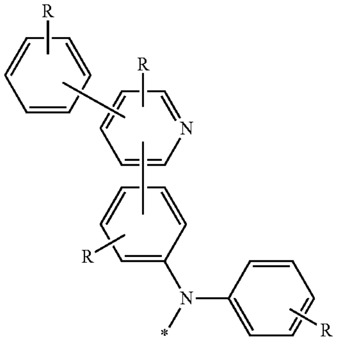
[Substituent 27]
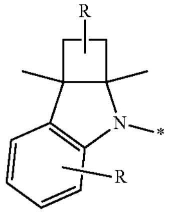
[Substituent 28]
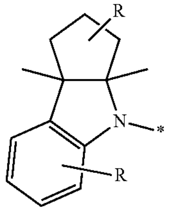
[Substituent 29]
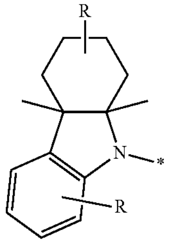
[Substituent 30]
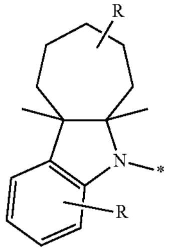
[Substituent 31]
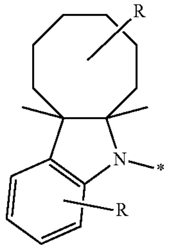
[Substituent 32]
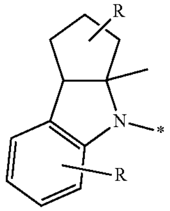

-continued
[Substituent 33]
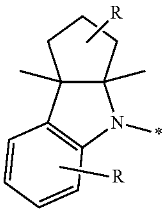
[Substituent 34]
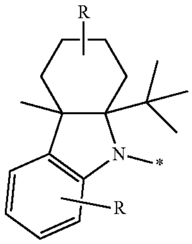
[Substituent 35]
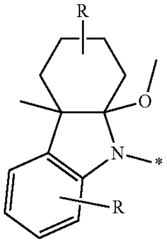
[Substituent 36]
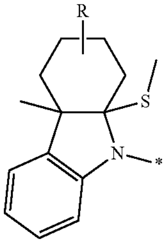
[Substituent 37]
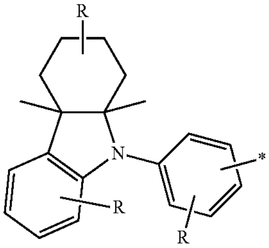
[Substituent 38]
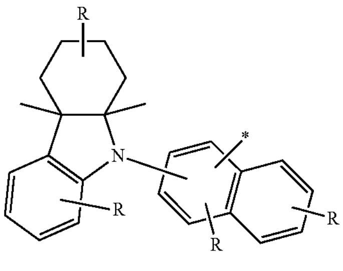
-continued
[Substituent 39]
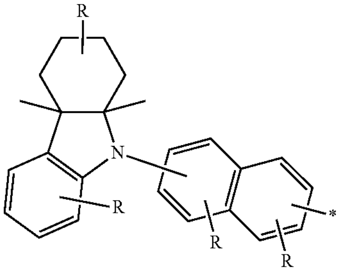
[Substituent 40]
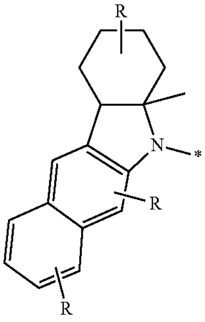
[Substituent 41]
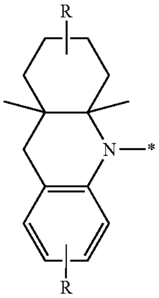
[Substituent 42]
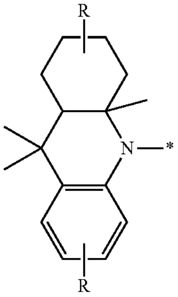
[Substituent 43]
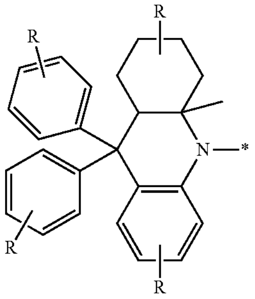

[Substituent 44]

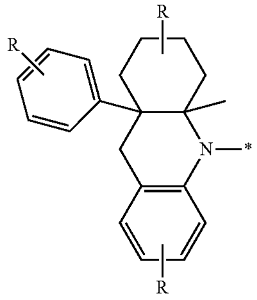

[Substituent 45]

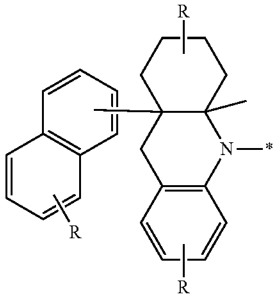

[Substituent 46]

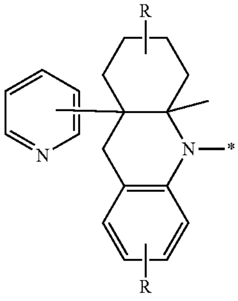

[Substituent 47]

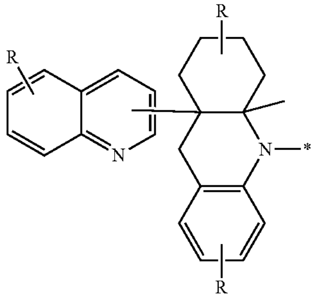

[Substituent 48]

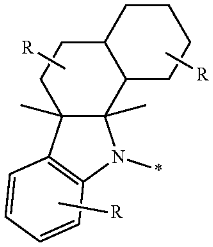

[Substituent 49]

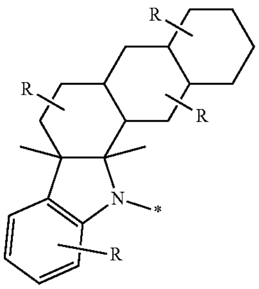

[Substituent 50]

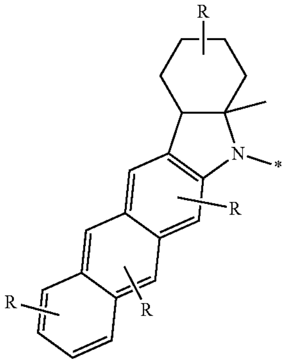

[Substituent 51]

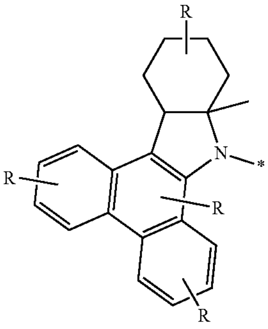

[Substituent 52]

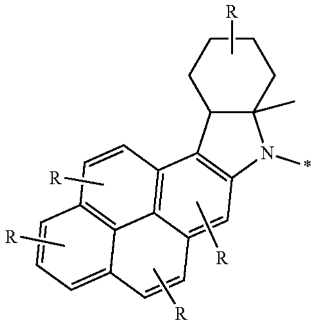

wherein R's, which may be the same or different, are each independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di (substituted or unsubstituted alkyl) amino of 1 to 60 carbon atoms or a (substituted or unsubstituted aryl)amino of 6 to 60 carbon atoms, a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, may each have 1 to 12 substituents, and may each form a fused ring with an adjacent radical.

The light-emitting layer may contain various host and dopant materials in addition to the aforementioned dopant and host materials.

When the light-emitting layer contains a host and a dopant, the content of the dopant in the light-emitting layer may range from about 0.01 to 20 parts by weight based on 100 parts by weight of the host, but is not limited thereto.

Meanwhile, examples of the material typically used in an electron transport layer include quinoline derivatives, particularly tris(8-quinolinolate)aluminum (Alq3), TAZ, BAlq, beryllium bis(benzoquinolin-10-oate: Bebq2), BCP, compound 201, compound 202, and the oxadiazole derivatives PBD, BMD, and BND, but are not limited thereto.

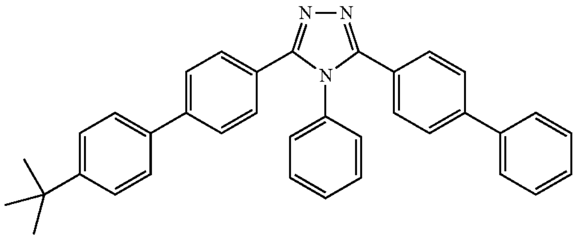

TAZ

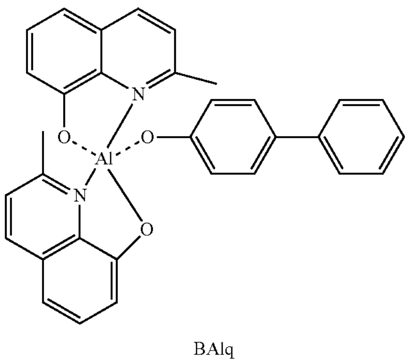

BAlq

-continued

<Compound 501>

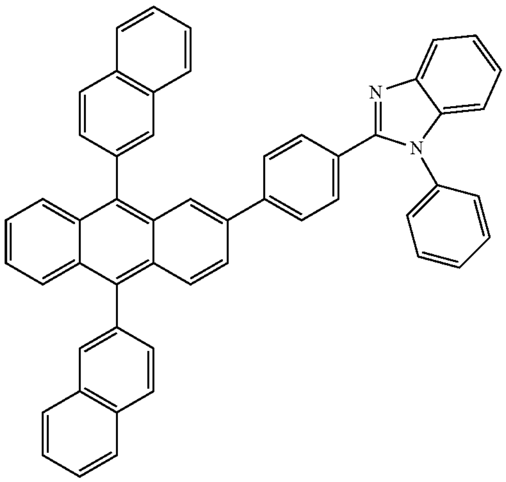

<Compound 502>

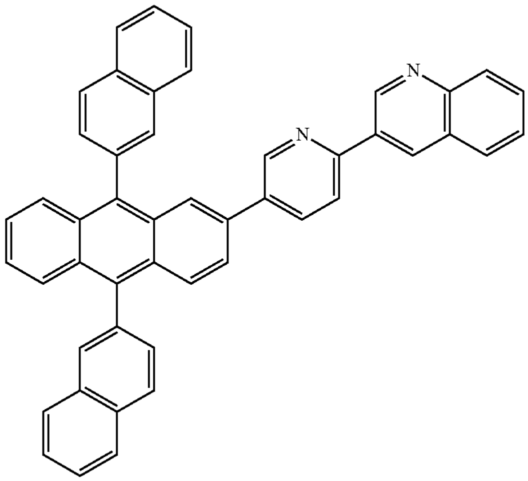

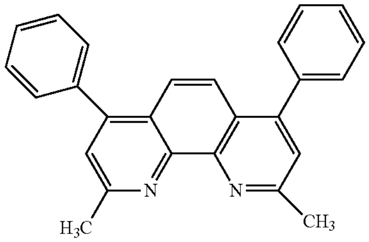

BCP

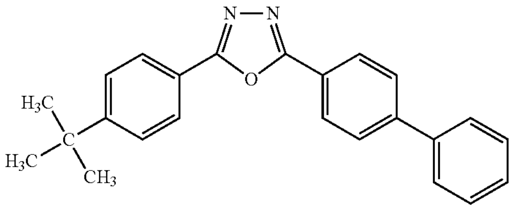

PBD

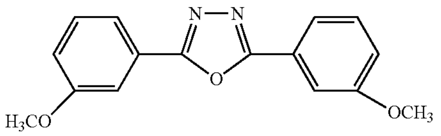

BMD

-continued

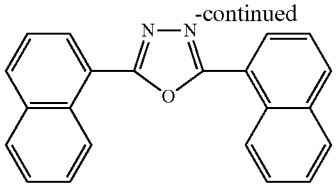

BMD

In addition, the organic metal compound represented by Chemical Formula F may be used, either alone or in combination with the aforementioned material, as a compound for an electron transport layer in the present disclosure:

[Chemical Formula F]

$$Y_m—M—(OA)_n$$

wherein,

Y is a ligand that contains two moieties respectively responsible for forming a single bond through a direct bond to M and for forming a coordinate bond with M, each moiety being selected from among C, N, O and S, and which is chelated by the single bond and the coordinate bond;

M is an alkali metal, an alkaline earth metal, an aluminum (Al) atom, or a boron (B) atom, with the proviso that:

when M is an alkali metal, m=1 and n=0 when M is an alkaline earth metal, m=1 and n=1, or m=2 and n=0, or when M is aluminum or a boron, m is an integer of 1 to 3 and n is an integer of 0 to 2, satisfying the relationship m+n=3; and OA is a monodentate ligand capable of forming a single bond or a coordinate bond with M, wherein O is oxygen, and A is selected from among a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing O, N, or S as a heteroatom.

An electron injection layer (EIL) that functions to facilitate electron injection from the cathode, thus improving the power efficiency of the diode, may be further deposited on the electron transport layer. So long as it is conventionally used in the art, any material can be available for the electron injection layer without particular limitations. Examples include LiF, NaCl, CsF, Li2O, and BaO.

Deposition conditions for the electron injection layer may vary, depending on compounds used, but may be generally selected from condition scopes that are almost the same as for the formation of hole injection layers.

The electron injection layer may range in thickness from about 1 Å to about 100 Å, and particularly from about 3 Å to about 90 Å. Given the thickness range for the electron injection layer, the diode can exhibit satisfactory electron injection properties without actually elevating a driving voltage.

Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

Further, one or more layers selected from among a hole injecting layer, a hole transport layer, a functional layer capable of both hole injection and hole transport, a light-emitting layer, an electron transport layer, and an electron injection layer may be deposited using a deposition process or a solution process.

Here, the deposition process is a process by which a material is vaporized and deposited in a vacuum or at a low pressure to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

Below, the organic light-emitting diode of the present disclosure is explained with reference to FIG. 1.

FIG. 1 is a schematic cross-sectional view of the structure of an organic light-emitting diode according to some embodiments of the present disclosure. The organic light-emitting diode includes an anode 20, a hole transport layer 40, an organic light-emitting layer 50, an electron transport layer 60, and a cathode 80, and optionally a hole injection layer 30 or an electron injection layer 70. In addition, one or two intermediate layers may be further formed in the organic light-emitting diode. A hole barrier layer or an electron barrier layer may be also further established.

Reference is made to FIG. 1 with regard to the organic light-emitting diode of the present disclosure and the fabrication thereof. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide (SnO2), or zinc oxide (ZnO), which are transparent and superior in terms of conductivity, may be used. A hole injection layer material is applied on the anode electrode 20 by thermal deposition in a vacuum or by spin coating to form a hole injection layer 30. Subsequently, using thermal deposition in a vacuum or spin coating, a hole transport layer material is applied to the hole injection layer 30 to form a hole transport layer 40.

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitation. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

A better understanding of the present disclosure may be obtained through the following examples which are set forth to illustrate, but are not to be construed as limiting the present disclosure.

Synthesis Example 1: Synthesis of [Compound 1]

Synthesis Example 1-1: Synthesis of [Intermediate 1-a]

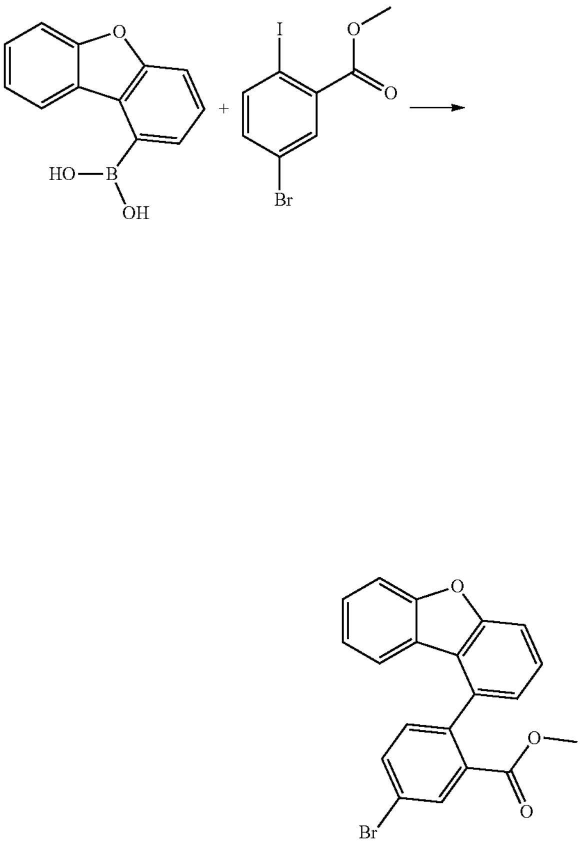

[Intermediate 1-a]

Dibenzofuran-1-boronic acid (25 g, 118 mmol), methyl-5-bromo-2-iodobenzoate (40.5 g, 118 mmol), tetrakis(triphenylphosphine)palladium (2.7 g, 2.3 mmol), potassium carbonate (33 g, 237 mmol), toluene (200 ml), 1,4-dioxane (200 ml), and water (100 ml) were placed under a nitrogen atmosphere in a round-bottom flask and fluxed for 12 hours. After completion of the reaction, the reaction mixture was layer separated, and the organic layer was concentrated at a reduced pressure. Column chromatographic separation yielded Intermediate 1-a (33.5 g): yield 74%

Synthesis Example 1-2: Synthesis of [Intermediate 1-b]

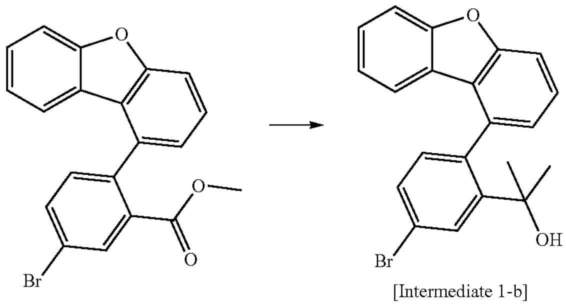 [SMILES: COC(=O)c1cc(Br)ccc1-c1cccc2oc3ccccc3c12 ; CC(C)(O)c1cc(Br)ccc1-c1cccc2oc3ccccc3c12]

[Intermediate 1-b]

In a round-bottom flask, Intermediate 1-a (33.5 g, 110 mmol) was added to tetrahydrofuran (150 ml) and cooled to −10° C. before slow addition of drops of 3 M methyl magnesium bromide (85 ml, 254 mmol) thereto. After the temperature was elevated to 40° C., stirring was performed for 4 hours. Then, the temperature was reduced to −10° C. and drops of 2 N HCl (70 ml) were slowly added. Subsequently, an aqueous ammonium chloride solution (70 ml) was added, followed by elevation to room temperature. After completion of the reaction, the reaction mixture was washed with water, concentrated in a vacuum, and separated by column chromatography to afford [Intermediate 1-b] (27 g): yield 80%

Synthesis Example 1-3: Synthesis of [Intermediate 1-c]

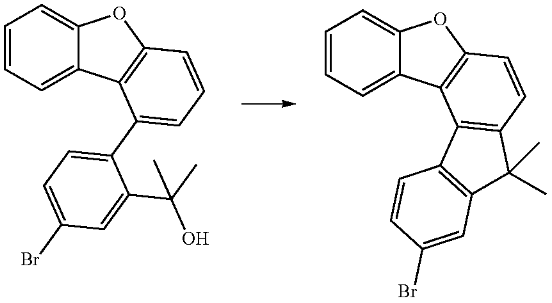

[Intermediate 1-c]

In a round-bottom flask, Intermediate 1-b (27 g, 89.2 mmol) and phosphoric acid (70 ml) were stirred together at room temperature for 12 hours under a nitrogen atmosphere. After completion of the reaction, the reaction mixture was extracted, concentrated, and separated by column chromatography to afford Intermediate 1-c (17.6 g): yield 70% Synthesis Example 1-4: Synthesis of [Compound 1]

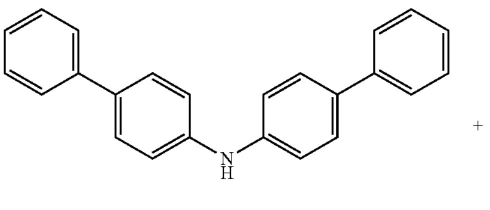

-continued

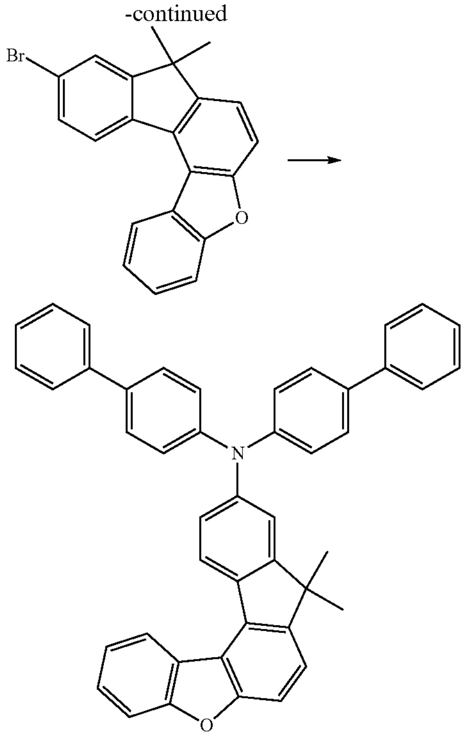

[Compound 1]

In a round-bottom flask, Intermediate 1-c (10 g, 27.5 mmol), bis(4-biphenyl)amine (8.8 g, 27.5 mmol), bis(dibenzylideneacetone)dipalladium (0.5 g, 0.6 mmol), BINAP (0.7 g, 1.1 mmol), sodium tert-butoxide (6.6 g, 68.8 mmol), and toluene (100 ml) were fluxed for 12 hours under a nitrogen atmosphere. After completion of the reaction, the organic layer was concentrated in a vacuum. Column chromatographic separation afforded Compound 1 (11.8 g): yield 72%

MS (MALDI-TOF): m/z 603.26 [M]+

Synthesis Example 2: Synthesis of [Compound 3]

Synthesis Example 2-1: Synthesis of [Compound 3]

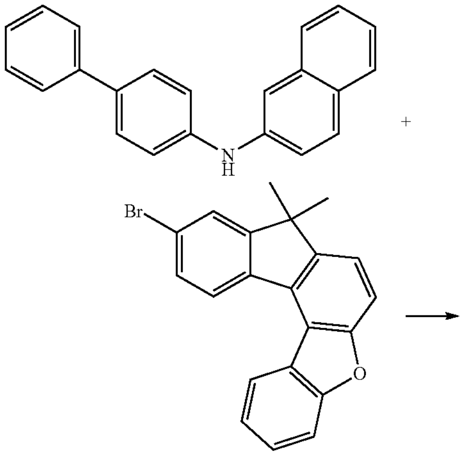

-continued

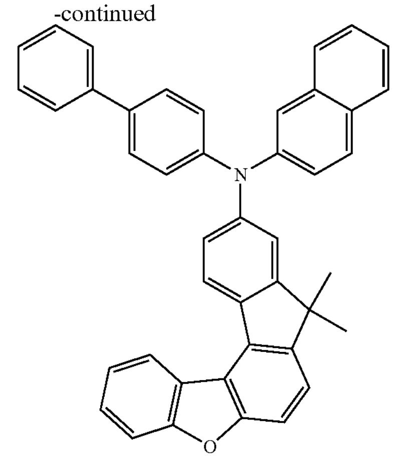

[Compound 3]

The same procedure as in Synthesis Example 1-4 was carried out, with the exception of using N-(naphthalen-2-yl)biphenyl-4-amine instead of bis(4-biphenyl)amine, to afford Compound 3: yield 67%

MS (MALDI-TOF): m/z 577.24 [M]+

Synthesis Example 3: Synthesis of [Compound 67]

Synthesis Example 3-1: Synthesis of [Intermediate 3-a]

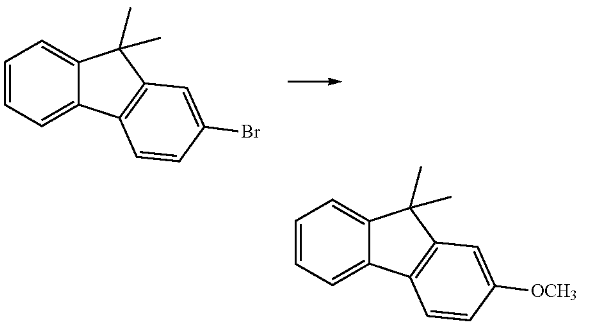

[Intermediate 3-a]

In a round-bottom flask, 2-bromo-9,9-dimethylfluorene (50 g, 183 mmol), an aqueous sodium methoxide (59.3 g, 1098 mmol), copper iodide (10.4 g, 54.9 mmol), and methanol (200 ml) were fluxed for 12 hours under a nitrogen atmosphere. After completion of the reaction, the organic layer was concentrated in a vacuum. Column chromatographic separation afforded Intermediate 3-a (33.2 g): yield 81%

Synthesis Example 3-2: Synthesis of [Intermediate 3-b]

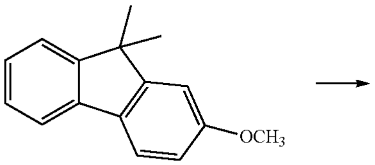

-continued

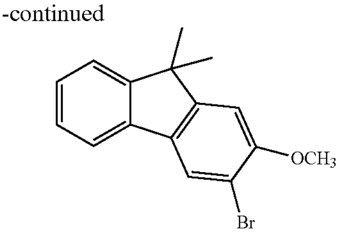

[Intermediate 3-b]

In a round-bottom flask, Intermediate 3-a (30 g, 133 mmol), N-bromosuccinimide (23.8 g, 133 mmol), and dimethylformamide (600 ml) were stirred together at 50° C. for 12 hours under a nitrogen atmosphere. After completion of the reaction, the organic layer was concentrated in a vacuum. Column chromatographic separation afforded Intermediate 3-b (28 g): yield 70%

Synthesis Example 3-3: Synthesis of [Intermediate 3-c]

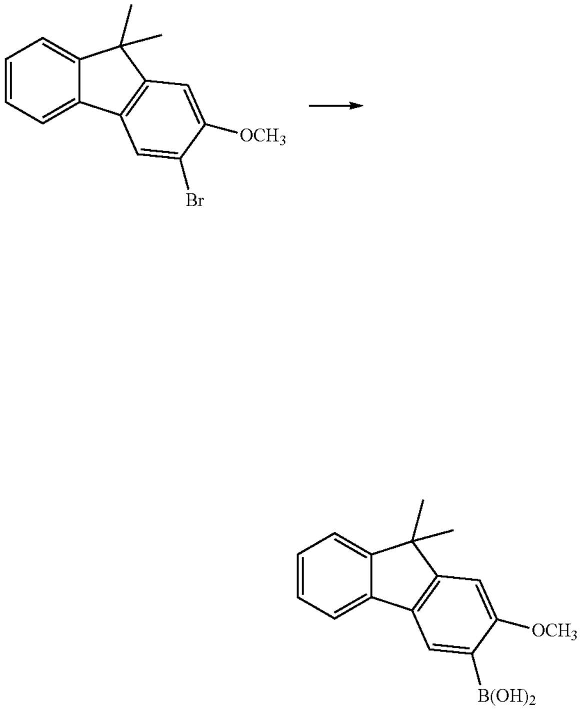

[Intermediate 3-c]

In a round-bottom flask, Intermediate 3-b (49.7 g, 164 mmol) was mixed with tetrahydrofuran (500 ml) and cooled to −78° C. under a nitrogen atmosphere, followed by slowly adding drops of 1.6 M butyl lithium (123 ml, 197 mmol). One hour later, trimethyl borate (22 ml, 214 mmol) was slowly fed into the flask, with the low temperature maintained. Subsequently, the reaction mixture was heated to room temperature and then stirred. After completion of the reaction, the organic layer was concentrated in a vacuum and recrystallized in hexane to afford Intermediate 3-c (35.6 g): yield 81%.

Synthesis Example 3-4: Synthesis of [Intermediate 3-d]

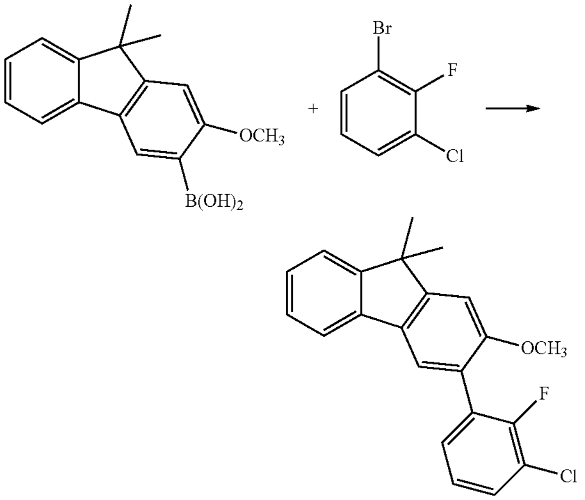

[Intermediate 3-d]

The same procedure as in Synthesis Example 1-1 were carried out, with the exception of using Intermediate 3-c and 1-bromo-3-chloro-2-fluorobenzene instead of dibenzofuran-1-boronic acid and methyl-5-bromo-2-iodobenzoate, respectively, to afford Intermediate 3-d: yield 52%

Synthesis Example 3-5: Synthesis of [Intermediate 3-e]

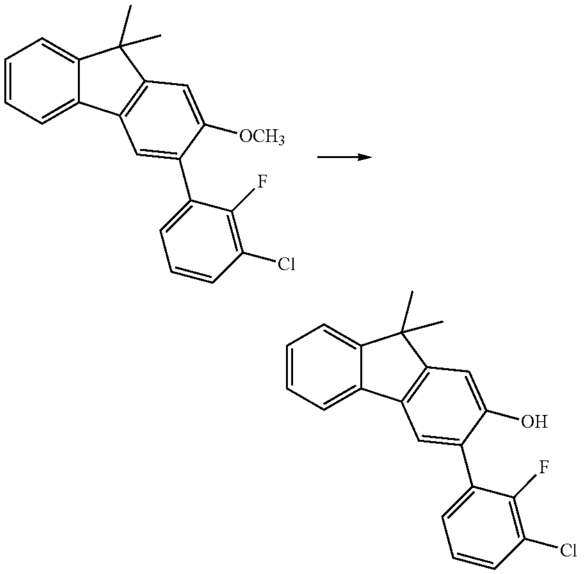

[Intermediate 3-e]

In a round-bottom flask, Intermediate 3-d (30 g, 85 mmol) and dichloromethane (300 ml) were placed under a nitrogen atmosphere, cooled to 0° C., and then slowly added with drops of a dilution of borontribromide (63.9 g, 255 mmol) in dichloromethane (150 ml). The reaction mixture was heated to room temperature and stirred for 6 hours. After completion of the reaction, the organic layer was concentrated in a vacuum. Column chromatographic separation afforded Intermediate 3-e (21.3 g): yield 74% Synthesis Example 3-6: Synthesis of [Intermediate 3-f]

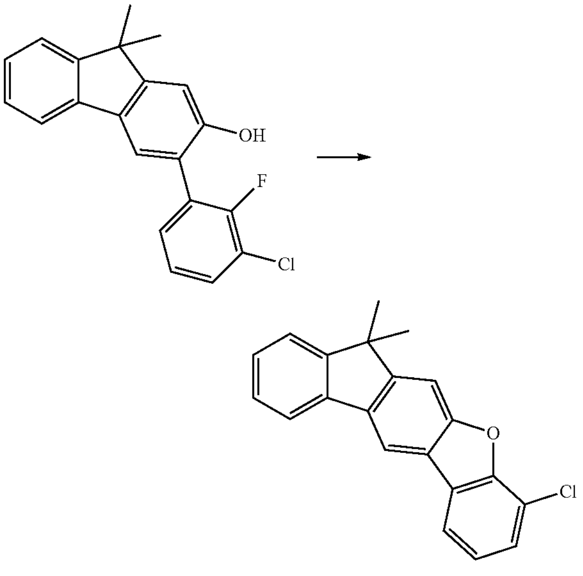

[Intermediate 3-f]

In a round-bottom flask, Intermediate 3-e (20 g, 59 mmol), potassium carbonate (13 g, 94.5 mmol), and 1-methyl-2-pyrrolidinone (200 ml) were stirred together at 150° C. for 12 hours under a nitrogen. After completion of the reaction, the organic layer was concentrated in a vacuum. Column chromatographic separation afforded Intermediate 3-f (13.5 g): yield 72% Synthesis Example 3-7: Synthesis of [Compound 67]

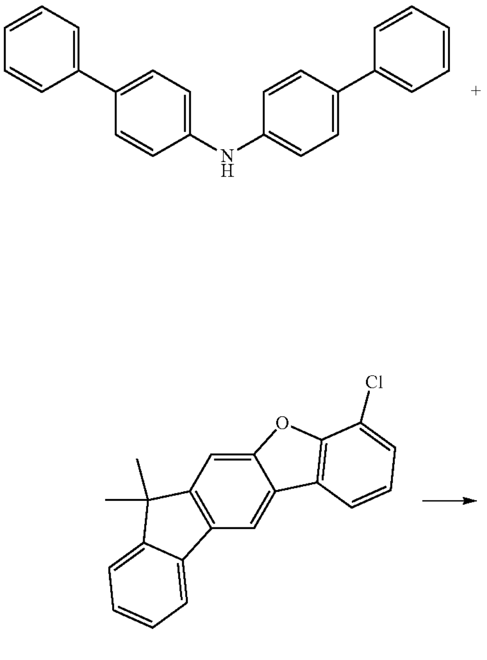

-continued

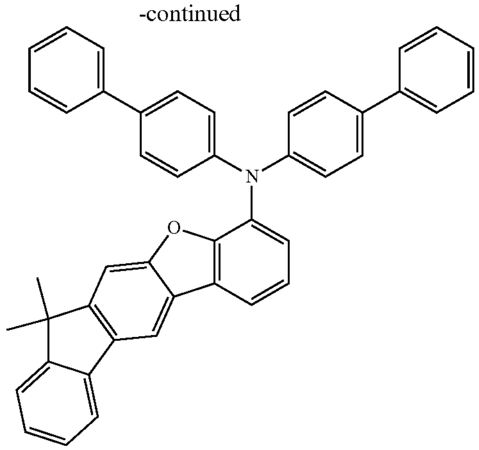

[Compound 67]

The same procedure as in Synthesis Example 1-4 was carried out, with the exception of using Intermediate 3-f instead of Intermediate 1-c, to afford Compound 67: yield 70% MS (MALDI-TOF): m/z 603.26 [M]+

Synthesis Example 4: Synthesis of [Compound 68]

Synthesis Example 4-1: Synthesis of [Intermediate 4-a]

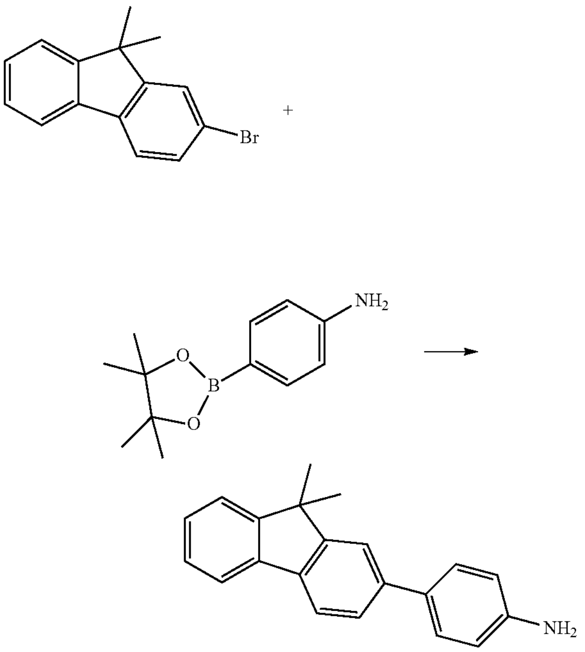

[Intermediate 4-a]

The same procedure as in Synthesis Example 1-1 was carried out, with the exception of using 4-aminophenylboronic acid pinacol ester and 2-bromo-9,9-dimethylfluorene instead of dibenzofuran-1-boronic acid and methyl-5-bromo-2-iodobenzoate, respectively, to afford Intermediate 4-a: yield 72%

Synthesis Example 4-2: Synthesis of [Intermediate 4-b]

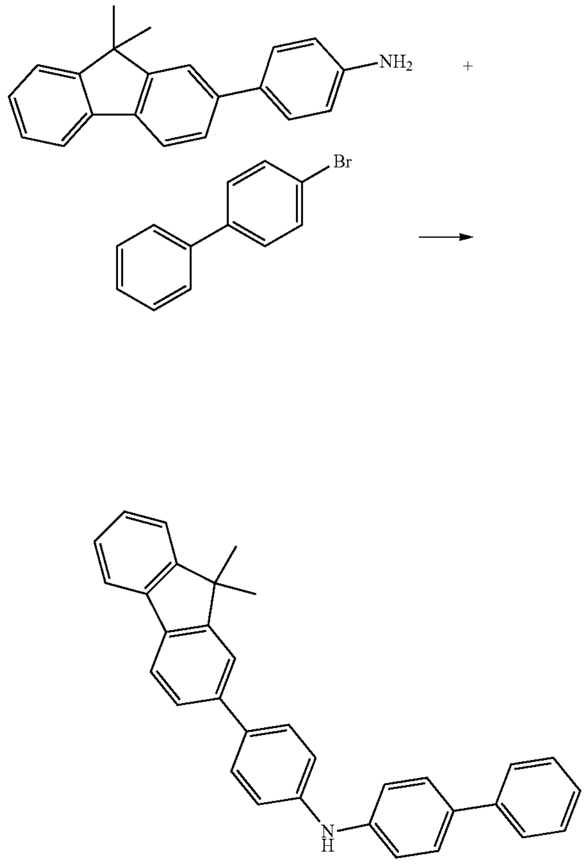

[Intermediate 4-b]

In a 250-ml reactor, Intermediate 4-a (7.0 g, 24.6 mmol), 4-bromobiphenyl (7.0 g, 30 mmol), palladium acetate (0.4 g, 0.3 mmol), sodium tert-butoxide (4.2 g, 43 mmol), tri-tert-butylphosphine (0.1 g, 0.3 mmol), and toluene (100 ml) were stirred together under reflux for 13 hours. After completion of the reaction, the reaction mixture was filtered, and the filtrate was concentrated, and separated by column chromatography to afford Intermediate 4-b (7.0 g): yield 65%

Synthesis Example 4-3: Synthesis of [Compound 68]

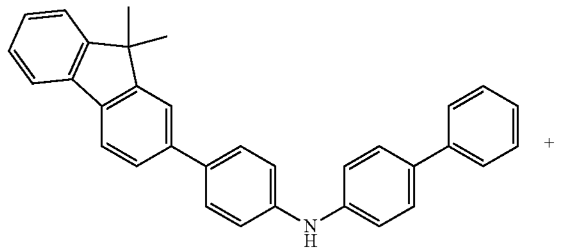

-continued

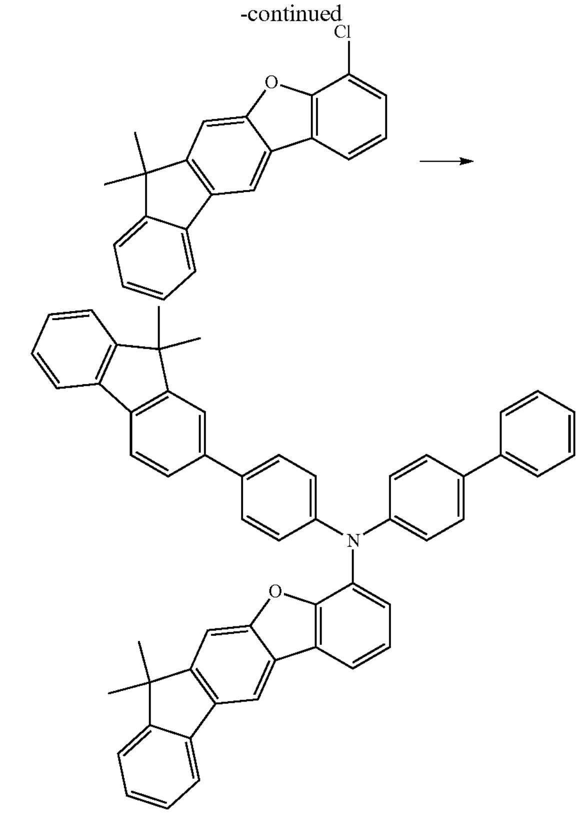

[Compound 68]

The same procedure as in Synthesis Example 1-4 was carried out, with the exception of using Intermediate 4-b and Intermediate 3-f instead of bis(4-biphenyl)amine and Intermediate 1-c, respectively, to afford [Compound 68]: yield 73% MS (MALDI-TOF): m/z 719.32 [M]+

Synthesis Example 5: Synthesis of [Compound 111]

Synthesis Example 5-1: Synthesis of [Intermediate 5-a]

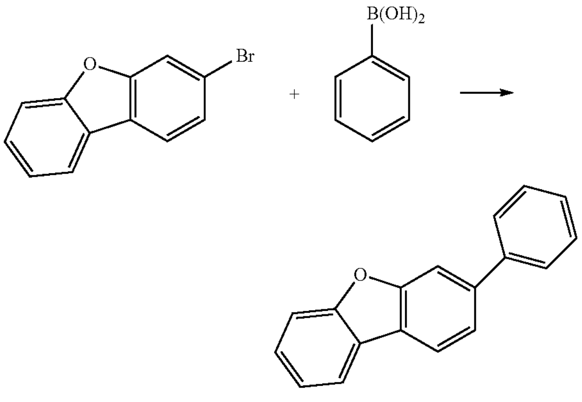

[Intermediate 5-a]

The same procedure as in Synthesis Example 1-1 was carried out, with the exception of using phenylboronic acid and 3-bromodibenzofuran instead of dibenzofuran-1-boronic acid and methyl-5-bromo-2-iodobenzoate, respectively, to afford [Intermediate 5-a]: yield 76%

Synthesis Example 5-2: Synthesis of [Intermediate 5-b]

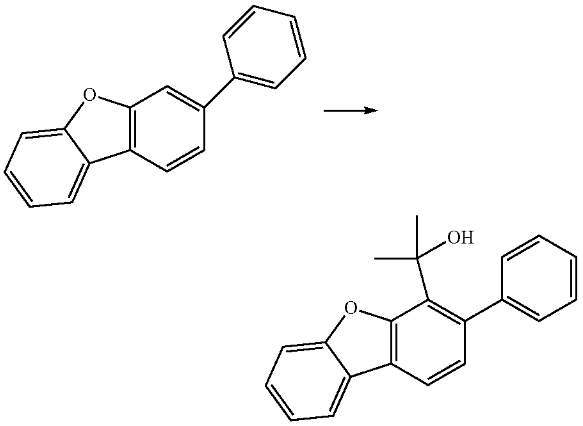

[Intermediate 5-b]

In a round-bottom flask, Intermediate 5-a (50 g, 204 mmol) and tetrahydrofuran (500 ml) were placed, cooled to −78° C., and slowly added with drops of 1.6 M-butyl lithium (128 ml, 204 mmol) before stirring for 1 hours. Drops of acetone (14.3 g, 245 mmol) was slowly added, followed by stirring at room temperature for 6 hours. After completion of the reaction, an aqueous ammonium chloride solution (50 ml) was added to split layers. The organic layer was concentrated in a vacuum and separated by chromatography to afford Intermediate 5-b (38.3 g): yield 62%

Synthesis Example 5-3: Synthesis of [Intermediate 5-c]

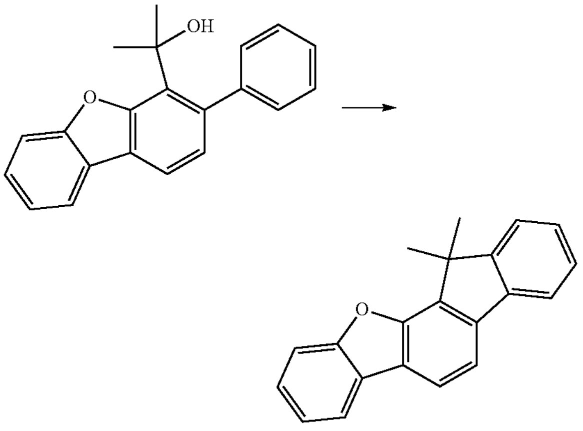

[Intermediate 5-c]

The same procedure as in Synthesis Example 1-3 was carried out, with the exception of using Intermediate 5-b instead of Intermediate 1-b, to afford Intermediate 5-c: yield 69%

Synthesis Example 5-4: Synthesis of [Intermediate 5-d]

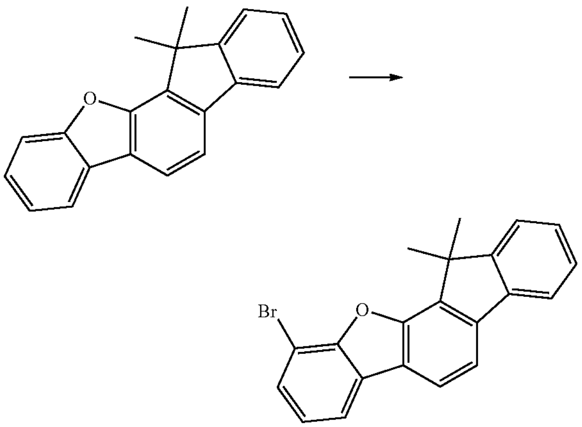

[Intermediate 5-d]

In a round-bottom flask, Intermediate 5-c (14.5 g, 50.9 mmol) was placed and then added with tetrahydrofuran (159 ml) under a nitrogen atmosphere. After the mixture was cooled to −78° C., drops of 1.6 M butyl lithium (35 ml, 56 mmol) were slowly added. After one hour, trimethyl borate (6.3 ml, 61.1 mmol) was slowly added while the low temperature was maintained. Subsequently, stirring was conducted while the temperature was elevated to room temperature. After completion of the reaction, the organic layer was concentrated in a vacuum and then recrystallized in hexane to afford Intermediate 5-d (14.8 g): yield 80%

Synthesis Example 5-5: Synthesis of [Compound 111]

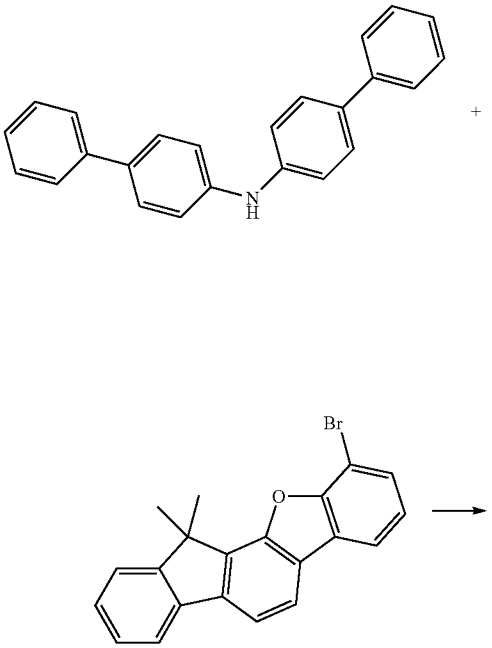

-continued

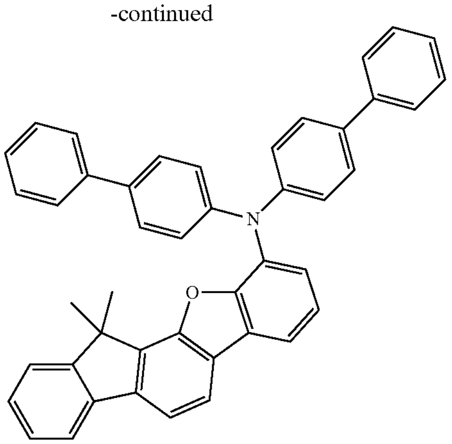

[Compound 111]

The same procedure as in Synthesis Example 1-4 was carried out, with the exception of using [Intermediate 5-d] instead of [Intermediate 1-c], to afford Compound 111: yield 70% MS (MALDI-TOF): m/z 603.26 [M]+

Synthesis Example 6: Synthesis of [Compound 120]

Synthesis Example 6-1: Synthesis of [Intermediate 6-a]

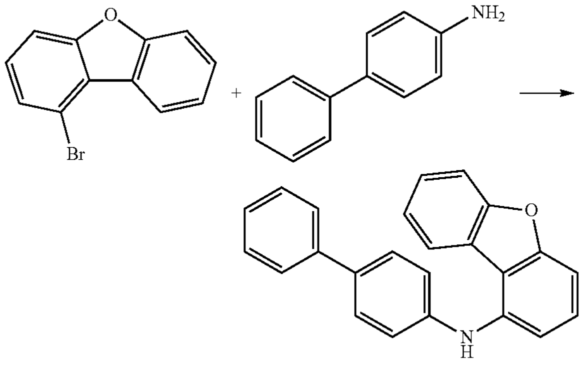

[Intermediate 6-a]

The same procedure as in Synthesis Example 4-2 was carried out, with the exception of using 4-aminobiphenyl and 1-bromodibenzofuran instead of Intermediate 4-a and 4-bromobiphenyl, respectively, to afford Intermediate 6-a: yield 58%

Synthesis Example 6-2: Synthesis of [Compound 120]

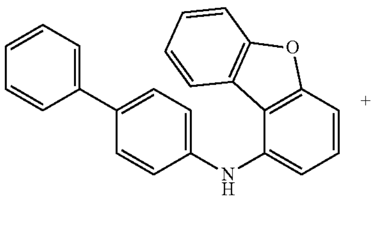

-continued

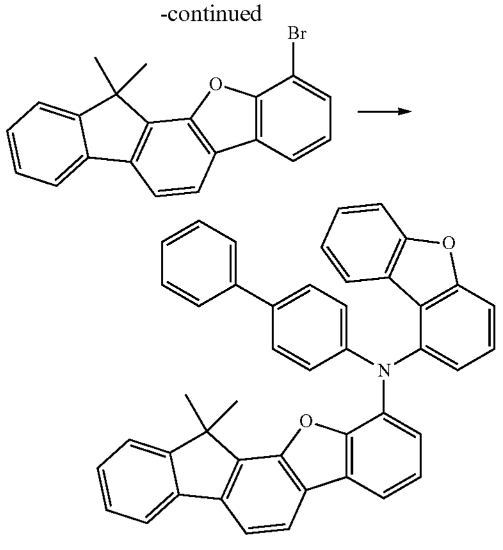

[Compound 120]

The same procedure as in Synthesis Example 1-4 was carried out, with the exception of using Intermediate 6-a and Intermediate 5-d instead of bis(4-biphenyl)amine and Intermediate 1-c, respectively, to afford Compound 120: yield 70%

MS (MALDI-TOF): m/z 617.24 [M]+

Synthesis Example 7: Synthesis of [Compound 136]

Synthesis Example 7-1: Synthesis of [Intermediate 7-a]

[Intermediate 7-a]

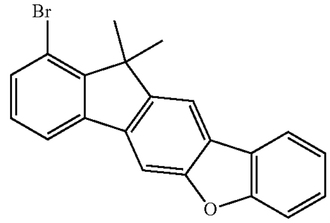

The same procedures as in Synthesis Examples 1-1 to 1-3 were carried out, with the exception of using dibenzofuran-3-boronic acid instead of dibenzofuran-1-boronic acid in Synthesis Example 1-1 and methyl-5-bromo-1-iodobenzoate boronic acid instead of methyl-5-bromo-2-iodobenzoate, to afford Intermediate 7-a: yield 70%

Synthesis Example 7-2: Synthesis of [Compound 136]

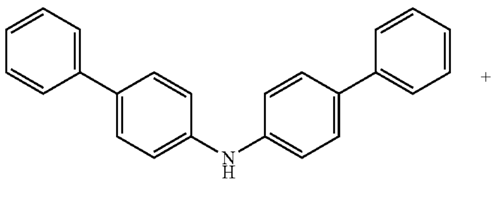

-continued

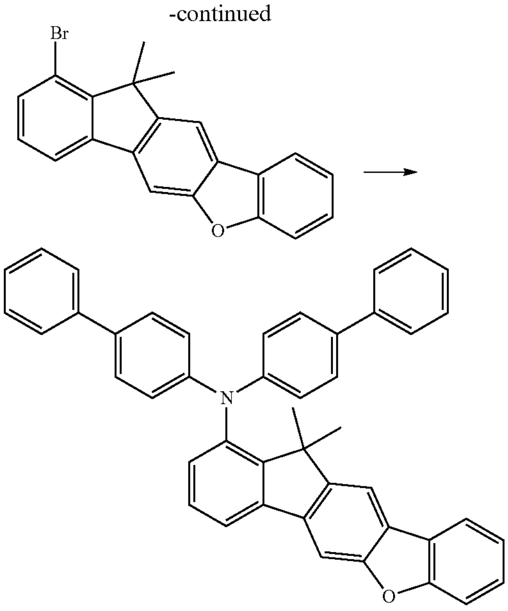

[Compound 136]

The same procedure as in Synthesis Example 1-4 was carried out, with the exception of using Intermediate 7-a instead of Intermediate 1-c, to afford Compound 136: yield 72% MS (MALDI-TOF): m/z 603.26 [M]+

Synthesis Example 8: Synthesis of [Compound 141]

Synthesis Example 8-1: Synthesis of [Intermediate 8-a]

[Intermediate 8-a]

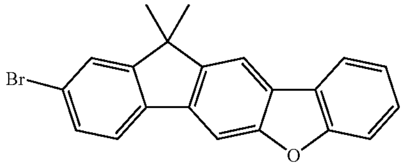

The same procedures as in Synthesis Examples 1-1 to 1-3 were carried out, with the exception of using dibenzofuran-3-boronic acid instead of dibenzofuran-1-boronic acid in Synthesis Example 1-1, to afford Intermediate 8-a: yield 68%

Synthesis Example 8-2: Synthesis of [Compound 141]

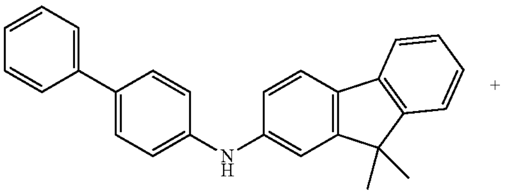

-continued

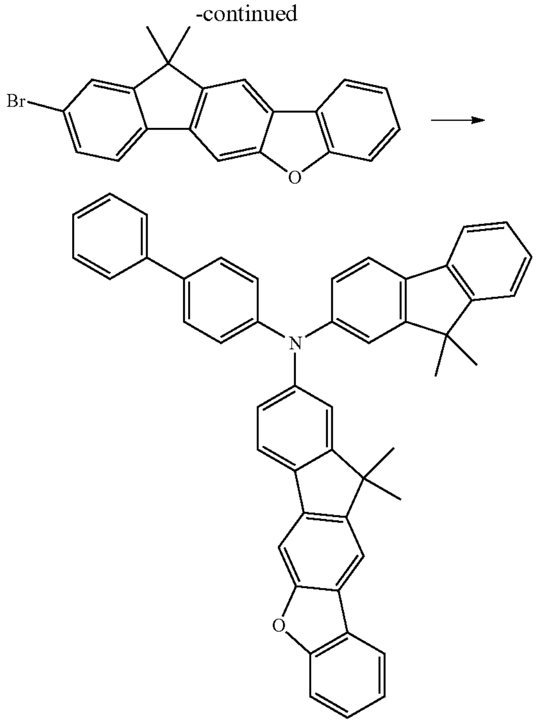

[Compound 141]

The same procedure as in Synthesis Example 1-4 was carried out, with the exception of using N-(4-biphenyl)-(9,9-dimethylfluoren-2-yl)amine and Intermediate 8-a instead of bis(4-biphenyl)amine and Intermediate 1-c, respectively, to afford Compound 141: yield 75% MS (MALDI-TOF): m/z 643.29 [M]+

Synthesis Example 9: Synthesis of [Compound 181]

Synthesis Example 9-1: Synthesis of [Intermediate 9-a]

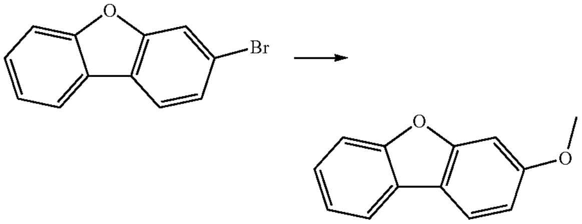

[Intermediate 9-a]

In a round-bottom flask, 3-bromodibenzofuran (50 g, 202 mmol), an aqueous sodium methoxide solution (54.6 g, 1214 mmol), copper iodide (11.5 g, 60.7 mmol), and methanol (200 ml) were fluxed for 12 hours under a nitrogen atmosphere. After completion of the reaction, the organic layer was concentrated in a vacuum. Column chromatographic separation afforded Intermediate 9-a (36 g): yield 90%

Synthesis Example 9-2: Synthesis of [Intermediate 9-b]

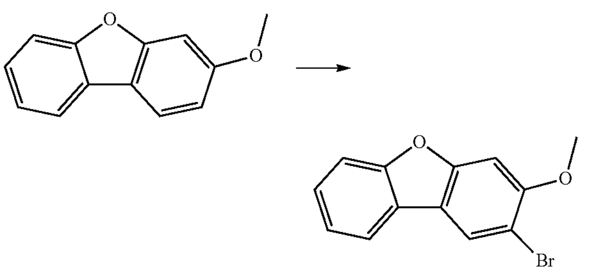

[Intermediate 9-b]

In a round-bottom flask, Intermediate 9-a (36 g, 181 mmol), N-bromosuccinimide (32.3 g, 181 mmol), and dimethyl formamide (700 ml) were stirred together at 50° C. for 12 hours under a nitrogen atmosphere. After completion of the reaction, the organic layer was concentrated in a vacuum. Column chromatographic separation afforded Intermediate 9-b (35 g): yield 70%

Synthesis Example 9-3: Synthesis of [Intermediate 9-c]

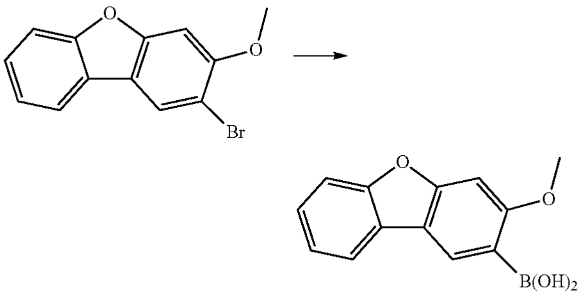

[Intermediate 9-c]

The same procedure as in Synthesis Example 3-3 was carried out, with the exception of using Intermediate 9-b instead of Intermediate 3-b, to afford Intermediate 9-c: yield 78%

Synthesis Example 9-4: Synthesis of [Intermediate 9-d]

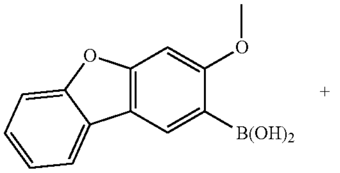

-continued

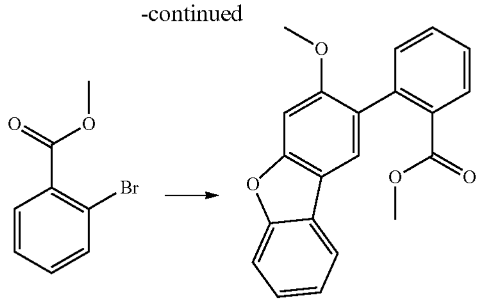

[Intermediate 9-d]

The same procedure as in Synthesis Example 1-1 was carried out, with the exception of using Intermediate 9-c and methyl-2-bromobenzoate instead of dibenzofuran-1-boronic acid and methyl-5-bromo-2-iodobenzoate, respectively, to afford Intermediate 9-d: yield 64%

Synthesis Example 9-5: Synthesis of [Intermediate 9-e]

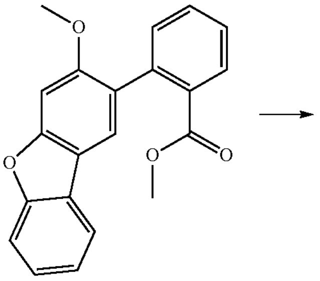

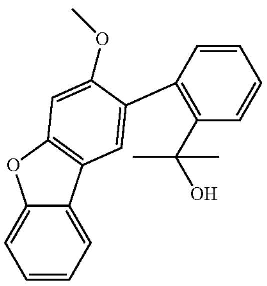

[Intermediate 9-e]

The same procedure as in Synthesis Example 1-2 was carried out, with the exception of using Intermediate 9-d instead of Intermediate 1-a, to afford Intermediate 9-e: yield 77%

Synthesis Example 9-6: Synthesis of [Intermediate 9-f]

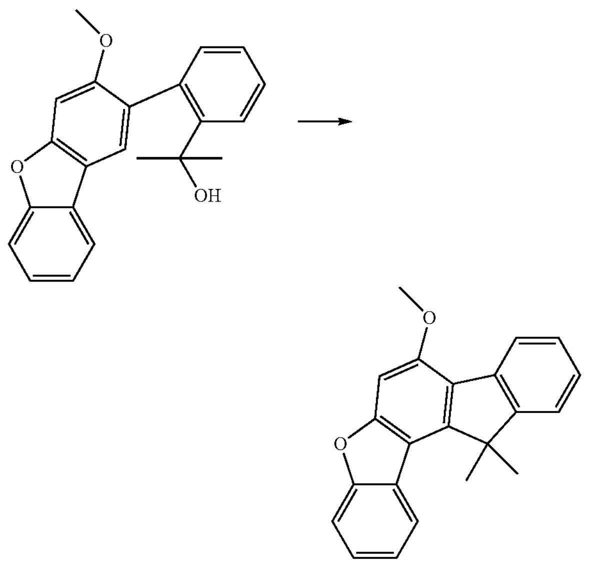

[Intermediate 9-f]

The same procedure as in Synthesis Example 1-3 was carried out, with the exception of using Intermediate 9-e instead of Intermediate 1-b, to afford Intermediate 9-f: yield 67%

Synthesis Example 9-7: Synthesis of [Intermediate 9-g]

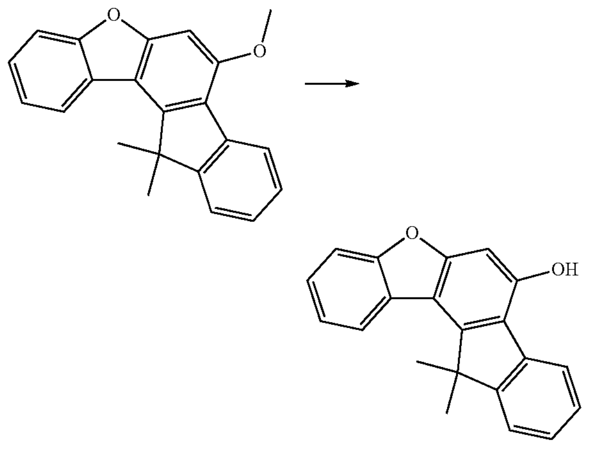

[Intermediate 9-g]

In a round-bottom flask, Intermediate 9-f (30 g, 95.4 mmol) and dichloromethane (200 ml) were mixed and cooled to 0° C. A dilution of brontribromide (120 g, 143 mmol) in dichloromethane (300 mL) was dropwise added slowly into the flask and then stirred at room temperature for 3 hours. After completion of the reaction, the reaction mixture was poured into distilled water (1 L) and the organic layer thus formed was concentrated in a vacuum and separated by column chromatography to afford Intermediate 9-g (19.2 g): yield 67%

Synthesis Example 9-8: Synthesis of [Intermediate 9-h]

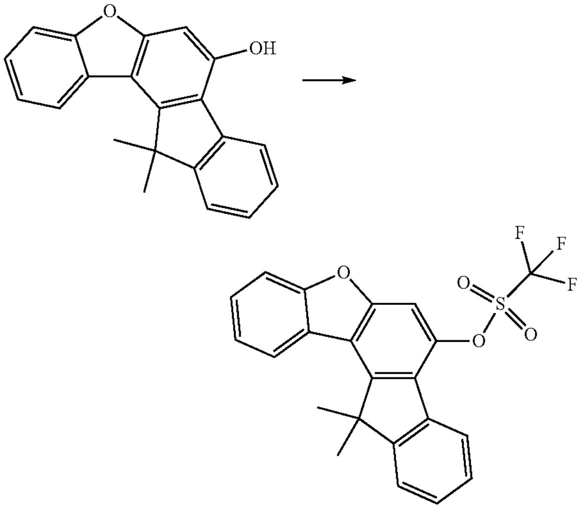

[Intermediate 9-h]

In a round-bottom flask, Intermediate 9-g (10 g, 33.2 mmol) was cooled to 0° C. under a nitrogen atmosphere. Pyridine (3.2 ml, 39.9 mmol) and trifluoromethane sulfonic anhydride (7.3 ml, 43.2 mmol) were dropwise added slowly, followed by stirring at room temperature for 2 hours. After completion of the reaction, the organic layer was concentrated in a vacuum. Column chromatographic separation afforded Intermediate 9-h (12.2 g): yield 85%

Synthesis Example 9-9: Synthesis of [Compound 181]

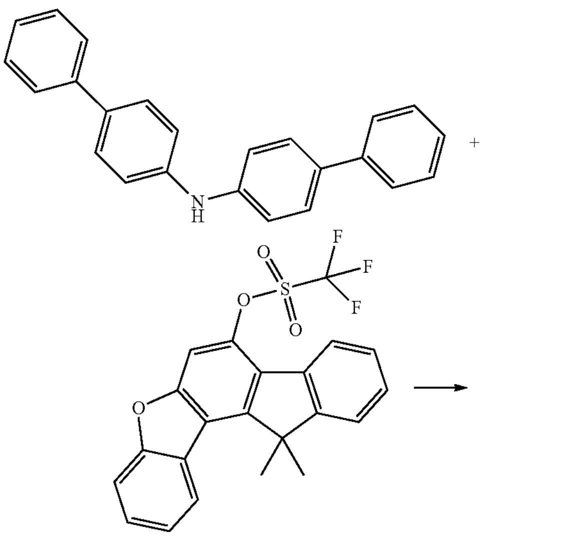

-continued

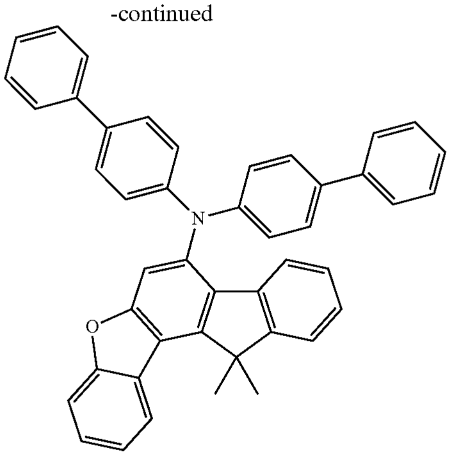

[Compound 181]

Intermediate 9-h (17.3 g, 40 mmol), bis(4-biphenyl)amine (19.3 g, 60 mmol), palladium acetate (0.5 g, 2 mmol), BINAP (1.9 g, 3 mmol), sodium tert-butoxide (5.8 g, 60 mmol), and toluene (200 ml) were fed into a round-bottom flask under a nitrogen atmosphere, stirred at room temperature for 30 min, and heated at 120° C. for 12 hours under reflux. After completion of the reaction, the organic layer was concentrated in a vacuum. Column chromatographic separation afforded Compound 181 (14.7 g): yield 61% MS (MALDI-TOF): m/z 603.26[M]+

Synthesis Example 10: Synthesis of [Compound 183]

Synthesis Example 10-1: Synthesis of [Intermediate 10-a]

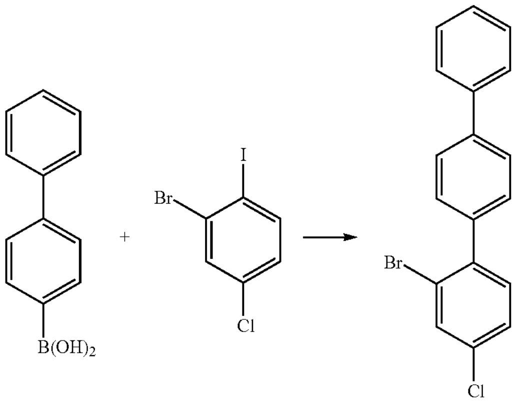

[Intermediate 10-a]

The same procedure as in Synthesis Example 1-1 was carried out, with the exception of using biphenyl-4-boronic acid and 2-bromo-4-chloroiodobenzene instead of dibenzofuran-1-boronic acid and methyl-5-bromo-2-iodobenzoate, respectively, to afford Intermediate 10-a: yield 74%

Synthesis Example 10-2: Synthesis of [Intermediate 10-b]

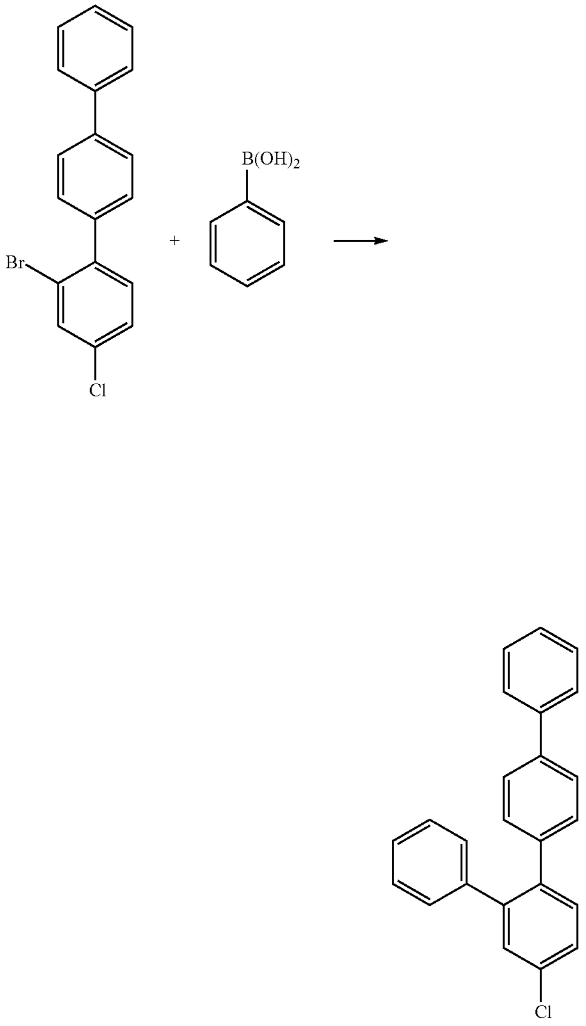

[Intermediate 10-b]

The same procedure as in Synthesis Example 1-1 was carried out, with the exception of using phenyl boronic acid and Intermediate 10-a instead of dibenzofuran-1-boronic acid and methyl-5-bromo-2-iodobenzoate, to afford [Intermediate 10-b]: yield 75%

Synthesis Example 10-3: Synthesis of [Intermediate 10-c]

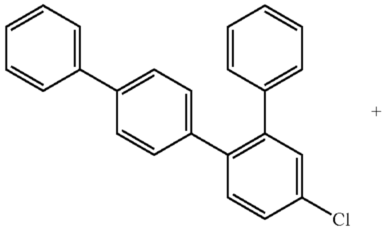

-continued

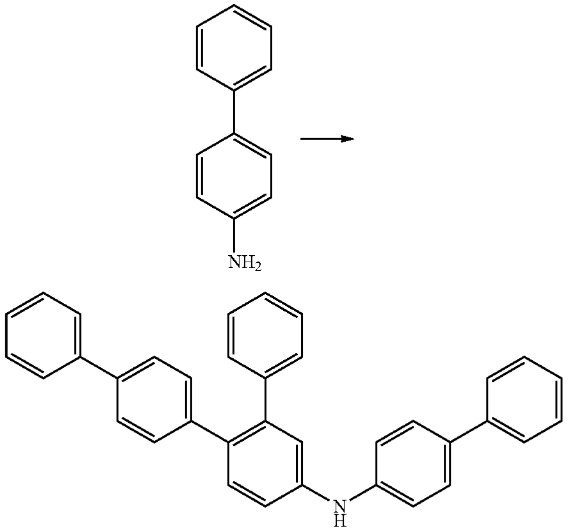

[Intermediate 10-c]

The same procedure as in Synthesis Example 4-2 was carried out, with the exception of using 4-aminobiphenyl and Intermediate 10-b instead of Intermediate 4-a and 4-bromobiphenyl, respectively, to afford Intermediate 10-c: yield 54%

Synthesis Example 10-4: Synthesis of [Compound 183]

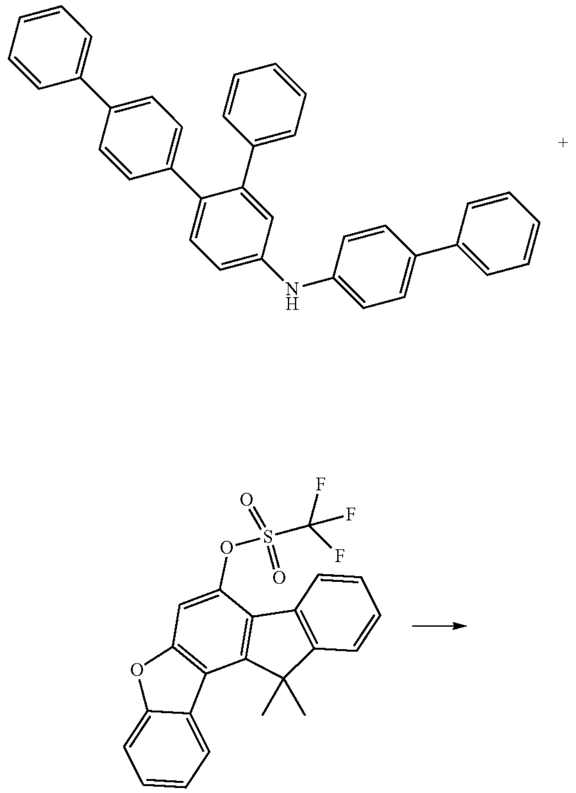

-continued

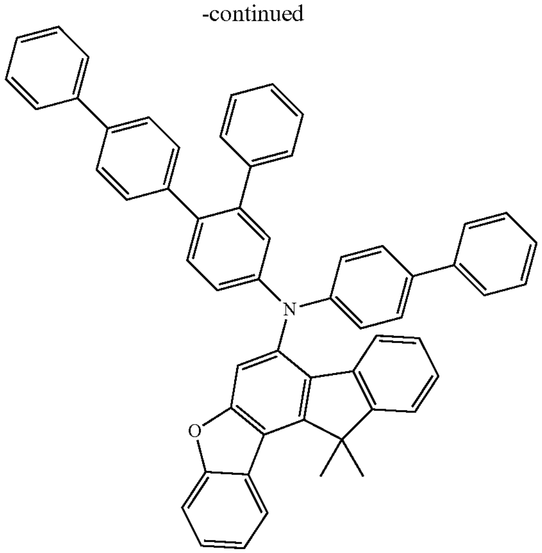

[Compound 183]

The same procedure as in Synthesis Example 9-9 was carried out, with the exception of using Intermediate 10-c instead of bis(4-biphenyl)amine, to afford Compound 183: yield 67% MS (MALDI-TOF): m/z 755.32[M]+

Synthesis Example 11: Synthesis of [Compound 238]

Synthesis Example 11-1: Synthesis of [Intermediate 11-a]

[Intermediate 11-a]

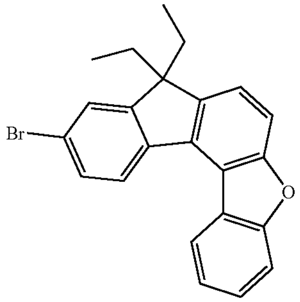

The same procedures as in Synthesis Examples 1-2 to 1-3 were carried out, with the exception of using 3 M-ethyl magnesium bromide instead of 3 M-methyl magnesium bromide in Synthesis Example 1-2, to afforded Intermediate 11-a: yield 67%

Synthesis Example 11-2: Synthesis of [Compound 238]

The same procedure as in Synthesis Example 1-4 was carried out, with the exception of using bis(3-biphenylyl) amine and Intermediate 11-a instead of bis(4-biphenyl) amine and Intermediate 1-c, respectively, to afford [Compound 238]: yield 75%

MS (MALDI-TOF): m/z 631.29 [M]+

Synthesis Example 12: Synthesis of [Compound 254]

Synthesis Example 12-1: Synthesis of [Intermediate 12-a]

[Intermediate 12-a]

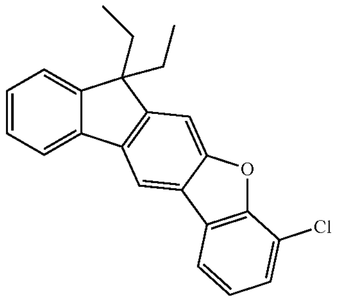

The same procedures as in Synthesis Examples 3-1 to 3-6 were carried out, with the exception of using 2-bromo-9,9-diethylfluorene instead of 2-bromo-9,9-dimethylfluorene in Synthesis Example 3-1, to afford Intermediate 12-a: yield 70%

Synthesis Example 12-2: Synthesis of [Compound 254]

The same procedure as in Synthesis Example 1-4 was carried out, with the exception of using N-phenyl-4-biphenylamine and Intermediate 12-a instead of bis(4-biphenyl) amine and Intermediate 1-c, to afford Compound 254: yield 75%

MS (MALDI-TOF): m/z 555.26 [M]+

Synthesis Example 13: Synthesis of [Compound 262]

Synthesis Example 13-1: Synthesis of [Intermediate 13-a]

[Intermediate 13-a]

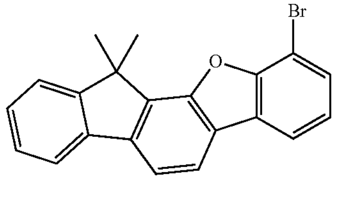

The same procedures as in Synthesis Examples 5-2 to 5-4 was carried out, with the exception of using 2,4-dimethyl-3-pentanone instead of acetone in Synthesis Example 5-2, to afford Intermediate 13-a: yield 50%

Synthesis Example 13-2: Synthesis of [Compound 262]

The same procedure as in Synthesis Example 1-4 was carried out, with the exception of using 4-methyldiphenylamine and 13-a instead of bis(4-biphenyl)amine and Intermediate 1-c, respectively, to afford Compound 262: yield 72%

MS (MALDI-TOF): m/z 610.30 [M]+

Synthesis Example 14: Synthesis of [Compound 268]

Synthesis Example 14-1: Synthesis of [Intermediate 14-a]

[Intermediate 14-a]

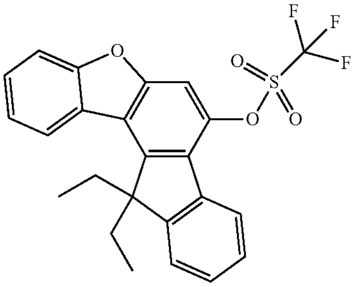

The same procedures as in Synthesis Examples 9-6 to 9-8 were carried out, with the exception of using 3 M-ethyl magnesium bromide instead of 3 M-methyl magnesium bromide in Synthesis Example 1-2 and Intermediate 9-d instead of Intermediate 1-a, to afford Intermediate 14-a: yield 55%

Synthesis Example 14-2: Synthesis of [Compound 268]

The same procedure as in Synthesis Example 1-4 was carried out, with the exception of using N-(4-biphenyl)-(9,9-dimethylfluoren-2-yl)amine and Intermediate 14-a instead of bis(4-biphenyl)amine and Intermediate 1-c, respectively, to afford Compound 268: yield 74%

MS (MALDI-TOF): m/z 671.32 [M]+

Synthesis Example 15: Synthesis of [Compound 317]

Synthesis Example 15-1: Synthesis of [Intermediate 15-a]

[Intermediate 15-a]

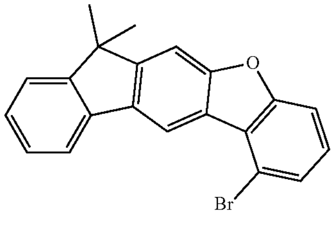

The same procedure as for Intermediate 306 in Synthesis Example 3-6 was carried out, with the exception of using 1-bromo-2-iodo-3-fluorobenzene instead of 1-bromo-3-chloro-2-fluorobenzene in Synthesis Example 3-4, to afford Intermediate 15-a: yield 52%

Synthesis Example 15-2: Synthesis of [Compound 317]

The same procedure as in Synthesis Example 1-4 was carried out, with the exception of using N-phenyl-4-biphenylamine and Intermediate 15-a instead of bis(4-biphenyl) amine and Intermediate 1-c, to afford Compound 317: yield 74%

MS (MALDI-TOF): m/z 671.32 $[M]^+$

Synthesis Example 16: Synthesis of [Compound 321]

Synthesis Example 16-1: Synthesis of [Intermediate 16-a]

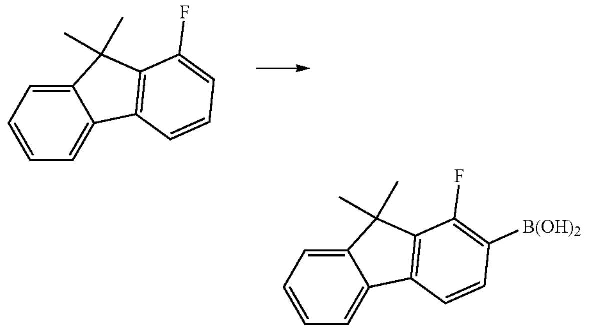

Intermediate 16-a

In a round-bottom flask was placed 1-fluoro-9,9'-dimethylfluorene (50 g, 235 mmol) to which tetrahydrofuran (500 ml) was then added under a nitrogen atmosphere. The mixture was cooled to −78° C. and slowly added with drops of 1.6 M butyl lithium (161 ml, 259 mmol). The temperature was elevated to room temperature before stirring for 4 hours. Then, the temperature was lowered again to −78° C., and trimethylborate (32 ml, 282 mmol) was slowly added while the low temperature was maintained. Following temperature elevation to room temperature, the reaction mixture was stirred. After completion of the reaction, the organic layer was concentrated in a vacuum and recrystallized in hexane to afford Intermediate 16-a (45 g): yield 75%.

Synthesis Example 16-2: Synthesis of [Intermediate 16-b]

[Intermediate 16-b]

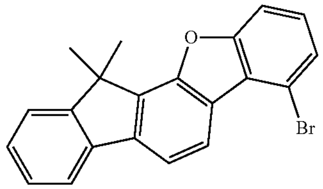

The same procedure as for Intermediate 3-f in Synthesis Example 3-6 was carried out, with the exception of using 1-bromo-2-iodo-3-fluorobenzene instead of 1-bromo-3-chloro-2-fluorobenzene in Synthesis Example 3-4, to afford Intermediate 16-b: yield 50%

Synthesis Example 16-3: Synthesis of [Compound 321]

The same procedure as in Synthesis Example 1-4 was carried out, with the exception of using N-phenyl-4-biphenylamine and Intermediate 16-b instead of bis(4-bipheneyl) amine and Intermediate 1-c in Synthesis Example 1-4, respectively, to afford Compound 321: yield 71%

Synthesis Example 17: Synthesis of [Compound 325]

Synthesis Example 17-1: Synthesis of [Intermediate 17-a]

[Intermediate 17-a]

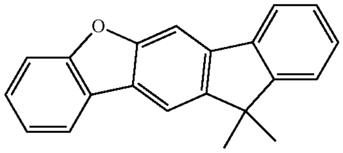

The same procedures as in Synthesis Examples 1-1 and 1-3 were carried out, with the exception of using dibenzofuran-3-boronic acid and methyl-2-bromobenzoate instead of dibenzofuran-1-boronic acid and methyl-2-bromobenzoate in Synthesis Example 1-1, respectively, to afford Intermediate 17-a: yield 70%

Synthesis Example 17-2: Synthesis of [Intermediate 17-b]

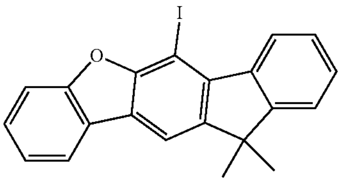 [SMILES: CC1(C)c2ccccc2-c2c1cc1c(oc3ccccc31)c2I]

The same procedure as in Synthesis Example 16-1 was carried out, with the exception of using Intermediate 17-a instead of 1-fluoro-9,9'-dimethylfluorene, to afford Intermediate 17-b: yield 74%

Synthesis Example 17-3: Synthesis of [Compound 325]

The same procedure as in Synthesis Example 1-4 was carried out, with the exception of using N-phenyl-4-biphenylamine and Intermediate 17-b instead of bis(4-biphenyl) amine and Intermediate 1-c, respectively, to afford Compound 325: yield 71%

Examples 1 TO 17: Fabrication of Organic Light-Emitting Diode

An ITO glass substrate was patterned to have a translucent area of 2 mm×2 mm and cleansed. The ITO glass was mounted in a vacuum chamber that was then set to have a base pressure of $1\times10^{-6}$ torr. On the ITO glass substrate, HATCN (50 Å) was deposited, followed by one of the compounds prepared according to the present disclosure, as listed in Table 1, below, for a hole transport layer (650 Å). Then, a light-emitting layer 200 Å thick was formed by doping with 5% of a blue host (BH)+blue dopant (BD). Subsequently, deposition was made with compound ET:Liq=1:1 (300 Å) for an electron transport layer, Liq (10 Å) for an electron injection layer, and Al (1,000 Å). The light-emitting diodes thus obtained were measured at 0.4 mA for luminescence properties. Structures of [HATCN], [BH], [BD], [ET], and [Liq] are as follows:

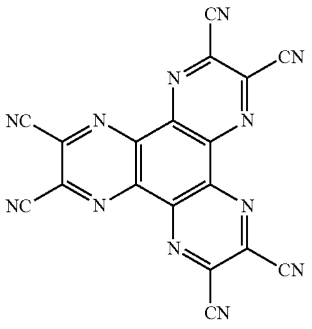

[HATCN]

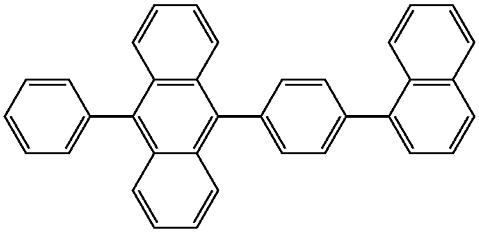

[BH]

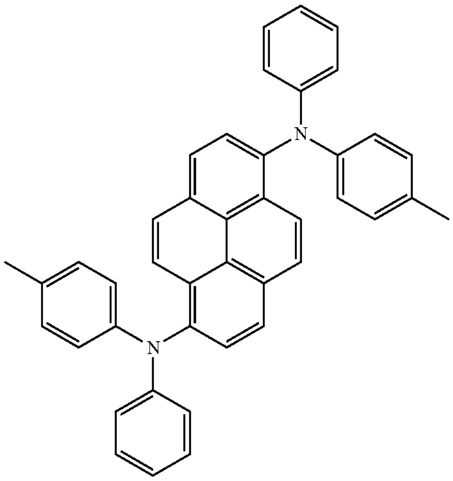

[BD]

-continued

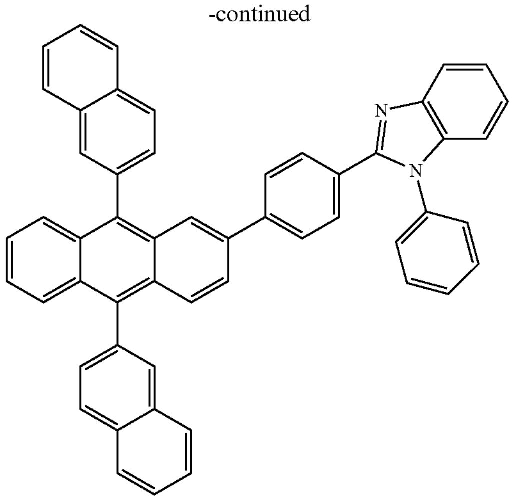

[ET]

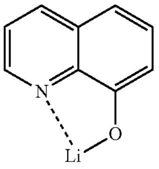

[Liq]

Comparative Example 1

An organic light-emitting diode was fabricated in the same manner as in Examples 1 to 17, with the exception of using, instead of the compounds prepared in the present disclosure, NPD which is conventionally widely used as a hole transport layer material.

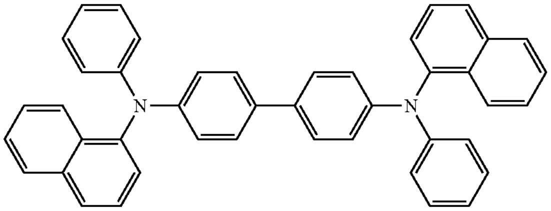

[NPD]

The organic EL devices fabricated in the Examples 1 to 17 and Comparative Example 1 were measured for voltage, luminance, color coordinates, and lifespan, and the results are summarized in Table 1, below.

Here, T95 refers to the time for luminance to decrease to 95 of the initial luminance (2000 cd/m2).

TABLE 1

| | HTL | V | Cd/A | CIEx | CIEy | T95 (Hrs) |
|---|---|---|---|---|---|---|
| C. Ex. 1 | NPD | 4.2 | 6.3 | 0.133 | 0.129 | 13 |
| Ex. 1 | Chemical Formula 1 | 3.6 | 8.0 | 0.132 | 0.130 | 35 |
| Ex. 2 | Chemical Formula 3 | 3.7 | 7.8 | 0.133 | 0.128 | 33 |
| Ex. 3 | Chemical Formula 67 | 3.4 | 8.0 | 0.132 | 0.126 | 34 |
| Ex. 4 | Chemical Formula 68 | 3.6 | 7.9 | 0.133 | 0.125 | 37 |
| Ex. 5 | Chemical Formula 111 | 3.8 | 8.0 | 0.133 | 0.125 | 43 |
| Ex. 6 | Chemical Formula 120 | 3.7 | 7.9 | 0.132 | 0.126 | 40 |

TABLE 1-continued

| | HTL | V | Cd/A | CIEx | CIEy | T95 (Hrs) |
|---|---|---|---|---|---|---|
| Ex. 7 | Chemical Formula 136 | 3.7 | 7.8 | 0.132 | 0.130 | 34 |
| Ex. 8 | Chemical Formula 141 | 3.5 | 7.7 | 0.133 | 0.128 | 34 |
| Ex. 9 | Chemical Formula 181 | 3.6 | 8.1 | 0.133 | 0.125 | 40 |
| Ex. 10 | Chemical Formula 183 | 4.0 | 7.8 | 0.132 | 0.129 | 35 |
| Ex. 11 | Chemical Formula 238 | 3.8 | 7.7 | 0.132 | 0.130 | 35 |
| Ex. 12 | Chemical Formula 254 | 3.6 | 7.7 | 0.133 | 0.130 | 38 |
| Ex. 13 | Chemical Formula 262 | 3.7 | 7.8 | 0.133 | 0.128 | 36 |
| Ex. 14 | Chemical Formula 268 | 3.6 | 7.9 | 0.132 | 0.129 | 40 |
| Ex. 15 | Chemical Formula 317 | 3.6 | 7.8 | 0.133 | 0.126 | 60 |
| Ex. 16 | Chemical Formula 321 | 3.7 | 7.9 | 0.132 | 0.129 | 55 |
| Ex. 17 | Chemical Formula 324 | 3.6 | 8.0 | 0.133 | 0.125 | 56 |

Compared to the conventional hole transport layer material NPD, the organic compounds prepared according to the present disclosure guarantee higher efficiency, lower driving voltages, and longer lifespans for the OLED, as understood from the data of Table 1, and thus can be applied to the fabrication of organic light-emitting diodes having improved properties.

Particularly, more improved lifespan properties were detected in Examples to 17 than the other Examples of Examples 1 to 17.

Comparative Example 2: Fabrication of Organic Light-Emitting Diode

An ITO glass substrate was patterned to have a translucent area of 2 mm×2 mm and cleansed. The ITO glass substrate was mounted in a vacuum chamber that was then set to have a base pressure of $1\times10^{-6}$ torr. On the ITO glass substrate, HATCN (50 Å) was deposited, followed by NPD (900 Å). Then, a light-emitting layer 300 Å thick was formed by doping the host material CBP and a green phosphorescent dopant (GD, 7%). Subsequently, deposition was made with compound ET:Liq=1:1 (300 Å), Liq (10 Å), and Al (1,000 Å) in that order. The light-emitting diode thus obtained were measured at 0.4 mA for luminescence properties.

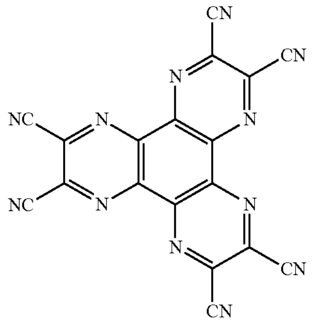

[HATCN]

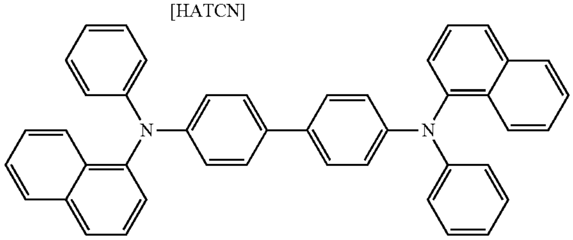

[NPD]

-continued

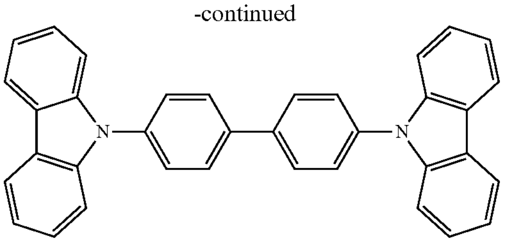

[CBP]

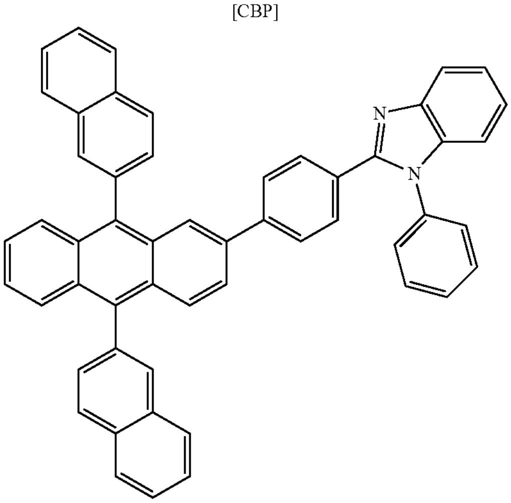

[ET]

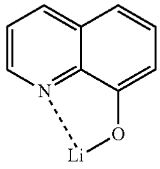

[Liq]

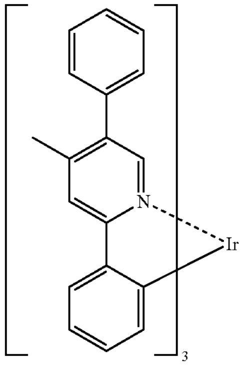

[GD ]

Comparative Example 3

An electroluminescent device was fabricated according to a conventional method using Comparative Compound 1 as a hole auxiliary layer material. First, an ITO glass substrate was patterned to have a translucent area of 2 mm×2 mm and cleansed. The ITO glass substrate was mounted in a vacuum chamber that was then set to have a base pressure of 1×10−6 torr. On the ITO glass substrate, HATCN (50 Å) was deposited, followed by NPD (550 Å). Then, a hole auxiliary layer was formed on the hole transport layer by depositing the Comparative Compound 1 (350 Å), and a light-emitting layer 300 Å thick was formed by doping the host material CBP and a green phosphorescent dopant (GD, 7%). Subsequently, deposition was made with compound ET:Liq=1:1 (300 Å), Liq (10 Å), and Al (1,000 Å) in that order. The light-emitting diode thus obtained were measured at 0.4 mA for luminescence properties.

[Comparative Compound 1]

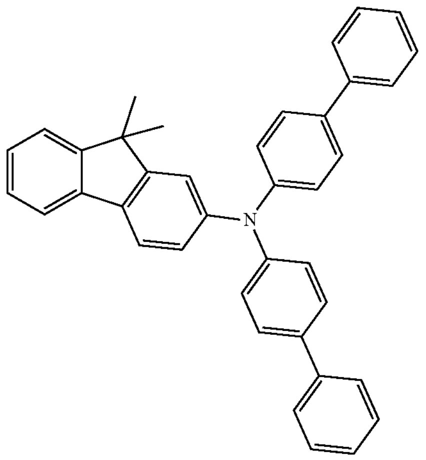

Examples 18 to 23

Organic light-emitting diodes were fabricated in the same manner as in Comparative Examples 2, with the exception of using the compounds of the present disclosure, instead of Comparative Material 1, as a hole auxiliary layer material.

TABLE 2

| | Hole auxiliary layer | V | Cd/A | CIEx | CIEy | $T_{95}$ (Hrs) |
|---|---|---|---|---|---|---|
| C. Ex. 2 | — | 6.9 | 36 | 0.335 | 0.625 | 20 |
| C. Ex. 3 | C. Compound 1 | 6.9 | 42 | 0.329 | 0.631 | 25 |
| Ex. 18 | Chemical Formula 67 | 6.9 | 51 | 0.327 | 0.632 | 41 |
| Ex. 19 | Chemical Formula 111 | 6.8 | 49 | 0.330 | 0.631 | 45 |
| Ex. 20 | Chemical Formula 181 | 7.0 | 50 | 0.337 | 0.625 | 43 |
| Ex. 21 | Chemical Formula 317 | 6.9 | 52 | 0.329 | 0.631 | 71 |
| Ex. 22 | Chemical Formula 321 | 6.8 | 53 | 0.327 | 0.632 | 65 |
| Ex. 23 | Chemical Formula 324 | 6.9 | 51 | 0.329 | 0.631 | 68 |

When used in a hole auxiliary layer, as can be seen in Table 2, the compounds obtained according to the present invention guarantee higher efficiency and longer lifespan for the device than do the compounds of Comparative Examples 2 and 3, and thus can be applied to the fabrication of organic light-emitting devices having improved characteristics.

Particularly, compounds of Examples 21 to 23 were observed to have improved longevity properties compared to the other Examples.

According to the present disclosure, the organic light-emitting diode containing the compound represented by any one of Chemical Formulas A to E in a hole transport layer thereof exhibits the outstanding properties of high efficiency, low voltage, and long lifespan, compared to existing organic light-emitting diodes.

What is claimed is:

1. An organic compound represented by the following Chemical Formula A:

[Chemical Formula A]

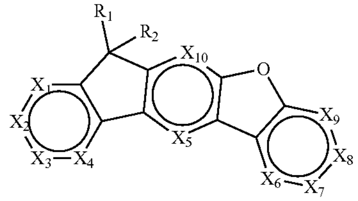

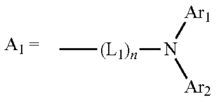

wherein,
$X_1$ is $CR_{11}$,
$X_2$ is $CR_{12}$,
$X_3$ is $CR_{13}$,
$X_4$ is $CR_{14}$,
$X_5$ is $CR_{15}$,
$X_6$ is a carbon atom connected to $A_1$,
$X_7$ is $CR_{17}$,
$X_8$ is $CR_{18}$,
$X_9$ is $CR_{19}$ and
$X_{10}$ is $CR_{20}$,
wherein the organic compound represented by Chemical Formula A has $A_1$ bonded to position 1 of the dibenzofuran moiety thereof in such a manner that $A_1$ is bonded to carbon atom of $X_6$ in Chemical Formula A,
the substituents $R_1$ and $R_2$, which may be the same or different, are each independently selected from the group consisting of a substituted or unsubstituted alkyl of 1 to 30 carbon atoms and a substituted or unsubstituted cycloalkyl of 3 to 30 carbon atoms,
wherein $R_{11}$ to $R_{15}$ and $R_{17}$ to $R_{20}$, which may be the same or different, are each independently a hydrogen atom or a deuterium atom,
$L_1$ denotes a linker and is any one selected from the group consisting of a single bond and a substituted or unsubstituted arylene of 2 to 60 carbon atoms,
n is an integer of 1, and
$Ar_1$ and $Ar_2$, which may be the same or different, are each independently any one selected from the group consisting of a substituted or unsubstituted phenyl, a substituted or unsubstituted biphenyl, a substituted or unsubstituted terphenyl, a substituted or unsubstituted naphthyl, a substituted or unsubstituted anthryl, a substituted or unsubstituted phenanthryl, and a substituted or unsubstituted fluorenyl,
wherein the term 'substituted' in the expression 'substituted or unsubstituted' means having at least one substituent selected from the group consisting of a deuterium, a cyano, a halogen, an alkyl of 1 to 24 carbon atoms, a halogenated alkyl of 1 to 24 carbon atoms, an aryl of 6 to 24 carbon atoms, and an arylalkyl of 7 to 24 carbon atoms.

2. The organic compound as set forth in claim 1, wherein $Ar_1$ and $Ar_2$ in Chemical Formula A may be the same or different and are each independently a substituted or unsubstituted phenyl, a substituted or unsubstituted biphenyl, a substituted or unsubstituted terphenyl, a substituted or unsubstituted naphthyl, a substituted or unsubstituted anthryl, a substituted or unsubstituted phenanthryl, or a substituted or unsubstituted fluorenyl.

3. The organic compound as set forth in claim 1, wherein the linker $L_1$ in Chemical Formula A is a single bond or any one selected from the group consisting of the following Structural Formulas 1, 2, 4, 6, 7, and 9:

[Structural Formula 1]

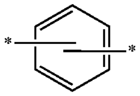

[Structural Formula 2]

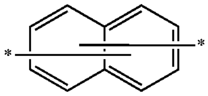

[Structural Formula 4]

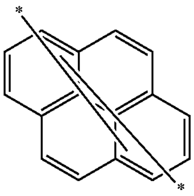

[Structural Formula 6]

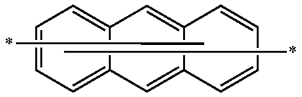

[Structural Formula 7]

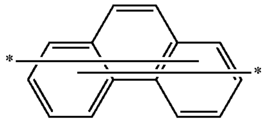

[Structural Formula 9]

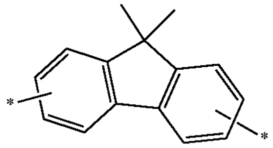

wherein carbon atoms in the aromatic ring moieties are bonded to a hydrogen atom or a deuterium atom.

4. The organic compound as set forth in claim 1, wherein the organic compound represented by Chemical Formula A is selected from the group consisting of the compounds represented by the following Compounds 301 to 308 and Compounds 317 to 320:

<Compound 301>

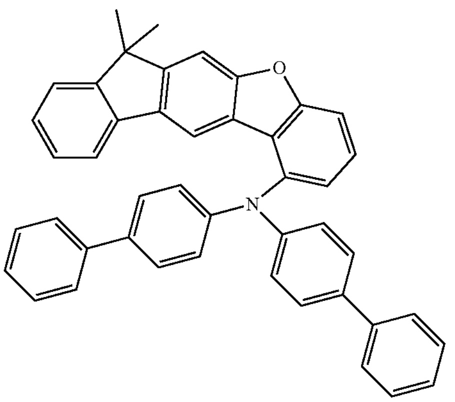

-continued

<Compound 302>

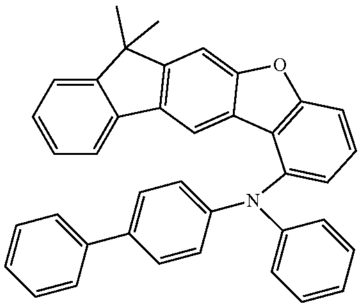

<Compound 303>

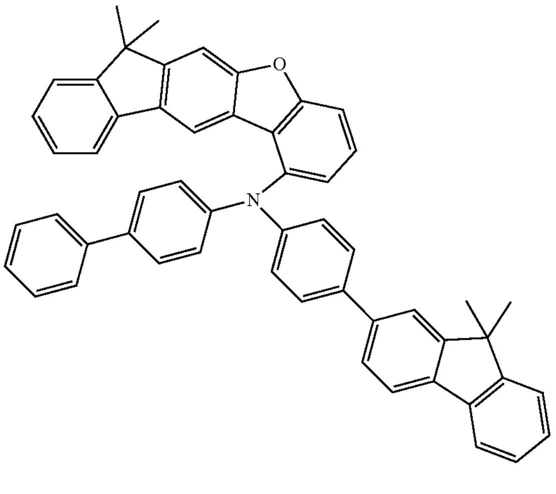

<Compound 304>

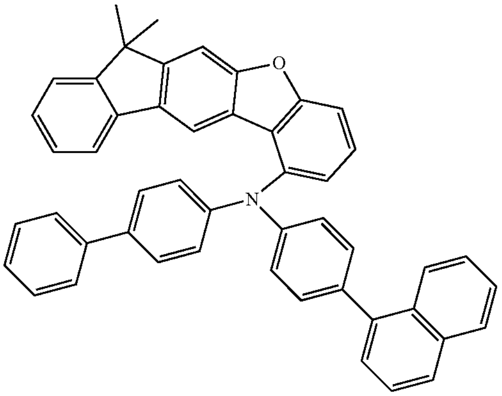

-continued

<Compound 305>

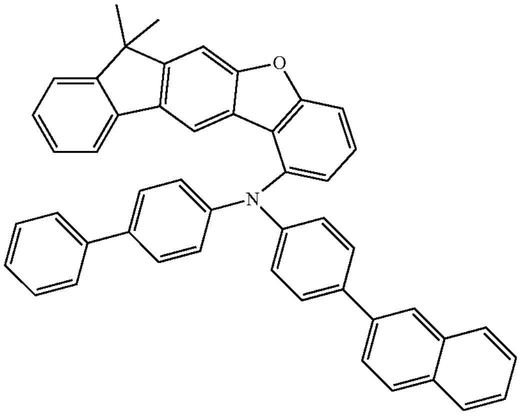

<Compound 306>

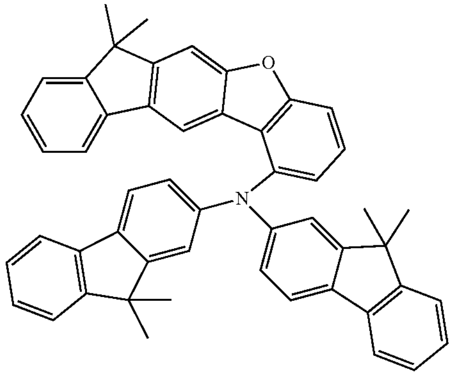

<Compound 307>

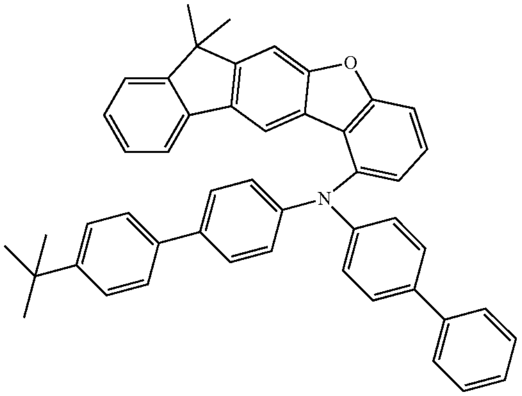

<Compound 308>

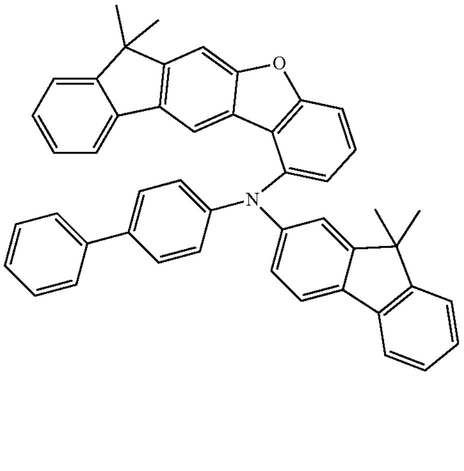

-continued

<Compound 317>

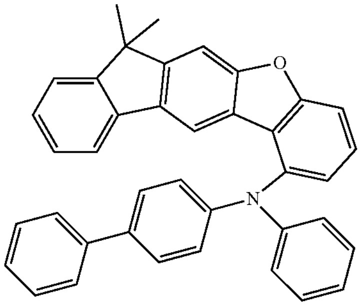

<Compound 318>

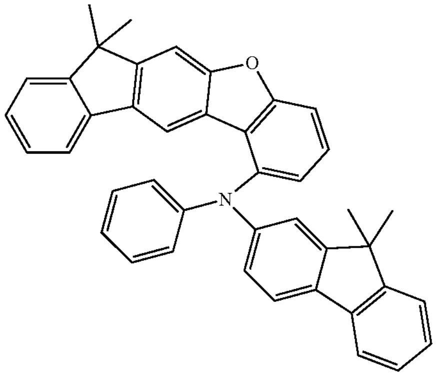

<Compound 319>

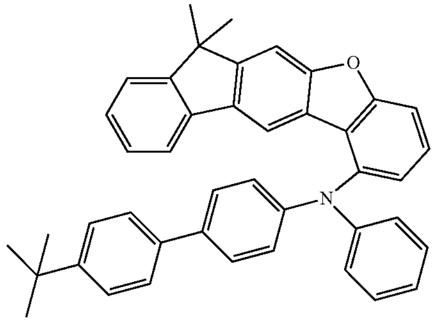

<Compound 320>

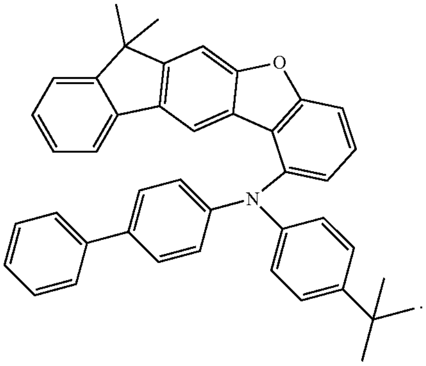

5. An organic light-emitting diode, including:

a first electrode;

a second electrode facing the first electrode; and an organic layer interposed the first electrode and the second electrode, wherein the organic layer contains the organic compound of claim 1.

6. The organic light-emitting diode as set forth in claim 5, wherein the organic layer includes at least one of a hole injection layer, a hole transport layer, a functional layer capable of both hole injection and hole transport, a light-emitting layer, an electron transport layer, or an electron injection layer.

7. The organic light-emitting diode as set forth in claim 6, wherein the organic compound is used for a hole transport layer.

8. The organic light-emitting diode as set forth in claim 6, wherein at least one of the layers is deposited using a deposition process or a solution process.

9. The organic light-emitting diode as set forth in claim 5, wherein the organic light-emitting diode is used for a device selected from the group consisting of a flat display device, a flexible display device, a monochrome or grayscale flat illumination device, and a monochrome or grayscale flexible illumination device.

* * * * *